(12) United States Patent
Hötzel et al.

(10) Patent No.: US 12,019,069 B2
(45) Date of Patent: Jun. 25, 2024

(54) SYNTHETIC CONTROLS FOR IMMUNOHISTOCHEMISTRY

(71) Applicant: Genentech, Inc., South San Francisco, CA (US)

(72) Inventors: Kathy Hötzel, Brisbane, CA (US); Franklin V. Peale, Jr., Hillsborough, CA (US); Charles Havnar, Pacifica, CA (US); Linda Rangell, Pacifica, CA (US); Debra Y. Dunlap, Redwood City, CA (US)

(73) Assignee: GENENTECH, INC., South San Francisco, CA (US)

( * ) Notice: Subject to any disclaimer, the term of this patent is extended or adjusted under 35 U.S.C. 154(b) by 911 days.

(21) Appl. No.: 16/888,252

(22) Filed: May 29, 2020

(65) Prior Publication Data

US 2020/0292536 A1 Sep. 17, 2020

Related U.S. Application Data

(63) Continuation of application No. PCT/US2018/064012, filed on Dec. 5, 2018.

(60) Provisional application No. 62/730,422, filed on Sep. 12, 2018, provisional application No. 62/595,434, filed on Dec. 6, 2017.

(51) Int. Cl.
| | |
|---|---|
| *G01N 33/53* | (2006.01) |
| *G01N 1/30* | (2006.01) |
| *G01N 1/36* | (2006.01) |
| *G01N 33/543* | (2006.01) |

(52) U.S. Cl.
CPC .......... *G01N 33/543* (2013.01); *G01N 1/30* (2013.01); *G01N 1/36* (2013.01); *G01N 2333/765* (2013.01); *G01N 2496/25* (2013.01)

(58) Field of Classification Search
None
See application file for complete search history.

(56) References Cited

U.S. PATENT DOCUMENTS

| | | | |
|---|---|---|---|
| 5,143,714 A | 9/1992 | Cosgrove et al. | |
| 2003/0157523 A1 | 8/2003 | Frantz et al. | |
| 2004/0229945 A1 | 11/2004 | Satchi-Fainaro et al. | |
| 2016/0041158 A1* | 2/2016 | Woodbury | G01N 33/54366 702/22 |

FOREIGN PATENT DOCUMENTS

| | | | |
|---|---|---|---|
| CN | 1727896 A | 2/2006 | |
| EP | 0345953 A2 | 12/1989 | |
| EP | 0352026 A2 | 1/1990 | |
| JP | H0232260 A | 2/1990 | |
| JP | H02210261 A | 8/1990 | |
| JP | 2005529870 A | 10/2005 | |
| JP | 2015172569 A | 10/2015 | |
| JP | 2016142731 A | 8/2016 | |
| JP | 2021518919 A | 8/2021 | |
| WO | 199105263 A1 | 4/1991 | |
| WO | 2003086382 A1 | 10/2003 | |

OTHER PUBLICATIONS

Duan et al., Separation of afrtificail antigen and egg yolk-derived immunoglobulin (lgY) of citrinin for enzyme-linked immunosorbent assay, Biomedical and Environmental Sciences, 22, 2009, pp. 237-243. (Year: 2009).*
European Examination Report mailed on May 20, 2021, for European Patent Application No. 18822568.4, 6 pages.
Extended European Search Report and Search Opinion mailed on Jun. 2, 2022, for European Patent Application No. 22157356.1, 10 pages.
Hötzel et al. (2019). "Synthetic Antigen Gels as Practical Controls for Standardized and Quantitative Immunohistochemistry," J. Histochem. Cytochem. 67(5):309-334.
International Preliminary Report, issued on Jun. 9, 2020, for PCT Application No. PCT/US2018/064012, filed on Dec. 5, 2018, 6 pages.
International Search Report, mailed on Jan. 28, 2019, for PCT Application No. PCT/US2018/064012, filed on Dec. 5, 2018, 6 pages.
Metz et al. (2004). "Identification of Formaldehyde-Induced Modifications in Proteins. Reaction With Model Peptides," J. Biol. Chem. 279(8):6235-6243.
Mourra et al. (1998). "Ultrastructure and Immunochemistry of Three-Dimensional Cultures of Human Keratocytes in Collagen Gel Matrix," Journal Francais D'Ophtalmologie 21(4):287-294. (In French with English Abstract).
Raja et al. (2015). "pH and Redox Sensitive Albumin Hydrogel: A Self-Derived Biomaterial," Scientific Reports 5(1):1-11.
Toda et al. (1999). "Immunohistochemical Expression of Growth Factors in Subacute Thyroiditis and Their Effects on Thyroid Folliculogenesis and Angiogenesis in Collagen Gel Matrix Culture," J. Pathol. 188:415-422.
Written Opinion, mailed on Jan. 28, 2019, for PCT Application No. PCT/US2018/064012, filed on Dec. 5, 2018, 8 pages.

* cited by examiner

*Primary Examiner* — Gary Counts
(74) *Attorney, Agent, or Firm* — MORRISON & FOERSTER LLP

(57) ABSTRACT

Provided herein are methods for generating a solid antigen/carrier protein gel for immunohistochemistry (IHC) staining, as well as gels, kits and methods of use thereto. In particular, the methods, gels and kits provided herein include a purified antigen such as a polypeptide antigen, and a carrier protein such as a serum albumin protein, an egg white protein or mixture of egg white proteins, gelatin, or polylysine. Examples are provided in which the purified antigen is cross-linked to the carrier protein in the solid antigen/carrier protein gel.

10 Claims, 39 Drawing Sheets

Specification includes a Sequence Listing.

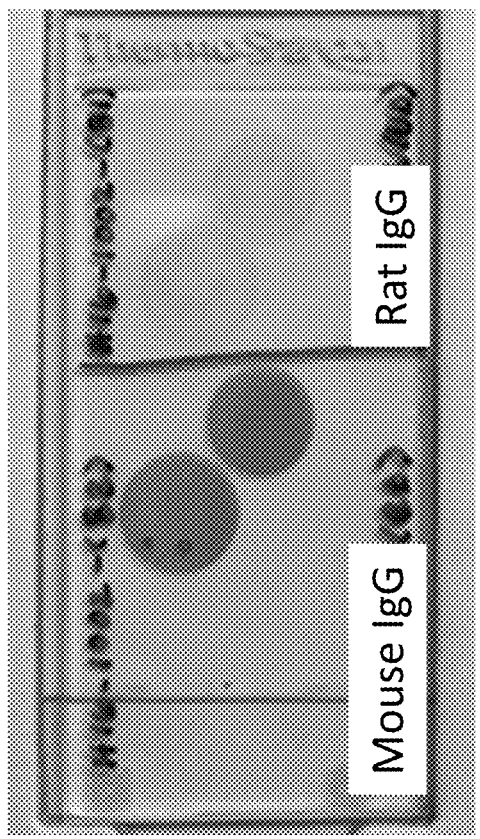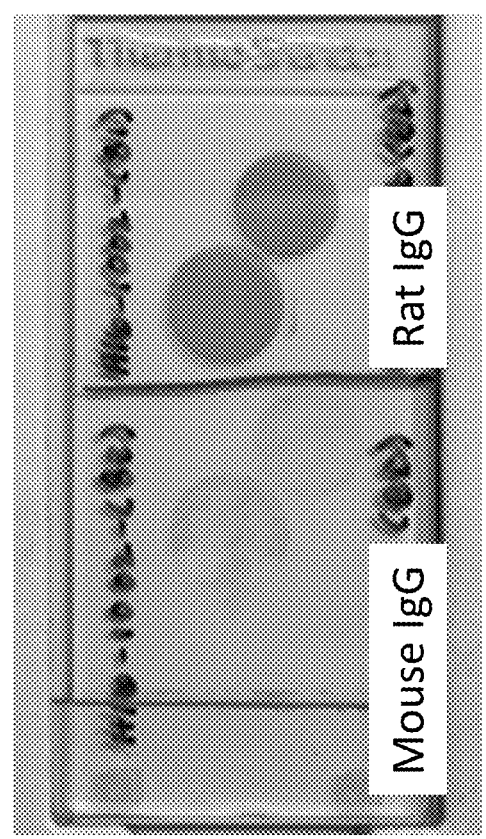

FIG. 5C

| Time (min) | Temperature °C | | | | |
|---|---|---|---|---|---|
| | 85 | 65 | 55 | 45 | 25 |
| 2 | S | L | L | L | L |
| 4 | S | semi-S | L | L | L |
| 6 | S | S | L | L | L |
| 8 | S | S | L | L | L |
| 10 | S | S | L | L | L |
| 20 | S | S | L | L | L |
| 30 | S | S | L | L | L |
| 60 | S | S | L | L | L |
| 120 | S | S | L | L | L |
| 180 | S | S | semi-S | L | L |
| 240 | S | S | semi-S | L | L |
| 300 | S | S | semi-S | L | L |
| 360 | S | S | semi-S | L | L |
| Overnight | S | S | S | L | L |

FIG. 6

| Time (min) | [20%] | | | [15%] | | | [10%] | | | [5%] | | | [2%] | | |
|---|---|---|---|---|---|---|---|---|---|---|---|---|---|---|---|
| | 85 | 55 | 45 | 85 | 55 | 45 | 85 | 55 | 45 | 85 | 55 | 45 | 85 | 55 | 45 |
| 2 | | L | L | | L | L | | L | L | | L | L | L | L | L |
| 4 | S | L | L | | L | L | | L | L | | L | L | L | L | L |
| 6 | S | L | L | S | L | L | S | L | L | | L | L | L | L | L |
| 8 | S | L | L | S | L | L | S | L | L | S | L | L | L | L | L |
| 10 | S | L | L | S | L | L | S | L | L | S | L | L | L | L | L |
| 20 | S | L | L | S | L | L | S | L | L | S | L | L | S | L | L |
| 30 | S | L | L | S | L | L | S | L | L | S | L | L | S | L | L |
| 60 | S | L | L | S | L | L | S | L | L | S | L | L | S | L | L |
| 120 | S | L | L | S | L | L | S | L | L | S | L | L | S | L | L |
| 180 | S | L | L | S | L | L | S | L | L | S | L | L | S | L | L |
| 240 | S | L | L | S | L | L | S | L | L | S | L | L | S | L | L |
| 300 | S | L | L | S | L | L | S | L | L | S | L | L | S | L | L |
| 360 | S | L | L | S | L | L | S | L | L | S | L | L | S | L | L |
| o/n | S | L | L | S | L | L | S | L | L | S | L | L | S | L | L |

[BSA conc] / temp C

FIG. 7

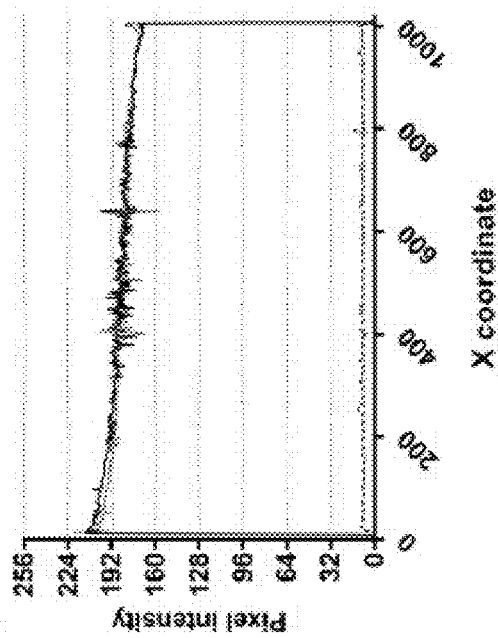
FIG. 11A
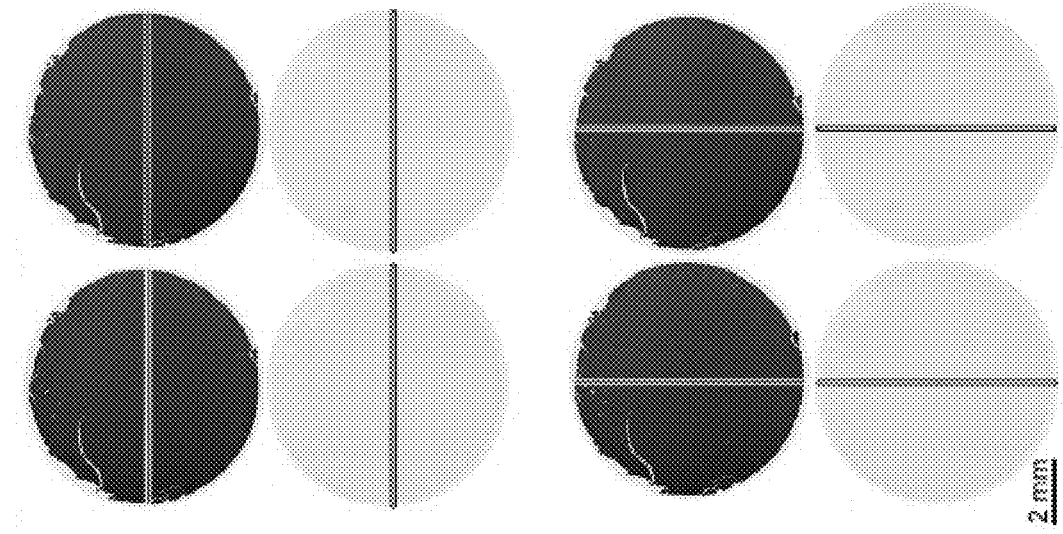
FIG. 11B
FIG. 11C
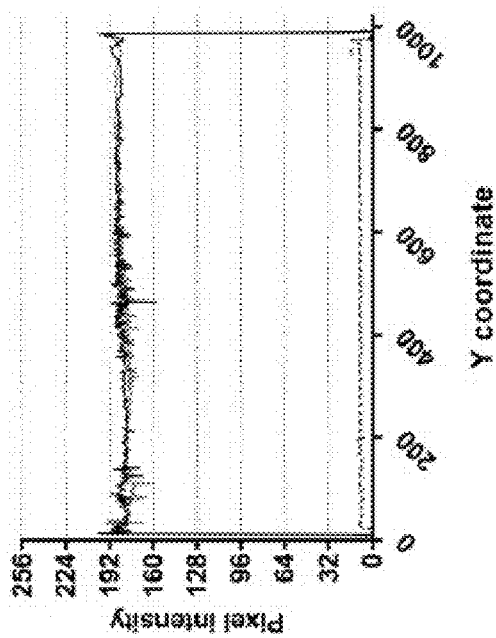
FIG. 11D

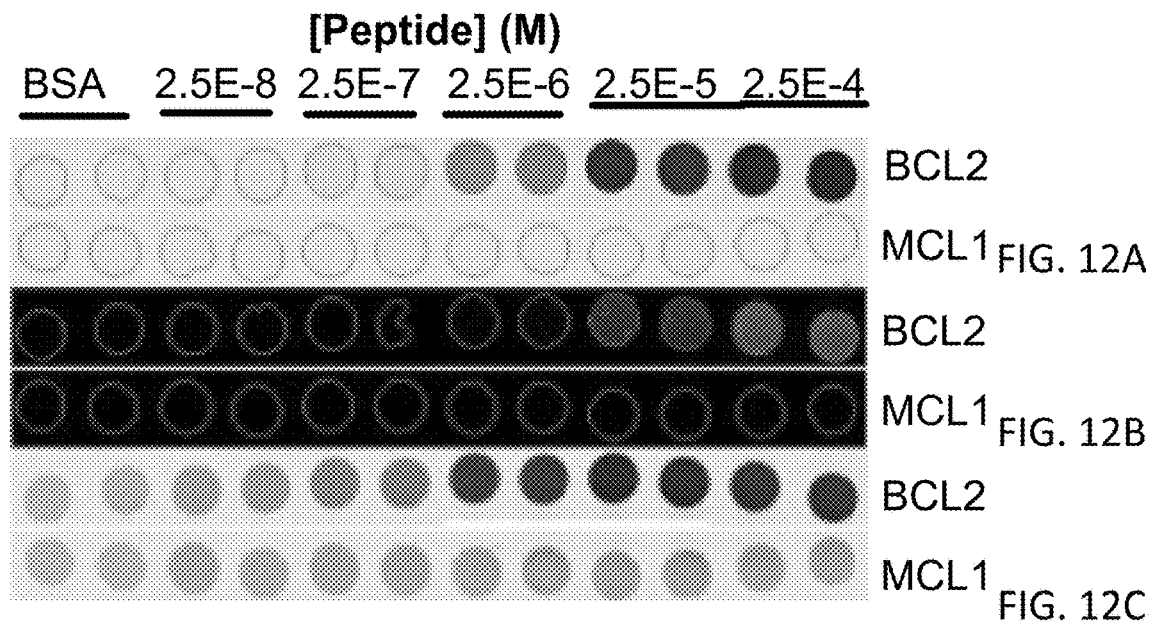
FIG. 12A
FIG. 12B
FIG. 12C
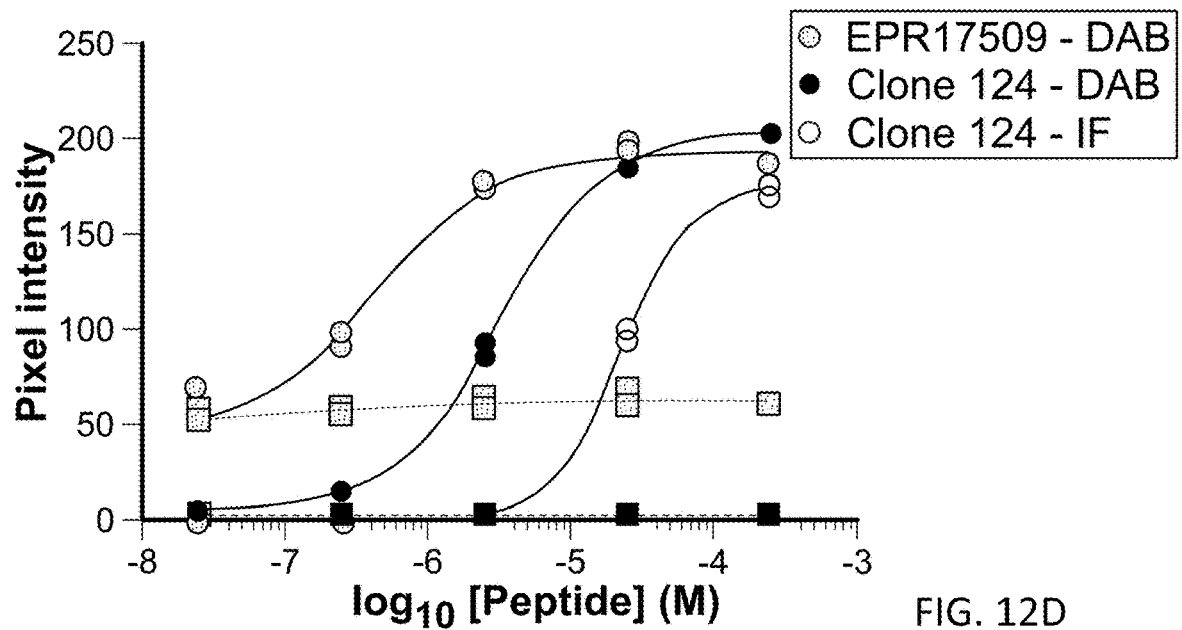
FIG. 12D
|  | BCL2 EPR17509 DAB | BCL2 Clone 124 DAB | BCL2 Clone 124 IF |
|---|---|---|---|
| Bottom | 44.9 | 5.5 | 0.003 |
| Top | 194 | 204 | 175 |
| Span | 149 | 198 | 175 |
| HillSlope | 1.01 | 1.17 | 1.78 |
| ACHM | 4.1e-7 | 3.3e-6 | 2.2e-5 |
FIG. 12E

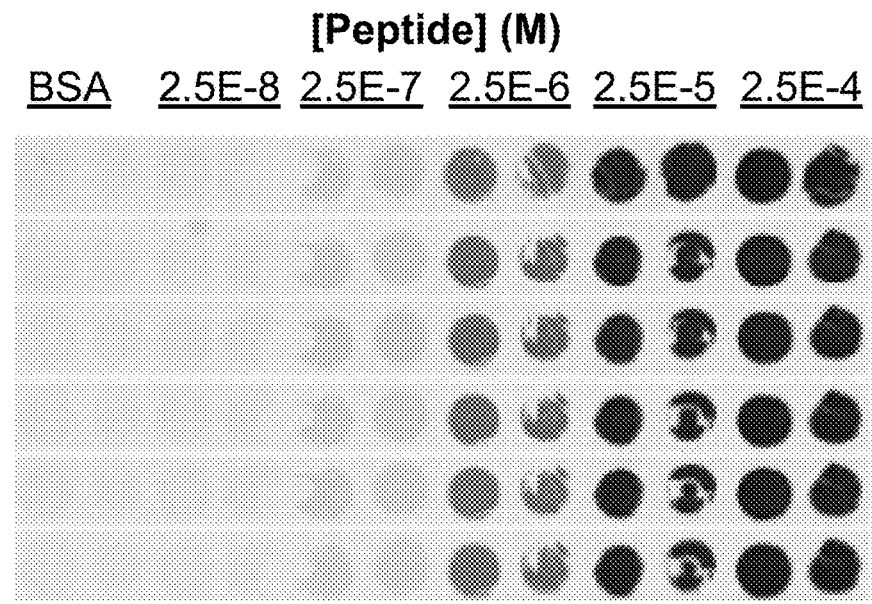
FIG. 14A
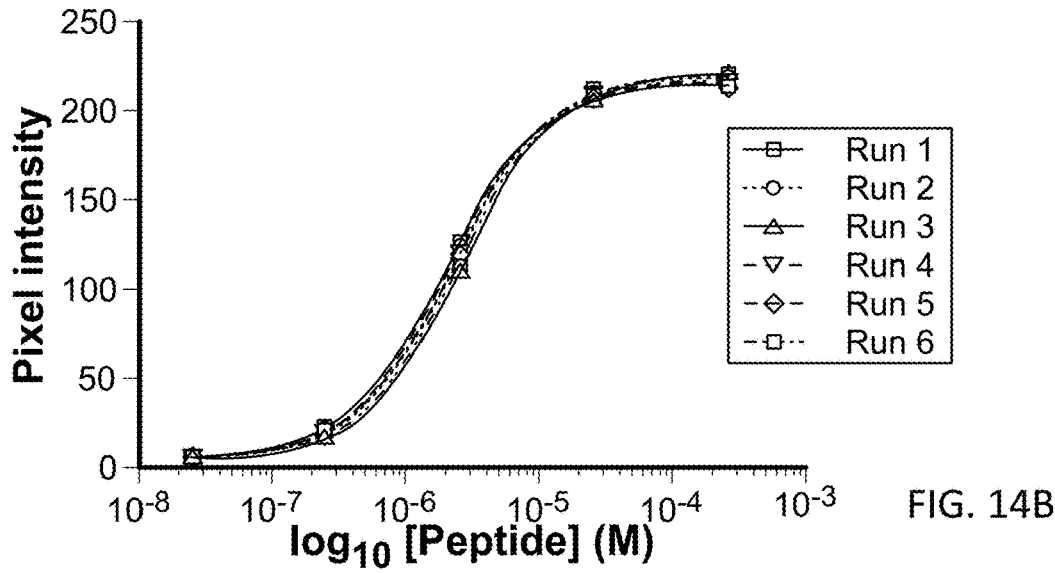
FIG. 14B
| | Mean | Range | St. Dev. |
|---|---|---|---|
| Bottom | 4.3 | 3.0 - 5.0 | 0.7 |
| Top | 217 | 215 - 220 | 2.3 |
| Span | 213 | 210 - 217 | 2.8 |
| HillSlope | 1.23 | 1.20 - 1.27 | 0.03 |
| ACHM | 2.24E-06 | 1.95 - 2.49E-6 | 2.1E-07 |
FIG. 14C FIG. 15A
FIG. 15B
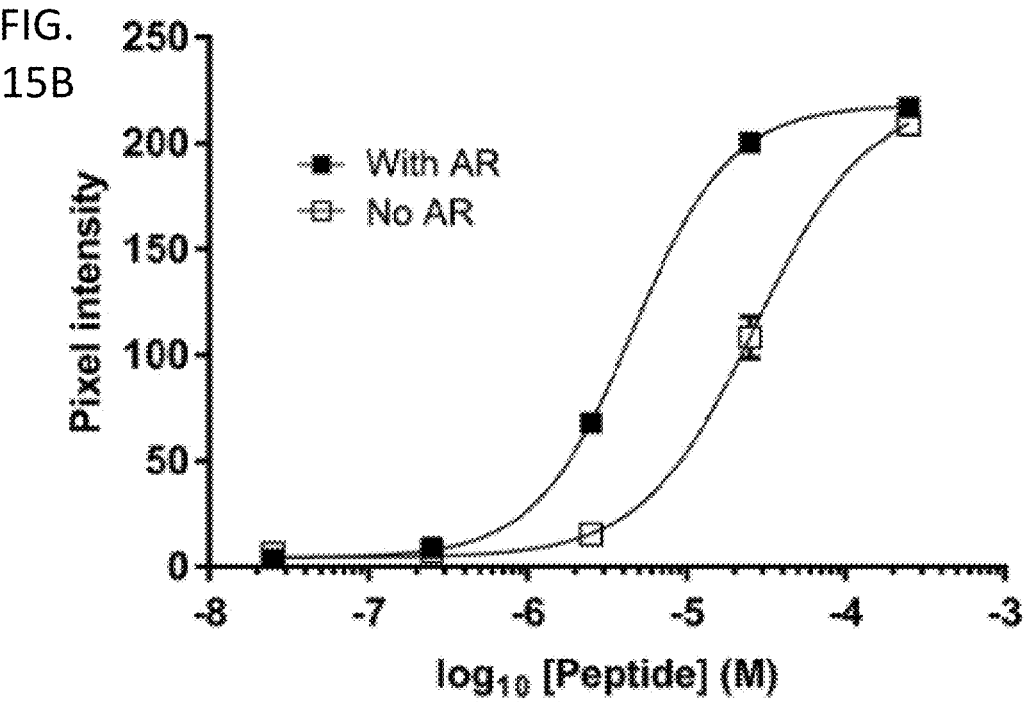
FIG. 15C
|  | With AR | Without AR |
|---|---|---|
| Bottom | 3.1 | 6.2 |
| Top | 218 | 220 |
| Span | 215 | 214 |
| HillSlope | 1.40 | 1.31 |
| ACHM | 4.53E-06 | 2.67E-05 |

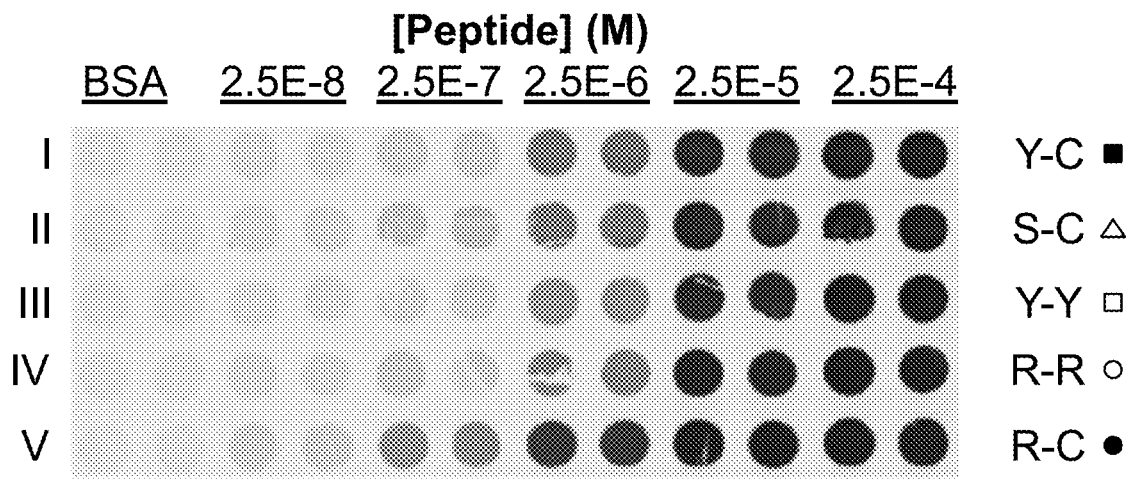
FIG. 16A
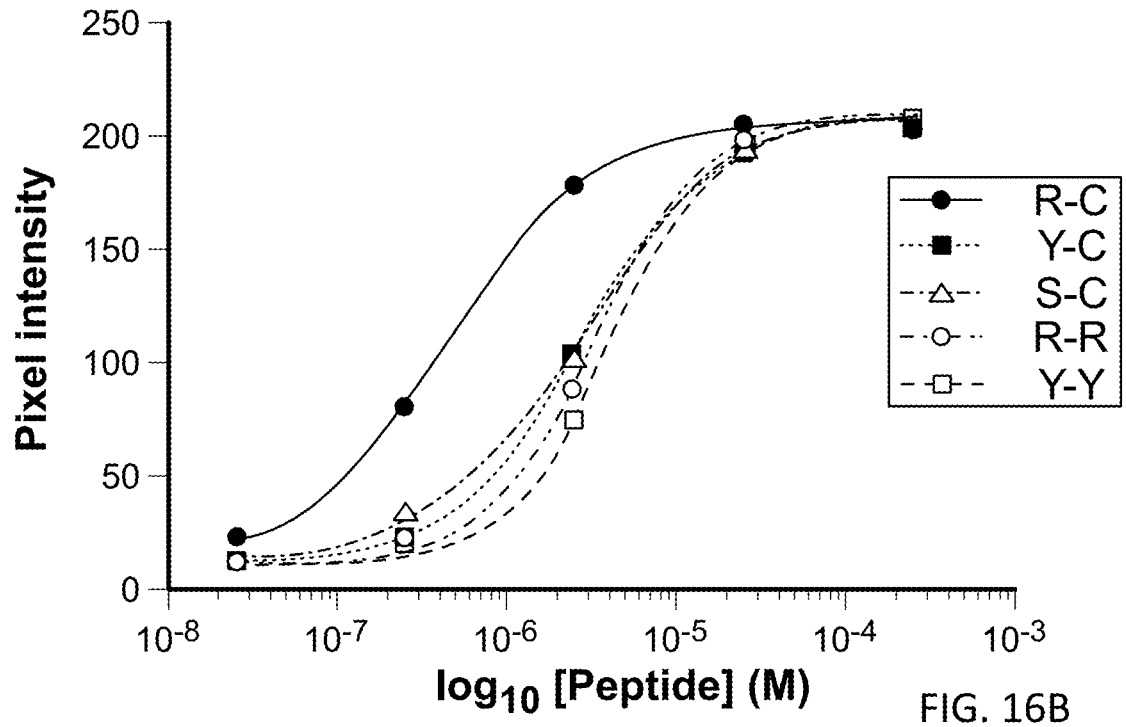
FIG. 16B
| | R-C | Y-C | S-C | R-R | Y-Y |
|---|---|---|---|---|---|
| Bottom | 9.0 | 9.9 | 9.7 | 9.2 | 9.5 |
| Top | 207 | 207 | 214 | 209 | 210 |
| Span | 198 | 197 | 205 | 200 | 200 |
| HillSlope | 0.99 | 1.15 | 0.91 | 1.30 | 1.35 |
| ACHM | 4.43E-07 | 2.70E-06 | 2.88E-06 | 3.36E-06 | 4.31E-06 |
FIG. 16C

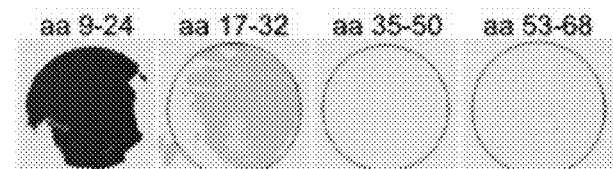
FIG. 17A
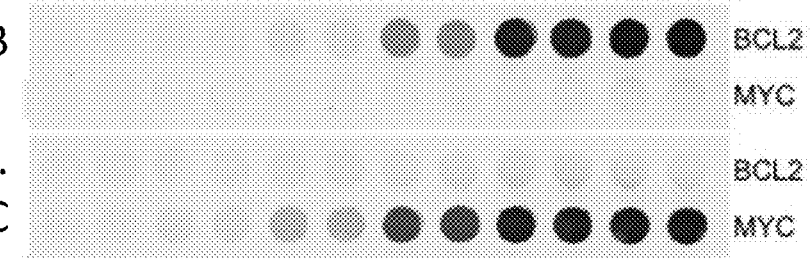
FIG. 17B
FIG. 17C
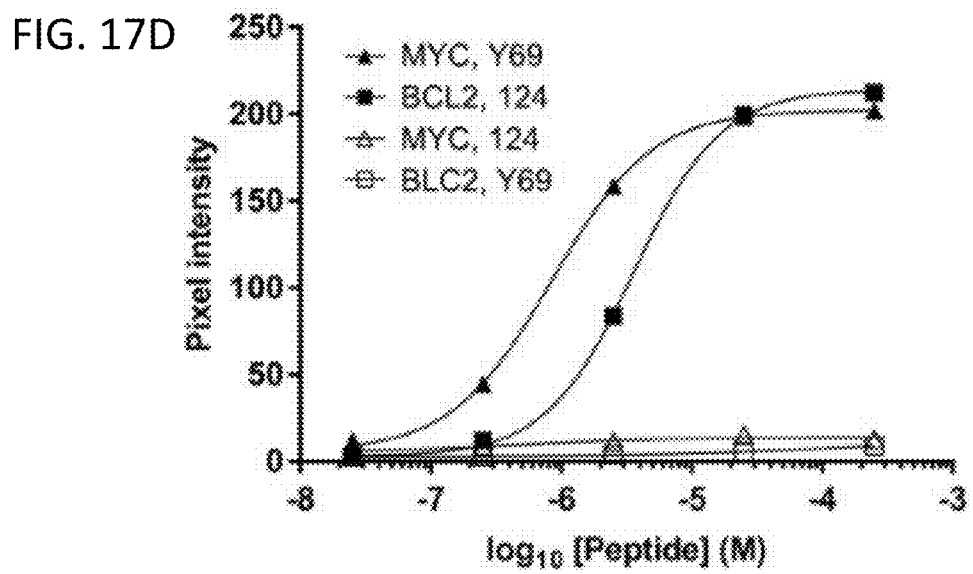
FIG. 17D
FIG. 17E
|  | BCL2 peptide clone 124 | MYC peptide clone Y69 |
|---|---|---|
| Bottom | 3.0 | 5.8 |
| Top | 214 | 202 |
| Span | 211 | 197 |
| HillSlope | 1.30 | 1.14 |
| ACHM | 3.57E-06 | 8.41E-07 |

FIG. 18A
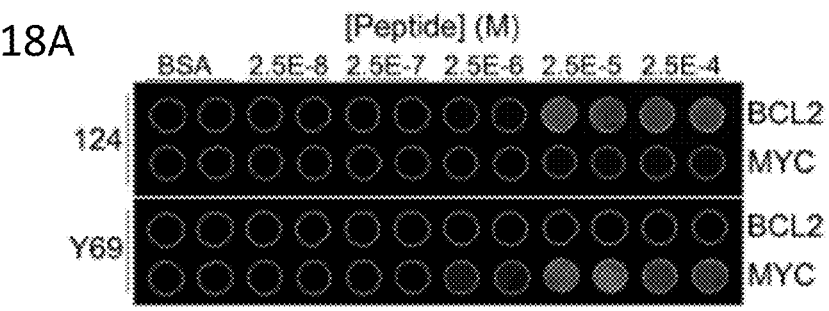
FIG. 18B
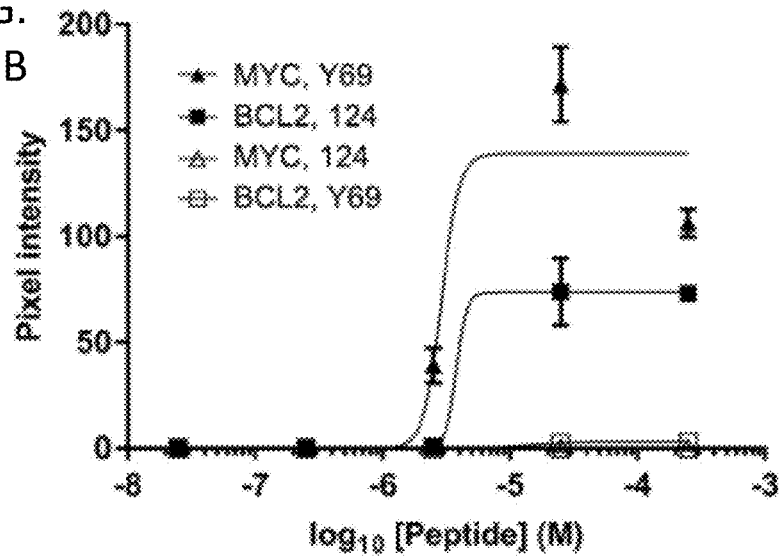
FIG. 18C
|  | MYC peptide clone Y69 | BCL2 peptide clone 124 |
|---|---|---|
| Bottom | 0 | 0 |
| Top | 139 | 73.5 |
| Span | 139 | 73.5 |
| HillSlope | 6.33 | 10.6 |
| ACHM | 2.90E-06 | 3.78E-06 |

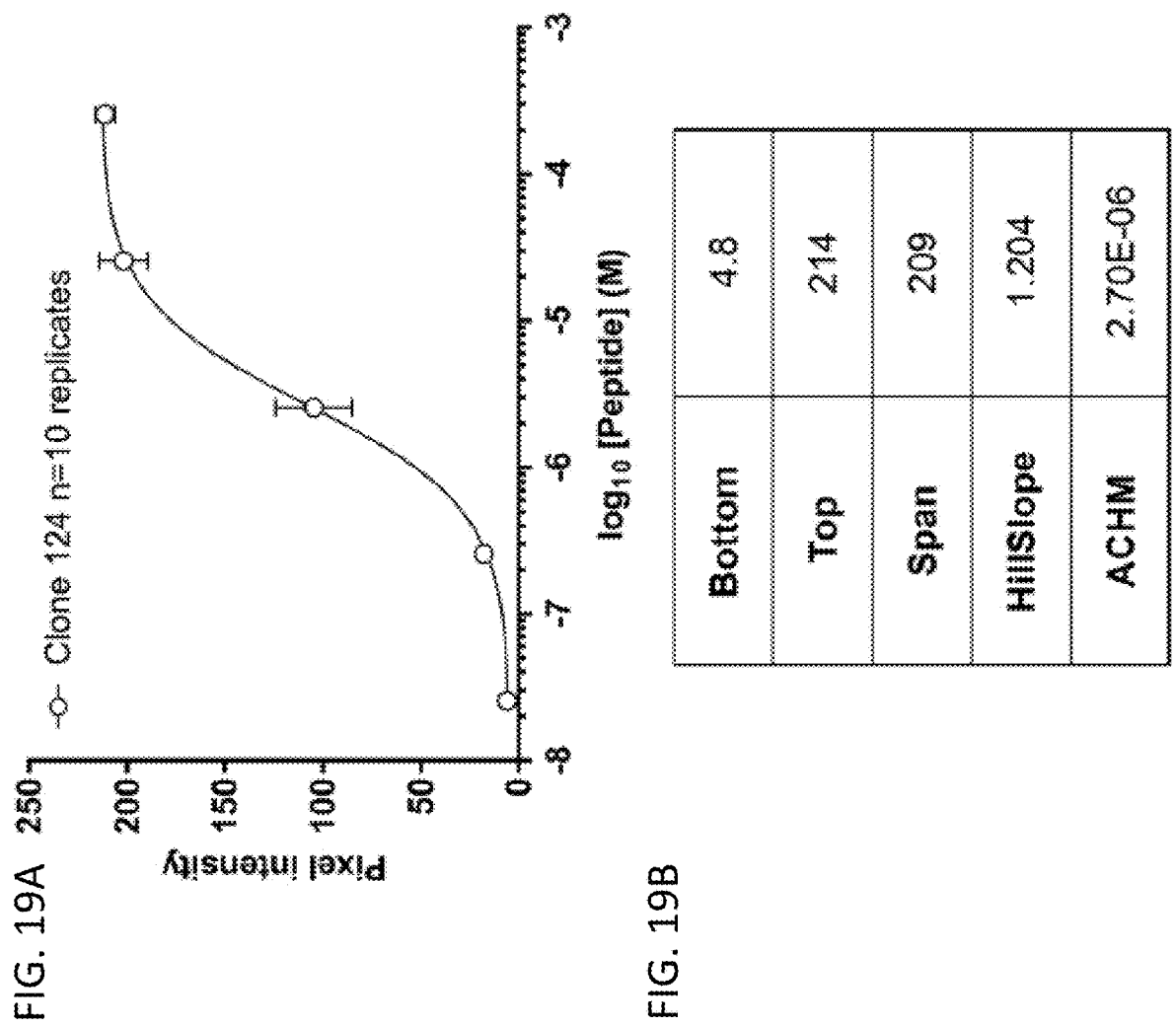

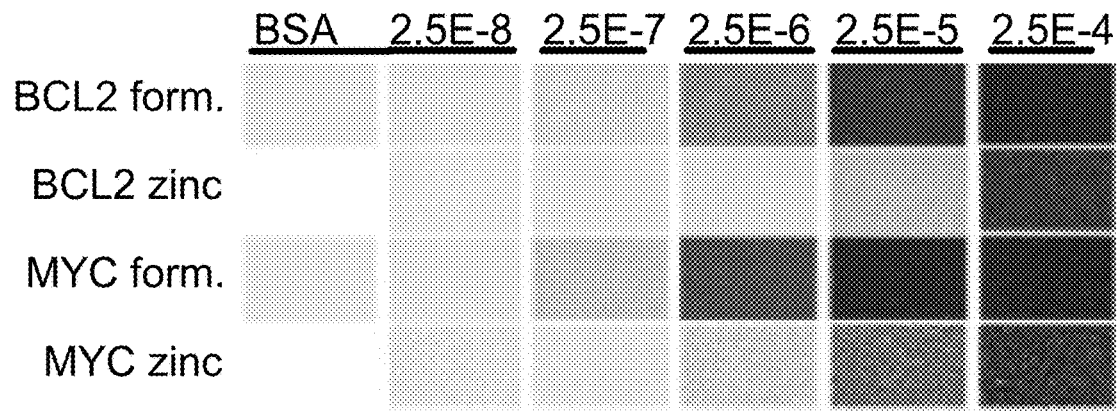
FIG. 22A
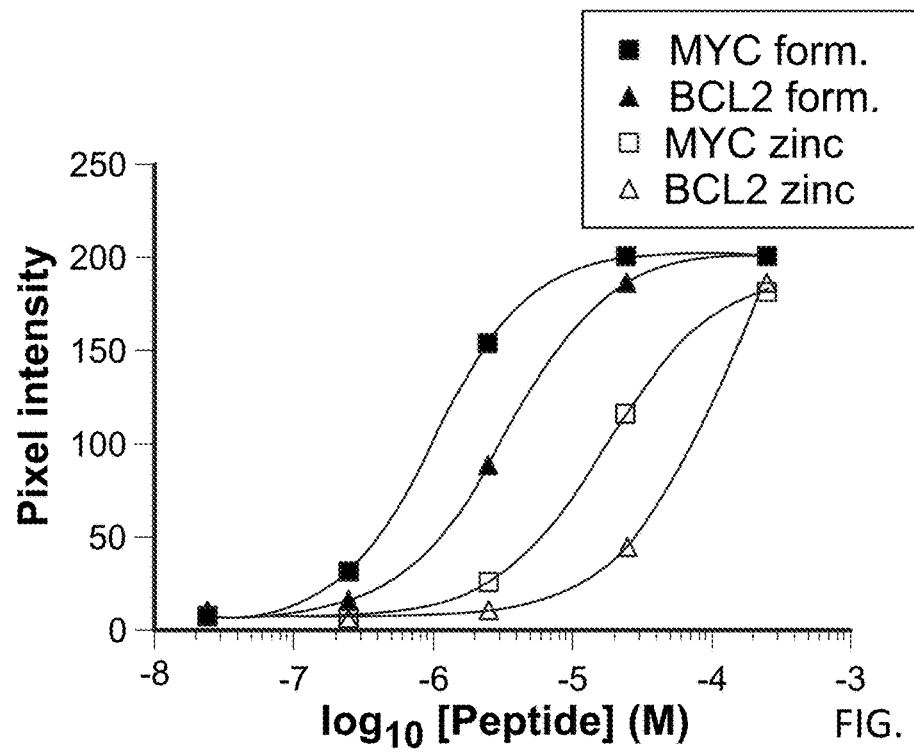
FIG. 22B
|  | MYC form. | BCL2 form. | MYC zinc | BCL2 zinc |
|---|---|---|---|---|
| Bottom | 3.3 | 5.5 | 6.4 | 6.9 |
| Top | 203 | 204 | 191 | 255 |
| Span | 200 | 198 | 184 | 248 |
| HillSlope | 1.278 | 1.168 | 1.116 | 1.122 |
| ACHM | 1.03E-06 | 3.29E-06 | 1.77E-05 | 1.11E-04 |
FIG. 22C

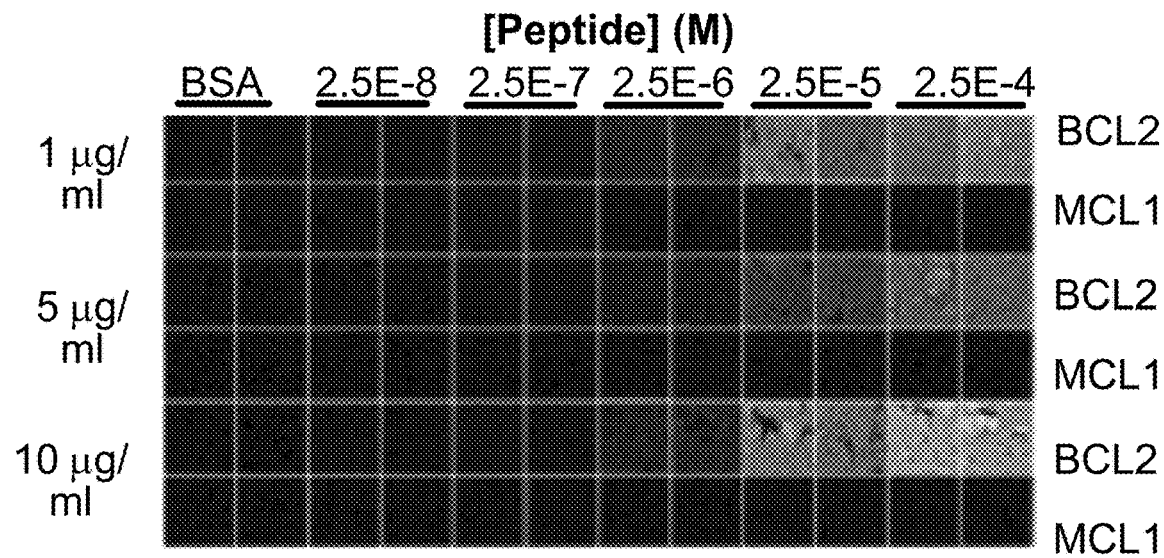
FIG. 24A
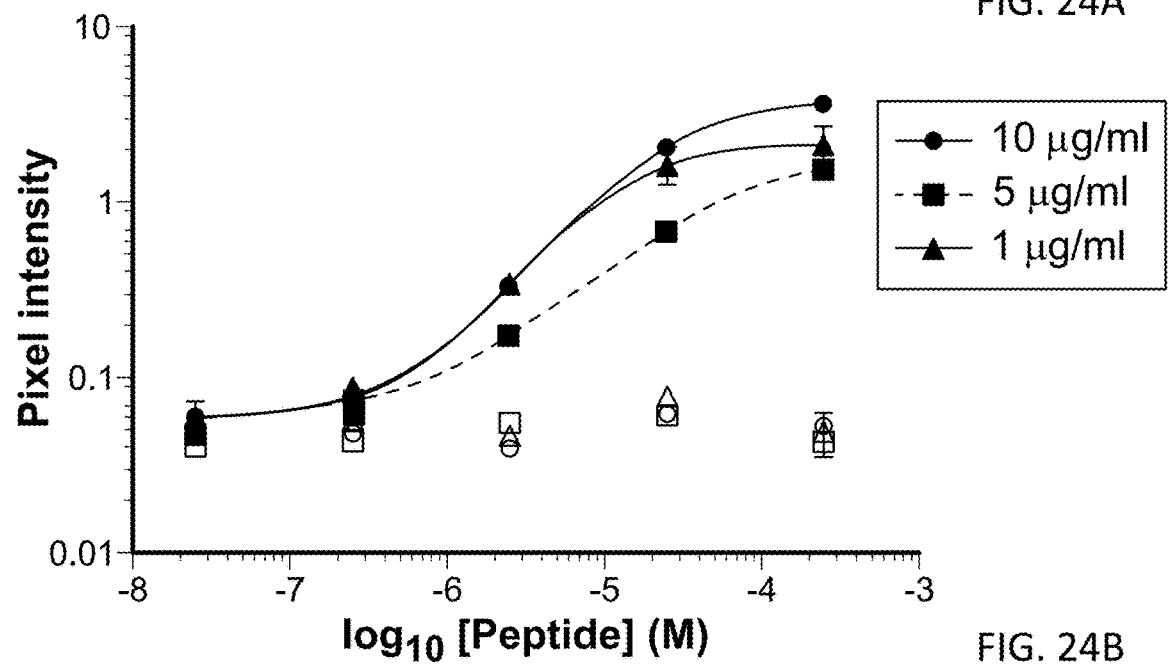
FIG. 24B
|          | 10 ug/ml | 5 ug/ml  | 1 ug/ml  |
|----------|----------|----------|----------|
| Bottom   | 0.052    | 0.050    | 0.059    |
| Top      | 3.98     | 2.05     | 2.24     |
| Span     | 3.93     | 2.00     | 2.19     |
| HillSlope| 1.13     | 0.847    | 1.26     |
| ACHM     | 2.35E-05 | 6.09E-05 | 1.12E-05 |
FIG. 24C

SEQUENCE LISTING

<160> NUMBER OF SEQ ID NOS: 7

<210> SEQ ID NO 1
<211> LENGTH: 22
<212> TYPE: PRT
<213> ORGANISM: Artificial Sequence
<220> FEATURE:
<223> OTHER INFORMATION: Synthetic Construct

<400> SEQUENCE: 1

Tyr Gly Ser Gly Gly Ala Ala Pro Ala Pro Gly Ile Phe Ser Ser Gln
1               5                   10                  15

Pro Gly Gly Ser Gly Cys
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic Construct

<400> SEQUENCE: 2

```
Tyr Gly Ser Gly Asn Arg Asn Tyr Asp Leu Asp Tyr Asp Ser Val Gln
1               5                   10                  15

Pro Tyr Phe Tyr Gly Ser Gly Cys
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic Construct

<400> SEQUENCE: 3

Tyr Gly Ser Gly Asp Ser Val Gln Pro Tyr Phe Tyr Cys Asp Glu Glu
1               5                   10                  15

Glu Asn Phe Tyr Gly Ser Gly Cys
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic Construct

<400> SEQUENCE: 4

Tyr Gly Ser Gly Gln Gln Gln Ser Glu Leu Gln Pro Pro Ala Pro Ser
1               5                   10                  15

Glu Asp Ile Trp Gly Ser Gly Cys
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic Construct

<400> SEQUENCE: 5

Tyr Gly Ser Gly Phe Glu Leu Leu Pro Thr Pro Pro Leu Ser Pro Ser
1               5                   10                  15

Arg Arg Ser Gly Gly Ser Gly Cys
            20

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Tyr Gly Ser Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct
```

-continued

```
<400> SEQUENCE: 7

Gly Ser Gly Cys
1
```

SYNTHETIC CONTROLS FOR IMMUNOHISTOCHEMISTRY

CROSS REFERENCE TO RELATED APPLICATIONS

This application is a continuation of International Application No. PCT/US2018/064012, filed Dec. 5, 2018, which claims the priority benefit of U.S. Provisional Application Serial Nos. 62/595,434, filed Dec. 6, 2017, and 62/730,422, filed Sep. 12, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) on the Sequence Listing (file name: 146392040401SEQLIST. TXT, date recorded: May 26, 2020, size: 3 KB).

FIELD

The present disclosure relates to synthetic controls useful, e.g., for immunohistochemistry (IHC), as well as methods of manufacture and uses related thereto. In some embodiments, the synthetic controls include a solid gel comprising a purified antigen (e.g., at a known quantity) cross-linked to a carrier protein such as a serum albumin protein, an egg white protein or a mixture of egg white proteins, or gelatin.

BACKGROUND

IHC represents an important tool for both research and clinical applications. Among the many techniques used to characterize protein expression, IHC is one of the few that provides information on expression level as well as localization, e.g., at the cellular and/or tissue levels. IHC is therefore a critical tool used in research to characterize a protein of interest. IHC has also become an important diagnostic tool in the clinic, e.g., to categorize patients for a variety of personalized medicine applications. As one example, the HercepTest™ (Dako Denmark A/S) semi-quantitative HER2 IHC assay has been approved by the FDA for use in assessing HER2 protein status for almost 20 years. This test allows clinicians to identify patients whose tumors overexpress HER2. While HER2 is overexpressed in many types of cancer, 25-30% of breast cancers have been shown to overexpress HER2, and this marker is correlated with shortened disease-free and overall survival. Therapies that target HER2 in these patients (e.g., anti-HER2 antibody treatment) provide significantly improved overall survival, response rate, duration of response, and time to disease progression. See, e.g., Slamon, D. J. et al. (2001) *N Engl J Med* 344:783-792.

Establishing a reliable IHC assay for a particular target presents multiple challenges. First, one must identify an antibody that is specific to the target of interest and does not cross-react with other targets. This requires appropriate positive and negative controls that express the target at known levels, which are difficult to identify when the target's expression is uncharacterized.

Second, even if an antibody is available, it can be difficult to identify positive and negative controls that are reliable, readily available, and easy to mass-produce. Tissue samples and cell lines (e.g., cell pellets) have both been used as IHC controls; however, both have significant limitations. For many targets, appropriate tissues are not available. For others, expression in tissues may be variable, uncharacterized, or too weak to detect. Cell lines are easier to obtain than tissue samples (although growing certain cell lines on an industrial scale can be difficult), but like expression in tissue samples, expression in cell lines can be variable, uncharacterized, or too weak to detect. One can engineer a cell line to overexpress a target of interest, but overexpression can be significantly higher than expression in actual tissues and can lead to artefactual subcellular localization. Overexpression can also be heterogeneous within a population of cultured cells. Cell lines can be produced in batches, but these can be quickly exhausted, requiring the production of new batches that can have different characteristics.

A variety of approaches aimed at establishing a standardized approach to generate IHC controls have been attempted. Over 45 years ago, Brandtzaeg described a method to create "artificial tissue" samples: millimeter-sized blocks of glutaraldehyde-fixed rabbit serum, into which human immunoglobulin fractions or whole serum were allowed to diffuse (Brandtzaeg, P. (1972) *Immunology*; 22(1):177-183). This general technique was revisited and extended with apparent success over the next dozen years (Millar and Williams (1982) *Histochem J.* 14(4):609-620; Schipper and Tilders (1983) *J Histochem Cytochem.* 31(1):12-18; Valnes et al. (1984) *J Histochem Cytochem.* 33(8):755-61; Valnes and Brandtzaeg (1985) *Histochemistry.* 81(4):313-9), but has also been described as prone to inhomogeneous and non-specific staining (Shi et al (2005) *J Histochem Cytochem.* 53(9):1167-1170), and has seen little use in recent practice. More widely used are clonal cell lines with variably well-characterized abundance of target proteins (Mohd Omar et al. (2010) *Acta Histochem.* 112(6):519-28). These are invaluable in many settings, but cell line controls can show remarkably heterogeneous expression of specific targets in separate subclones, different passages of one clone, or even within one culture population, frustrating the goal of creating a homogeneous and reproducible standard.

Sompuram, S. R. et al. (2002) *Clin Chem* 48:410-420 describe spotting peptides directly to glass slides, or coupling peptides to glass beads (see also Sompuram et al. (2015) *J. Histochem Cytochem* 63:681-690). However, implementation of this approach led to technical challenges. For example, since it was difficult for technicians to see the spots on which the peptides were applied to the glass (they are invisible prior to staining), many slides were stained with insufficient amounts of reagent to cover all of the controls, thereby leading to artifacts in staining (see Bogen, S. A. et al. (2009) *Appl Immunohistochem Mot Morphol* 17:239-246). These peptide spots were also much thinner than actual tissue sections, and therefore intense positive control staining was difficult to achieve. Other groups have tried to mix a target of interest in a lysozyme solution, which can be prepared like a formalin-fixed paraffin-embedded tissue section (see Fowler, C. B. et al. (2007) *Lab Invest* 87:836-846). They noted that gel formation depended on protein concentration and isoelectric point (Fowler et al., (2007) *Lab Invest.* 87(8):836-46.). However, this approach did not work for many targets, such as peptides, which can leak out of the lysozyme gelatin. Agarose was also tested as a potential tissue surrogate. However, the peptides dispersed in agarose were not homogeneous. In addition, subjecting these agarose-based peptide gels to antigen retrieval, which typically includes boiling, melted the agarose and caused it to separate on the glass slide.

Therefore, a need exists for an approach that provides reliable positive and negative IHC controls that are sensitive, specific, and can be adapted to a wide range of targets, including targets for which no suitable biological control exists. Such an approach would also provide a useful assay for determining antibody specificity, which is particularly advantageous when screening a large number of antibodies to identify and validate a new antibody specific for a target of interest, as well as for optimizing IHC staining protocols.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

SUMMARY

To meet these and other demands, provided herein are methods for generating a solid antigen/carrier protein gel. These solid gels can be processed like tissue samples or other biological samples according to standard IHC or electron microscopy (EM) processing methods (including fixation, sectioning, antigen retrieval, and so forth). Since the gels contain a known amount of an antigen of interest, they can be used, e.g., to create a series of gels having known concentrations of antigen to standardize staining with a particular antibody, or to screen for antibodies that specifically recognize an antigen of interest and are suitable for IHC/EM analyses. These methods are thought to provide a general platform that allows for control staining of any antigen of interest, simulating multiple levels of expression using known concentrations of antigen.

Certain aspects of the present disclosure relate to methods of generating a solid antigen/carrier protein gel (e.g., for IHC or EM analysis) comprising: (a) mixing a purified antigen with a liquid solution comprising a carrier protein selected from the group consisting of an albumin protein (e.g., a serum albumin protein), an egg white protein or a mixture of egg white proteins, and gelatin to produce an antigen/carrier protein liquid solution; and (b) heating the antigen/carrier protein liquid solution to form the solid antigen/carrier protein gel. In some embodiments, the methods comprise: (a) mixing a purified antigen with a liquid solution comprising a carrier protein selected from the group consisting of an albumin protein (e.g., a serum albumin protein), an egg white protein or a mixture of egg white proteins, gelatin, and poly-lysine to produce an antigen/carrier protein liquid solution; and (b) heating the antigen/carrier protein liquid solution to form the solid antigen/carrier protein gel. In some embodiments, the methods further comprise, after (b): dehydrating the solid antigen/carrier protein gel and embedding the dehydrated solid antigen/carrier protein gel in a paraffin block. In some embodiments, the methods further comprise, after embedding the dehydrated solid antigen/carrier protein gel in the paraffin block: transferring a core comprising the antigen/carrier protein gel from the paraffin block to a recipient tissue microarray (TMA) block. In some embodiments, the methods further comprise, after (b): incubating the solid antigen/carrier protein gel in a liquid embedding medium and freezing the solid antigen/carrier protein gel in the embedding medium. In some embodiments, the methods further comprise, after (b): embedding the solid antigen/carrier protein gel in a plastic resin. In some embodiments, the methods further comprise, after (b): sectioning the solid antigen/carrier protein gel into one or more solid antigen/carrier protein gel sections having a thickness of between about 30 nm and about 50 μm. In some embodiments, the solid antigen/carrier protein gel is sectioned into one or more solid antigen/carrier protein gel sections having a thickness of between about 2 μm and about 30 μm. In some embodiments, the solid antigen/carrier protein gel is sectioned into one or more solid antigen/carrier protein gel sections having a thickness of between about 30 nm and about 100 nm. In some embodiments, the methods further comprise, prior to (b), including a fixative in the antigen/carrier protein liquid solution. In some embodiments, the fixative comprises formaldehyde. In some embodiments, the antigen/carrier protein liquid solution comprises formaldehyde at a final concentration of at least about 1%. In some embodiments, the fixative comprises glutaraldehyde, Davidson's fixative, Bouin's fixative, ½ strength Karnovski's fixative, or a zinc salt. In some embodiments, the methods further comprise subjecting the solid antigen/carrier protein gel to antigen retrieval. In some embodiments, subjecting the solid antigen/carrier protein gel to antigen retrieval comprises heating the solid antigen/carrier protein gel in a liquid solution. In some embodiments, the methods further comprise: prior to (b), including a fixative in the antigen/carrier protein liquid solution; after (b), dehydrating the solid antigen/carrier protein gel; embedding the dehydrated solid antigen/carrier protein gel in a paraffin block; sectioning the paraffin block with the embedded antigen/carrier protein gel into one or more sections having a thickness of between about 30 nm and about 50 μm; subjecting the one or more sections of the embedded solid antigen/carrier protein gel to antigen retrieval; and after antigen retrieval, blocking the one or more sections of the embedded solid antigen/carrier protein gel. In some embodiments, the methods further comprise: after (b), incubating the solid antigen/carrier protein gel in a liquid embedding medium; freezing the solid antigen/carrier protein gel in the embedding medium; sectioning the frozen antigen/carrier protein gel into one or more sections having a thickness of between about 30 nm and about 50 μm; and blocking the one or more sections of the frozen antigen/carrier protein gel. In some embodiments, the antigen is a polypeptide antigen. In some embodiments, the antigen comprises an N-terminal tyrosine, a C-terminal cysteine, or both. In some embodiments, the methods further comprise prior to (b), cross-linking the antigen with the carrier protein (e.g., albumin protein, egg white protein or mixture of egg white proteins, or gelatin) using a cysteine-reactive reagent. In some embodiments, the antigen comprises a non-polypeptide antigen. In some embodiments, the carrier protein is an albumin protein, such as bovine, goat, horse, or human serum albumin. In some embodiments, the carrier protein is an egg white protein or a mixture of egg white proteins. In some embodiments, the antigen/carrier protein liquid solution produced in (a) comprises the carrier protein at a concentration of greater than or equal to 2% (w/v). In some embodiments, the antigen/carrier protein liquid solution produced in (a) comprises the carrier protein at a final concentration of less than or equal to about 25% (w/v). In some embodiments, the carrier protein is gelatin, and the method further comprises, after (b), cooling the heated antigen/carrier protein liquid solution to form the solid antigen/carrier protein gel. In some embodiments, the method further comprises, after cooling the heated antigen/carrier protein liquid solution: incubating the solid antigen/carrier protein gel with a fixative to form a fixed antigen/carrier protein gel; and dehydrating the fixed antigen/carrier protein gel. In some embodiments, the antigen/carrier protein liquid solution produced in (a) comprises the carrier protein at a concentration of greater than or equal to about 0.5% (w/v). In some embodiments, the antigen/carrier protein liquid solution is heated in (b) to at least about 65° C. In some embodiments, the antigen/carrier protein liquid solution is heated in (b) to at least about 65° C. for at least 6 minutes. In some embodiments, the poly-lysine is present in the antigen/carrier protein liquid solution produced in (a) at a concentration of about 14 mg/mL.

Further provided herein are solid antigen/carrier protein gels produced by the method according to any one of the above embodiments.

Further provided herein are tissue microarrays (TMAs) comprising at least a first solid antigen/carrier protein gel produced by the method according to any one of the above embodiments and a second solid antigen/carrier protein gel produced by the method according to any one of the above embodiments.

Certain aspects of the present disclosure relate to methods for immunohistochemical (IHC) staining of an antigen, comprising: providing a solid antigen/carrier protein gel produced by the method of any one of the above embodiments, wherein the solid antigen/carrier protein gel contains the antigen; providing a sample; contacting the solid antigen/carrier protein gel and the sample with a primary antibody that specifically binds the antigen; after contacting the solid antigen/carrier protein gel and the sample with the primary antibody, contacting the solid antigen/carrier protein gel and the sample with a secondary antibody that specifically binds the primary antibody, wherein a detectable moiety is conjugated to the secondary antibody; detecting a signal of the detectable moiety from the solid antigen/carrier protein gel; and detecting a signal of the detectable moiety from the sample, wherein detection of a signal from the sample as compared to the signal detected from the solid antigen/carrier protein gel indicates the presence of the antigen in the sample. In some embodiments, the detectable moiety comprises an enzyme, and wherein detecting the signal of the detectable moiety comprises exposing the detectable moiety to a chromogenic, fluorescent, or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle). In some embodiments, the sample is a tissue sample.

Certain aspects of the present disclosure relate to methods for control immunohistochemical (IHC) staining of an antigen, comprising: providing a first and a second solid antigen/carrier protein gel, wherein each of the first and the second solid antigen/carrier protein gels is produced by the method of any one of the above embodiments, wherein the first solid antigen/carrier protein gel contains the antigen at a first concentration, and wherein the second solid antigen/carrier protein gel contains the antigen at a second concentration higher than the first concentration; contacting the first and the second solid antigen/carrier protein gels with a primary antibody that specifically binds the antigen; after contacting the first and the second solid antigen/carrier protein gels with the primary antibody, contacting the first and the second solid antigen/carrier protein gels with a secondary antibody that specifically binds the primary antibody, wherein a detectable moiety is conjugated to the secondary antibody; detecting a first signal of the detectable moiety from the first solid antigen/carrier protein gel; and detecting a second signal of the detectable moiety from the second solid antigen/carrier protein gel, wherein detection of a second signal greater than the first signal indicates control IHC staining of the antigen. In some embodiments, the detectable moiety comprises an enzyme, and wherein detecting the signal of the detectable moiety comprises exposing the detectable moiety to a chromogenic, fluorescent or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle). In some embodiments, the first concentration is 0 nM, and wherein detection of a lack of a first signal indicates control IHC staining of the antigen. In some embodiments, the methods further comprise: providing a sample; contacting the sample with the primary antibody; after contacting the sample with the primary antibody, contacting the sample with the secondary antibody, wherein a detectable moiety is conjugated to the secondary antibody; detecting a third signal of the detectable moiety from the sample; and comparing the third signal with the first and the second signals, wherein an amount of the third signal relative to the amounts of the first and the second signals indicates an abundance of the antigen in the sample, relative to the amounts of the antigen in the first and the second solid antigen/carrier protein gels.

Certain aspects of the present disclosure relate to methods for control immunohistochemical (IHC) staining with a secondary antibody, comprising: providing a first and a second solid antigen/carrier protein gel, wherein each of the first and the second solid antigen/carrier protein gels is produced by the method of any one of the above embodiments, wherein the first solid antigen/carrier protein gel comprises a first antibody having a first isotype, and wherein the second solid antigen/carrier protein gel comprises a second antibody having a second isotype different from the first isotype; contacting the first and the second solid antigen/carrier protein gels with a secondary antibody that specifically binds the first isotype, wherein a detectable moiety is conjugated to the secondary antibody; detecting a signal of the detectable moiety from the first solid antigen/carrier protein gel; and detecting a lack of the signal of the detectable moiety from the second solid antigen/carrier protein gel, wherein detection of the signal associated with the first solid antigen/carrier protein gel and the lack of the signal associated with the second solid antigen/carrier protein gel indicates control staining with the secondary antibody. In some embodiments, the detectable moiety comprises an enzyme, and wherein detecting the signal of the detectable moiety comprises exposing the detectable moiety to a chromogenic, fluorescent or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle).

Certain aspects of the present disclosure relate to solid antigen/carrier protein gels (e.g., for immunohistochemical (IHC) staining) comprising a purified antigen cross-linked to a carrier protein selected from the group consisting of an albumin protein (e.g., a serum albumin protein), an egg white protein or a mixture of egg white proteins, and gelatin. In some embodiments, the present disclosure relates to solid antigen/carrier protein gels (e.g., for immunohistochemical (IHC) staining) comprising a purified antigen cross-linked to a carrier protein selected from the group consisting of an albumin protein (e.g., a serum albumin protein), an egg white protein or a mixture of egg white proteins, gelatin, and poly-lysine. In some embodiments, the solid gel has a thickness of between about 30 nm and about 50 µm. In some embodiments, the solid gel has a thickness of between about 2 µm and about 30 µm. In some embodiments, the solid gel has a thickness of between about 30 nm and about 100 nm. In some embodiments, the solid gel is frozen in an embedding medium. In some embodiments, the solid gel is embedded in paraffin. In some embodiments, the solid gel is embedded in a plastic resin. In some embodiments, the solid gel is affixed to a solid substrate. In some embodiments, the solid gel has been fixed in a fixative. In some embodiments, the fixative comprises formaldehyde. In some embodiments, the fixative comprises formaldehyde at a concentration of at least about 1%. In some embodiments, the fixative comprises glutaraldehyde, Davidson's fixative, Bouin's fixative, ½ strength Karnovski's fixative, or a zinc salt. In some embodiments, the solid gel has been subjected to antigen retrieval. In some embodiments, the antigen is a polypeptide antigen. In some embodiments, the antigen comprises an N-terminal tyrosine, a C-terminal cysteine, or both. In some embodiments, the N-terminal tyrosine and/or C-terminal cysteine is cross-linked to the carrier protein. In some embodiments, the antigen comprises a non-polypeptide antigen. In some embodiments, the carrier protein is an albumin protein, such as bovine, goat, horse, or human serum albumin. In some embodiments, the carrier protein is an egg white protein or a mixture of egg white proteins. In some embodiments, the solid gel comprises the carrier protein at a concentration of greater than or equal to 2%. In some embodiments, the solid gel comprises the carrier protein at a concentration of less than or equal to about 25%. In some embodiments, the carrier protein is gelatin. In some embodiments, the solid gel comprises the carrier protein at a concentration of greater than or equal to 0.5%. In some embodiments, the solid gel contains the antigen at a concentration of at least about 25 nM. In some embodiments, the solid gel comprises poly-lysine at a concentration of about 14 mg/mL.

Certain aspects of the present disclosure relate to tissue microarrays (TMAs) comprising at least a first and a second solid antigen/carrier protein gel, wherein the first and second solid antigen/carrier protein gels both comprise a purified antigen cross-linked to a carrier protein selected from the group consisting of an albumin protein, an egg white protein or mixture of egg white proteins, and gelatin. In some embodiments, the present disclosure relates to tissue microarrays (TMAs) comprising at least a first and a second solid antigen/carrier protein gel, wherein the first and second solid antigen/carrier protein gels both comprise a purified antigen cross-linked to a carrier protein selected from the group consisting of an albumin protein, an egg white protein or mixture of egg white proteins, gelatin, and poly-lysine. In some embodiments, the first solid antigen/carrier protein gel comprises a first purified antigen, and the second solid antigen/carrier protein gel comprises a second purified antigen different from the first purified antigen. In some embodiments, the first solid antigen/carrier protein gel comprises a first purified antigen at a first concentration, and the second solid antigen/carrier protein gel comprises the first purified antigen at a second concentration different from the first concentration.

Certain aspects of the present disclosure relate to methods for immunohistochemical (IHC) staining of an antigen, comprising: providing a solid antigen/carrier protein gel according to any one of the above embodiments, wherein the solid antigen/carrier protein gel contains the antigen; providing a sample; contacting the solid antigen/carrier protein gel and the sample with a primary antibody that specifically binds the antigen; after contacting the solid antigen/carrier protein gel and the sample with the primary antibody, contacting the solid antigen/carrier protein gel and the sample with a secondary antibody that specifically binds the primary antibody, wherein a detectable moiety is conjugated to the secondary antibody; detecting a signal of the detectable moiety from the solid antigen/carrier protein gel; and detecting a signal of the detectable moiety from the sample, wherein detection of a signal from the sample as compared to the signal detected from the solid antigen/carrier protein gel indicates the presence of the antigen in the sample. In some embodiments, the detectable moiety comprises an enzyme, and wherein detecting the signal of the detectable moiety comprises exposing the detectable moiety to a chromogenic, fluorescent or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle). In some embodiments, the sample is a tissue sample.

Certain aspects of the present disclosure relate to methods for control immunohistochemical (IHC) staining of an antigen, comprising: providing a first and a second solid antigen/carrier protein gel according to any one of the above embodiments, wherein the first solid antigen/carrier protein gel contains the antigen at a first concentration, and wherein the second solid antigen/carrier protein gel contains the antigen at a second concentration higher than the first concentration; contacting the first and the second solid antigen/carrier protein gels with a primary antibody that specifically binds the antigen; after contacting the first and the second solid antigen/carrier protein gels with the primary antibody, contacting the first and the second solid antigen/carrier protein gels with a secondary antibody that specifically binds the primary antibody, wherein a detectable moiety is conjugated to the secondary antibody; detecting a first signal of the detectable moiety from the first solid antigen/carrier protein gel; and detecting a second signal of the detectable moiety from the second solid antigen/carrier protein gel, wherein detection of a second signal greater than the first signal indicates control IHC staining of the antigen. In some embodiments, the detectable moiety comprises an enzyme, and wherein detecting the signal of the detectable moiety comprises exposing the detectable moiety to a chromogenic, fluorescent or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle). In some embodiments, the first concentration is OnM, and wherein detection of a lack of a first signal indicates control IHC staining of the antigen. In some embodiments, the methods further comprise: providing a sample; contacting the sample with the primary antibody; after contacting the sample with the primary antibody, contacting the sample with the secondary antibody; detecting a third signal of the detectable moiety from the sample; and comparing the third signal with the first and the second signals, wherein an amount of the third signal relative to the amounts of the first and the second signals indicates an abundance of the antigen in the sample, relative to the amounts of the antigen in the first and the second solid antigen/carrier protein gels.

Certain aspects of the present disclosure relate to methods for control immunohistochemical (IHC) staining with a secondary antibody, comprising: providing a first and a second solid antigen/carrier protein gel according to any one of the above embodiments, wherein the first solid antigen/carrier protein gel comprises a first antibody having a first isotype, and wherein the second solid antigen/carrier protein gel comprises a second antibody having a second isotype different from the first isotype; contacting the first and the second solid antigen/carrier protein gels with a secondary antibody that specifically binds the first isotype, wherein a detectable moiety is conjugated to the secondary antibody; detecting a signal of the detectable moiety from the first solid antigen/carrier protein gel; and detecting a lack of the signal of the detectable moiety from the second solid antigen/carrier protein gel, wherein detection of the signal associated with the first solid antigen/carrier protein gel and the lack of the signal associated with the second solid antigen/carrier protein gel indicates control staining with the secondary antibody. In some embodiments, the detectable moiety comprises an enzyme, and wherein detecting the signal of the detectable moiety comprises exposing the detectable moiety to a chromogenic, fluorescent or chemiluminescent substrate of the enzyme and detecting a signal from the substrate upon reaction with the enzyme. In some embodiments, the detectable moiety comprises a fluorophore, metal particle, metal ion, radioisotope, nucleic acid, electrochemiluminescent reporter, or a "quantum dot" (a solid state, semiconductor or carbon-based fluorescent nanoparticle).

Certain aspects of the present disclosure relate to kits (e.g., for control immunohistochemical (IHC) staining of an antigen) comprising: a first solid gel comprising a purified antigen cross-linked to a carrier protein selected from the group consisting of an albumin protein (e.g., a serum albumin protein), an egg white protein or a mixture of egg white proteins, and gelatin, wherein the purified antigen is present in the first solid gel at a first concentration; and a second solid gel comprising the purified antigen cross-linked to the carrier protein, wherein the purified antigen is present in the second solid gel at a second concentration different from the first concentration. In some embodiments, the kits comprise: a first solid gel comprising a purified antigen cross-linked to a carrier protein selected from the group consisting of an albumin protein (e.g., a serum albumin protein), an egg white protein or a mixture of egg white proteins, gelatin, and poly-lysine, wherein the purified antigen is present in the first solid gel at a first concentration; and a second solid gel comprising the purified antigen cross-linked to the carrier protein, wherein the purified antigen is present in the second solid gel at a second concentration different from the first concentration. In some embodiments, the first and the second solid gels are each sectioned into a thickness of between about 30 nm and about 50 µm. In some embodiments, the first and the second solid gels are affixed to one or more solid substrates. In some embodiments, the kits further comprise: a third solid gel comprising the carrier protein, wherein the third solid gel does not comprise the purified antigen. In some embodiments, the third solid gel is sectioned into a thickness of between about 30 nm and about 50 µm. In some embodiments, the third solid gel is affixed to a solid substrate.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3D shows the red fluorescence of the reporter. FIG. 3E shows fluorescence of the same TMA imaged in the DAPI filter channel (detects blue autofluorescence in the BSA cores).

FIG. 3F shows the fluorescence of the reporter.

FIG. 3G shows fluorescence of the same TMA imaged in the DAPI filter channel (detects autofluorescence in the BSA cores).

FIG. 4A shows control IHC staining using a donkey anti-mouse secondary antibody on BSA gel sections containing mouse IgG (left) or rat IgG (right).

FIG. 4B shows control IHC staining using a donkey anti-rat secondary antibody on BSA gel sections containing mouse IgG (left) or rat IgG (right).

Figure 5C:
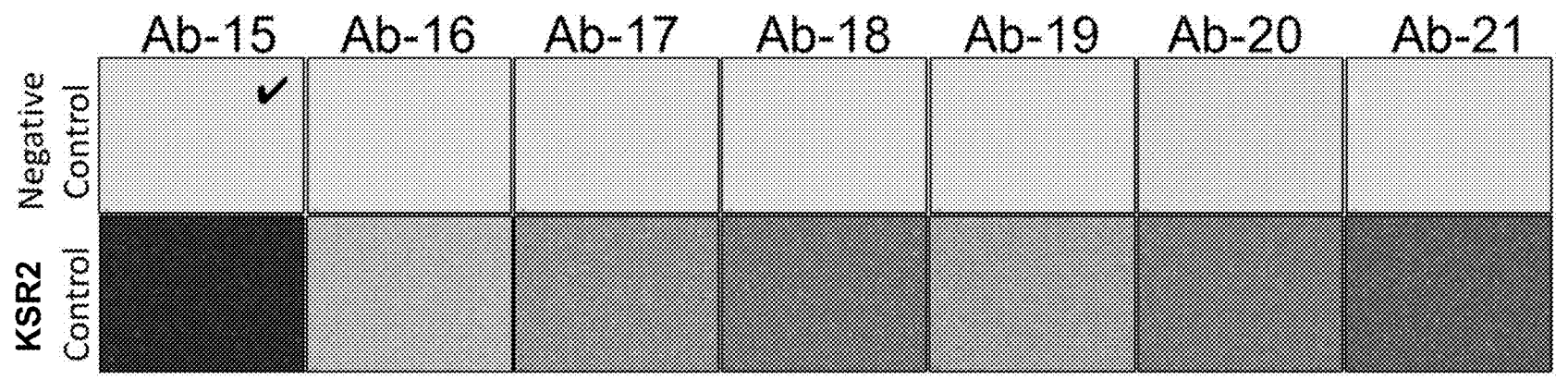

FIGS. 5A-5D show the results of screening twenty-seven different antibodies obtained from mice immunized with human KSR2 by IHC using protein/BSA gels (as compared to staining with naïve mouse IgG in FIG. 5D). Top row of each shows the results of IHC staining using each antibody on BSA gels without protein. Bottom row shows the results of IHC staining using each antibody on BSA gels embedded with the human KSR2 protein used to immunize the mice. The mouse antibody clone is indicated for each respective column. Check marks indicate highest performing clones, as evidenced by strong signal in the target protein sample (lower row) together with minimal signal in the negative control sample (upper row).

FIG. 6 shows the results of evaluating the effects of temperature and heating time on BSA gel formation. Temperature indicates temperature at which the liquid 25% BSA solution was heated. Time indicates duration for which the BSA solution was heated and then tested for solid/liquid phase before being cooled to room temperature. S=solid; L=liquid; semi-S=semi-solid.

FIG. 7 shows the results of evaluating the effects of time, temperature, and BSA concentration on BSA gel formation. Temperature indicates temperature at which the liquid BSA solution was heated. Time indicates duration for which the BSA solution was heated and then tested for solid/liquid phase before being cooled to room temperature. Percentage indicates concentration of BSA in BSA/PBS liquid solution. S=solid; L=liquid; o/n=overnight.

FIGS. 11A-11D show the results of two separate experiments using chromogenic assays to examine antigen distribution in gels. Four micron-thick "donor block" sections of BSA gel containing $5 \times 10^{-5}$M BCL2 peptide (upper rows in FIGS. 11A & 11C) or no peptide (lower rows in FIGS. 11A & 11C) were stained with anti-BCL2 clone 124 in two separate experiments (Experiment 1: left columns in FIGS. 11A & 11C; Experiment 2: right columns in FIGS. 11A & 11C). Digital images of the stained sections were quantified along the horizontal (FIG. 11A) and vertical (FIG. 11C) axes using the Plot Profile function in ImageJ. Results are shown in (FIG. 11B) and (FIG. 11D), respectively. Experiments 1 and 2 are indicated in black and gray, respectively. Data for BCL2 peptide- and BSA-only control sections are indicated in solid and dashed lines, respectively.

FIGS. 12A-12E show the results of IHC analysis of BCL2 using a BCL2 peptide TMA. (FIG. 12A) A tissue microarray section stained with anti-BCL2 clone 124 includes duplicate TMA cores containing no added peptide (BSA), a dilution series of peptide encoding amino acids 41-54 of the BCL2 protein, or a negative control peptide from the human MCL1 protein in the concentrations indicated. The images of BCL2 and MCL1 rows are different fields of view from the same TMA section. TMA cores are 1 mm in diameter. A serial section from the same TMA described in (FIG. 12A) is stained with anti-BCL2 clone 124 using immunofluorescent detection (FIG. 12B) or with anti-BCL2 clone EPR17509 using chromogenic detection (FIG. 12C). (FIG. 12D) Quantification of signal in individual cores containing BCL2 peptide (circles) or MCL1 peptide (squares), as illustrated in FIGS. 12A-12C. (FIG. 12E) The relevant parameters for the curves illustrated in (FIG. 12D). The HillSlope parameter conveys the steepness of the curve. ACHM is the antigen concentration at half-maximum signal.

FIGS. 14A-14C show the reproducibility of replicate sections. (FIG. 14A) Images from six serial sections of a single tissue microarray containing duplicate TMA cores having no added peptide (BSA), or peptide encoding amino acids 41-54 of the BCL2 protein. Each slide was stained for BCL2 using clone 124 on six different days by two operators. Operator 1 stained run 1; operator 2 stained runs 2-6. (FIG. 14B) Quantification of the images illustrated in FIG. 14A. The average signal from duplicate cores at each peptide concentration on each of the six TMA are shown. (FIG. 14C) The table summarizes the relevant parameters for the curves illustrated in FIG. 14B.

FIGS. 15A-15C show IHC staining for BCL2 peptide with and without antigen retrieval. (FIG. 15A) TMA contained BSA gel cores having no added peptide (BSA), or peptides encoding amino acids 41-54 of the BCL2 protein at the indicated concentrations. Sections were stained with (AR) or without (No AR) prior antigen retrieval. (FIG. 15B) Quantification of the images illustrated in FIG. 15A. Solid squares: with antigen retrieval; open squares: without antigen retrieval. The average signals from duplicate cores at each peptide concentration are shown. (FIG. 15C) The table summarizes the relevant parameters for the curves illustrated in FIG. 15B.

FIGS. 16A-16C show that alternative BCL2 peptide N- and C-termini affect signal strength. (FIG. 16A) Images from a single TMA section containing duplicate BSA gel cores having no added peptide (BSA) or 22-amino acid peptides encoding amino acids 41-54 of the BCL2 protein (rows I-V) flanked by the three amino acid sequence, GSG, with alternative N- and C-terminal amino acids (acetyl-N, C-amide) as indicated. (FIG. 16B) Quantification of the images illustrated in FIG. 16A. The average signal from duplicate cores at each peptide concentration are shown. (FIG. 16C) The table summarizes the relevant parameters for the curves illustrated in FIG. 16B.

FIGS. 17A-17E show IHC staining of BCL2 and MYC peptides. (FIG. 17A) Sections of donor blocks containing $2.5 \times 10^{-4}$ M peptides from human MYC as indicated. The scale bar is 1 mm. (FIGS. 17B & 17C) A single TMA section stained with anti-BCL2 clone 124 (FIG. 17B) or anti-MYC clone Y69 (FIG. 17C) includes duplicate cores formulated to contain no peptide (BSA), or peptides encoding BCL2 amino acids 41-54 and MYC amino acids 9-24. (FIG. 17D) Quantification of the images illustrated in FIGS. 17B & 17C. The average signals from duplicate cores at each peptide concentration are shown. (FIG. 17E) The relevant parameters for the curves illustrated in FIG. 17D.

FIGS. 18A-18C show dual MYC/BCL2 immunofluorescence (IF) image analysis. (FIG. 18A) A single section from a TMA that included cores with no peptide (BSA), or with peptidec encoding BCL2 amino acids 41-54 and MYC amino acids 9-24 at the indicated concentrations. The section was stained sequentially with both anti-BCL2 clone 124 and anti-MYC clone Y69, detected with Ventana Discovery FAM (BCL2; green) or Discovery Cy5 (MYC; red) kits, then imaged in the appropriate wavelengths for each fluorochrome. (FIG. 18B) Quantification of the images illustrated in FIG. 18A. The average signals from duplicate cores at each peptide concentration are shown. Error bars indicate ±1 standard deviation. (FIG. 18C) The table summarizes the relevant parameters for the curves illustrated in FIG. 18B.

FIGS. 19A & 19B show aggregate anti-BCL2 clone 124 data. (FIG. 19A) Data from FIGS. 12A-12E & 14A-17E (n=10 independent IHC assays, each with duplicate cores at each peptide concentration) were grouped and plotted. Error bars represent 1 standard deviation (n=10). (FIG. 19B) The relevant parameters for the data in FIG. 19A.

FIG. 20B provides quantification of the results shown in FIG. 20A.

(FIG. 21A) Serial sections of a TMA composed of duplicate BSA gel cores containing either naive rabbit, rat or mouse IgG (0.1 milligrams/ml; $6.7 \times 10^{-7}$ M) were stained with donkey secondary antibodies specific to IgG from the indicated species. TMA cores are 1 mm in diameter. (FIG. 21B) Quantification of images illustrated in FIG. 21A: rabbit IgG antigen (solid bars); rat IgG (hashed bars); mouse IgG (open bars). For each species-specific antibody, signal in cores containing the target IgG was significantly higher than for cores containing the non-target IgGs (p<0.0001). Error bars are 1 SD. Note that these data are also shown in FIG. 3C.

FIGS. 22A-22C show the results of generating peptide gels using alternative fixatives. (FIG. 22A) Donor cores were prepared with BCL2 or MYC peptide by heating 10 min at 85 C in the presence of 18.5% formaldehyde or 50% zinc fixative. Donor blocks were formulated to contain either no peptide (BSA), or peptides encoding BCL2 amino acids 41-54 and MYC amino acids 9-24. Sections were stained with anti-BCL2 clone 124 or anti-MYC clone Y69 as appropriate. (FIG. 22B) Quantification of the images illustrated in FIG. 22A. (FIG. 22C) The relevant parameters for the curves illustrated in FIG. 22B.

(FIG. 23A) BSA gels containing BCL2 peptide were prepared by heating to 85 C in the presence of zinc-containing fixative (Zn & Heat) or concentrated formaldehyde (37% Form. & Heat), or heated to 85 C in the absence of fixative, then fixed at room temperature in zinc-containing fixative (Heat, Zn), 4% PFA (Heat, 4% PFA), or neutral-buffered formalin (Heat, NBF). (FIG. 23B) Quantification of images in FIG. 23A.

FIGS. 24A-24C show imaging mass cytometric analysis of BCL2 peptide TMA. (FIG. 24A) Representative fields of view (approx. 150 microns square) of TMA sections stained with anti-BCL2 clone EPR17509 conjugated to a $^{146}$Nd mass spectrometry tag and imaged in a Fluidigm Hyperion scanning mass spectrometer. Duplicate TMA cores contained no added peptide (BSA), peptide encoding amino acids 41-54 of the BCL2 protein, or a negative control peptide from the human MCL1 protein in the concentrations indicated. (FIG. 24B) Quantification of the images illustrated in FIG. 24A. Error bars indicate 1 standard deviation. (FIG. 24C) The table summarizes the relevant parameters for the curves illustrated in FIG. 24B. The HillSlope parameter conveys the steepness of the curve. ACHM is the antigen concentration at half-maximum signal.

DETAILED DESCRIPTION

I. Definitions

Figure 1:
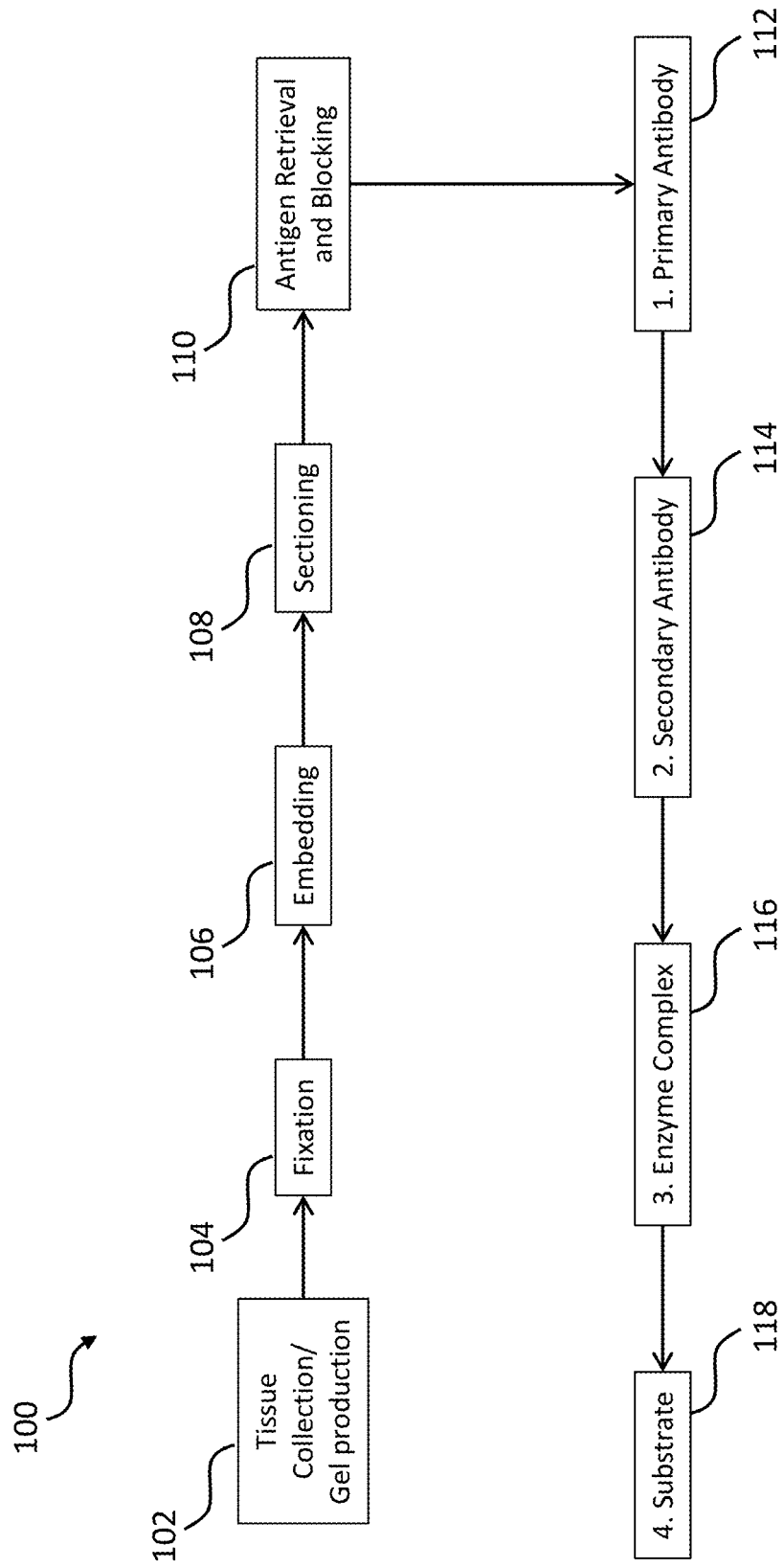
FIG. 1 shows an exemplary workflow for IHC staining using slides obtained from tissue samples.

All patents, applications, published applications and other publications are incorporated by reference in their entirety. Unless defined otherwise, all technical and scientific terms used herein have the same meaning as commonly understood by those of ordinary skill in the art to which the invention belongs.

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "antigen" herein is used in the broadest sense and encompasses various forms of both polypeptide and non-polypeptide antigens, including, without limitation, small peptide antigens, full-length protein antigens, carbohydrate antigens, lipid antigens, and nucleic acid antigens.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "immunoglobulin" (Ig) is used interchangeable with antibody herein.

A "purified" antigen refers to an antigen has been increased in purity, such that it exists in a form that is more pure than it exists in its natural environment and/or when initially produced and/or synthesized and/or amplified under laboratory conditions. Purity is a relative term and does not necessarily mean absolute purity. In some embodiments, the antigen is purified to at least 90%, at least 95%, or at least 99% purity.

II. Solid Antigen/Carrier Protein Gels and Methods of Production

Certain aspects of the present disclosure relate to solid antigen/carrier protein gels, as well as methods for generating a solid antigen/carrier protein gel.

In some embodiments, the present disclosure provides a solid antigen/carrier protein gel comprising a purified antigen and a carrier protein. In some embodiments, the carrier protein is selected from an albumin protein (e.g., a serum albumin protein), an egg white protein or a mixture of egg white proteins, gelatin, and poly-lysine. In some embodiments, the purified antigen is cross-linked to the carrier protein. As described below, these gels may find use, e.g., as a control for IHC staining or EM imaging analyses.

The present disclosure demonstrates that multiple types of carrier proteins can be used in a solid antigen/carrier protein gel. In some embodiments, the carrier protein is an albumin protein. In some embodiments, the carrier protein is a serum albumin protein. In some embodiments, the serum albumin protein is a mammalian serum albumin protein. Examples of serum albumin proteins include, without limitation, mouse, rat, Guinea pig, rabbit, porcine, bovine, goat, sheep, horse, and human serum albumin. In some embodiments, the carrier protein is an egg white protein. In some embodiments, the carrier protein is a mixture of two or more egg white proteins. In some embodiments, the carrier protein is gelatin. In some embodiments, the carrier protein is poly-lysine.

In some embodiments, the solid antigen/carrier protein gel comprises the carrier protein at a concentration of greater than or equal to 0.5%, 1%, 2%, 5%, 7%, 10%, 15%, or 20% (w/v). In some embodiments, the solid antigen/carrier protein gel comprises the carrier protein at a concentration of less than or equal to 25%, 20%, 15%, 10%, 7%, 5%, 2%, or 1% (w/v). That is, the solid antigen/carrier protein gel can comprise the carrier protein at any concentration of a range of concentrations having an upper limit of 25%, 20%, 15%, 10%, 7%, 5%, 2%, or 1% (w/v) and an independently selected lower limit of 0.5%, 1%, 2%, 5%, 7%, 10%, 15%, or 20% (w/v), wherein the lower limit is less than the upper limit. In some embodiments, the carrier protein comprises an albumin protein (e.g., a serum albumin protein), and the solid antigen/carrier protein gel comprises the carrier protein at greater than 2% (w/v), e.g., between 2% and 25% (w/v). In some embodiments, the carrier protein comprises an egg white protein or mixture of egg white proteins, and the solid antigen/carrier protein gel comprises the carrier protein at greater than 2% (w/v), e.g., between 2% and 25% (w/v). In some embodiments, the carrier protein comprises gelatin, and the solid antigen/carrier protein gel comprises the carrier protein at greater than 0.5% (w/v), e.g., between 0.5% and 25% (w/v) or about 10% (w/v).

In some embodiments, the solid antigen/carrier protein gel contains the antigen at a concentration of at least about 25 nM. In another embodiment, the solid antigen/carrier protein gel contains the antigen at a concentration of about 25 nM. In yet another embodiment, the solid antigen/carrier protein gel contains the antigen at a concentration of about 15, 20, 25, 30, 35, 40, 50, 60, 75, 80, 90, or 100 nM, or more. In another embodiment, the solid antigen/carrier protein gel contains the antigen at a concentration of at least about: 10 nM, 15 nM, 20 nM, or 25 nM to about 100 nM. As described herein, a solid antigen/carrier protein gel of the present disclosure can comprise the antigen at a wide range of concentrations, depending, e.g., upon the sensitivity of the detection method, desired application of the gel, and so forth.

In one embodiment, the methods include two or more antigen/carrier protein gels. In one embodiment, two gels are used where each gel optionally has a different concentration of antigen. In another embodiment, three gels are used where each gel optionally has a different concentration of antigen. Indeed, multiple gels comprising an antigen at different concentrations may be useful, e.g., as a control for IHC staining to represent a range of antigen concentrations.

In some embodiments, the antigen comprises a polypeptide antigen (e.g., a peptide antigen or full-length protein antigen). In some embodiments, the polypeptide antigen comprises an N-terminal tyrosine, a C-terminal cysteine, or both (e.g., for chemical cross-linking the antigen to a carrier protein). In some embodiments, the N-terminal tyrosine and/or C-terminal cysteine is cross-linked to the carrier protein. For example, a C-terminal cysteine may be used to cross-link the antigen with the carrier protein. A variety of cysteine-reactive reagents are known in the art and include, without limitation, sulfhydryl-reactive crosslinker reactive groups such as haloacetyls, maleimides (e.g., sulfo-SMCC and its analogs), aziridines, acryloyls, arylating agents, vinylsulfones, pyridyl disulfides, TNB-thiols, and disulfide reducing agents.

In some embodiments, the solid antigen/carrier protein gel has been fixed with a fixative, e.g., as described below. In embodiments, the fixative is a cross-linking fixative (e.g., an aldehyde-based fixative). In some embodiments, the fixative is not a cross-linking fixative (e.g., a precipitating fixative, such as Carnoy's). As described herein, a solid gel containing a carrier protein and an antigen may be prepared by denaturing and precipitating the carrier protein and/or the antigen by heating, or by adding a precipitating fixative to the mixture, causing the antigen to be immobilized in the protein gel. For some antigens (particularly those of small molecular size), cross-linking the antigen to the carrier protein (either during or after the process of forming a gel by denaturing the carrier protein) is thought to help to retain the antigen in the gel and in the resulting sections, e.g., during the embedding, sectioning, and/or staining processes.

In some embodiments, the antigen comprises a non-polypeptide antigen. Examples of non-polypeptide antigens include, without limitation, carbohydrates, lipids, and nucleic acids.

In some embodiments, the solid antigen/carrier protein gel has a thickness of between about 30 nm and about 50 µm. A suitable thickness for the solid antigen/carrier protein gel may depend, e.g., upon the application. In some embodiments, the solid antigen/carrier protein gel has a thickness of greater than or equal to about 0.03, 1, 2, 4, 6, 8, 10, 12, 14, 16, 18, 20, 22, 24, 26, 28, 30, 32, 34, 36, 38, 40, 42, 44, 46, or 48 µm. In some embodiments, the solid antigen/carrier protein gel has a thickness of less than or equal to about 50, 48, 46, 44, 42, 40, 38, 36, 34, 32, 30, 28, 26, 24, 22, 20, 18, 16, 14, 12, 10, 8, 6, 4, 2, or 1 µm. That is, the solid antigen/carrier protein gel can have a thickness having an upper limit of 50, 48, 46, 44, 42, 40, 38, 36, 34, 32, 30, 28, 26, 24, 22, 20, 18, 16, 14, 12, 10, 8, 6, 4, 2, or 1 µm and an independently selected lower limit of 0.03, 1, 2, 4, 6, 8, 10, 12, 14, 16, 18, 20, 22, 24, 26, 28, 30, 32, 34, 36, 38, 40, 42, 44, 46, or 48 µm, wherein the lower limit is less than the upper limit. For example, a solid antigen/carrier protein gel used for IHC staining may have a thickness, e.g., of between about 2 µm and about 30 µm, whereas a solid antigen/carrier protein gel used for EM may have a thickness, e.g., of between about 30 nm and about 50 µm or between about 30 nm and about 100 nm. Methods for sectioning a solid antigen/carrier protein gel of the present disclosure are described below.

In some embodiments, the solid antigen/carrier protein gel has been subjected to antigen retrieval. Exemplary methods for antigen retrieval are described in greater detail below.

In some embodiments, the solid antigen/carrier protein gel is embedded in a medium of the present disclosure, such as paraffin (e.g., embedding in a paraffin block); epoxy, acrylic, or plastic resin (e.g., EPON™ resins, methacrylate, LR White resin, Araldite®, Spurr plastic, LOWICRYL®, and the like); synthetic wax; blends of paraffin wax and plastic polymer or co-polymer alloys; polyethylene glycol; or GACH embedding medium (Glutaraldehyde-Carbohydrazide). In some embodiments, the solid antigen/carrier protein gel is affixed to a solid substrate, including without limitation a glass slide (e.g., for IHC), support, grid, or stub (e.g., for EM).

In some embodiments, a method for generating a solid antigen/carrier protein gel comprises mixing a purified antigen with a liquid solution comprising a carrier protein to produce an antigen/carrier protein liquid solution and heating the antigen/carrier protein liquid solution to form the solid antigen/carrier protein gel. In some embodiments, the carrier protein is selected from an albumin protein (e.g., a serum albumin protein), an egg white protein or a mixture of egg white proteins, and gelatin.

In some embodiments, the antigen/carrier protein liquid solution comprises the carrier protein at a concentration of greater than or equal to 0.5%, 1%, 2%, 5%, 7%, 10%, 15%, or 20% (w/v). In some embodiments, the antigen/carrier protein liquid solution comprises the carrier protein at a concentration of less than or equal to 25%, 20%, 15%, 10%, 7%, 5%, 2%, or 1% (w/v). That is, the antigen/carrier protein liquid solution can comprise the carrier protein at any concentration of a range of concentrations having an upper limit of 25%, 20%, 15%, 10%, 7%, 5%, 2%, or 1% (w/v) and an independently selected lower limit of 0.5%, 1%, 2%, 5%, 7%, 10%, 15%, or 20% (w/v), wherein the lower limit is less than the upper limit. In some embodiments, the carrier protein comprises an albumin protein (e.g., a serum albumin protein), and the antigen/carrier protein liquid solution comprises the carrier protein at greater than 2% (w/v), e.g., between 2% and 25% (w/v). In some embodiments, the carrier protein comprises an egg white protein or a mixture of egg white proteins, and the antigen/carrier protein liquid solution comprises the carrier protein at greater than 2% (w/v), e.g., between 2% and 25% (w/v). In some embodiments, the carrier protein comprises gelatin, and the antigen/carrier protein liquid solution comprises the carrier protein at greater than 0.5% (w/v), e.g., between 0.5% and 25% (w/v) or about 10% (w/v).

In some embodiments, the methods of the present disclosure include (e.g., prior to heating the antigen/carrier protein liquid solution) cross-linking the antigen with the carrier protein using a cysteine-reactive reagent. A variety of cysteine-reactive reagents are known in the art and include, without limitation, sulfhydryl-reactive crosslinker reactive groups such as haloacetyls, maleimides (e.g., sulfo-SMCC and its analogs), aziridines, acryloyls, arylating agents, vinylsulfones, pyridyl disulfides, TNB-thiols, and disulfide reducing agents.

In some embodiments, the methods of the present disclosure include fixing the antigen with the carrier protein. In some embodiments, a fixative is included in the antigen/carrier protein liquid solution. In some embodiments, the fixative is a cross-linking fixative. In some embodiments, the fixative is a non-cross-linking fixative. Examples of suitable fixatives include, without limitation, formaldehyde, formalin, paraformaldehyde (PFA), glutaraldehyde, Davidson's fixative, Bouin's fixative, Karnovski's fixative (e.g., ½ strength Karnovski's fixative), Zenker's solution, Helly's solution, Carnoy's solution, Zinc formalin, neutral-buffered formalin (NBF), Periodate-Lysine-paraformaldehyde (PLP), Zamboni's fixative, dimethyl suberimidate (DMS), acetone, alcohols (e.g., methanol or ethanol), and zinc salts (e.g., zinc acetate, zinc chloride, zinc trifluoroactetate, etc.). In certain embodiments, the fixative comprises formaldehyde (e.g., at a concentration of at least about 1% or at least about 2%).

In some embodiments, the antigen is cross-linked with the carrier protein using selective chemistry, including without limitation azide-alkyne addition. In some embodiments, selective chemistry is used to cross-link a non-protein antigen to the carrier protein, e.g., a carbohydrate or lipid antigen.

In some embodiments, the methods of the present disclosure include dehydrating the solid antigen/carrier protein gel. Compounds suitable for dehydrating are known in the art and can include, e.g., alcohols such as ethanol or methanol. In some embodiments, the methods of the present disclosure include embedding the solid antigen/carrier protein gel. In some embodiments, the solid antigen/carrier protein gel is embedded after dehydration. For example, in some embodiments, the solid antigen/carrier protein gel is dehydrated by exposure to a sequence of increasing or graded alcohols (e.g., a sequence of increasing ethanol concentrations), followed by exchange of alcohols with xylene, and exchange of xylene with paraffin. A variety of media are known in the art and can be used for embedding, including without limitation paraffin (e.g., embedding in a paraffin block); epoxy, acrylic, or plastic resin (e.g., EPON™ resins, methacrylate, LR White resin, Araldite®, Spurr plastic, LOWICRYL®, and the like); synthetic wax; blends of paraffin wax and plastic polymer or co-polymer alloys; polyethylene glycol; and GACH embedding medium (Glutaraldehyde-Carbohydrazide).

In some embodiments, the carrier protein comprises gelatin, and the methods of the present disclosure include cooling a heated antigen/carrier protein liquid solution to form the solid antigen/carrier protein gel. In some embodiments, the methods further include incubating the solid antigen/carrier protein gel with a fixative and dehydrating the solid antigen/carrier protein gel. In some embodiments, the antigen/carrier protein liquid solution comprises the carrier protein at a concentration of greater than or equal to about 0.5% (w/v). In some embodiments, the antigen/carrier protein liquid solution is heated to at least about 65° C. (e.g., for at least about 6 minutes).

In some embodiments, the carrier protein comprises polylysine, e.g., at a concentration of about 14 mg/mL.

In some embodiments, the methods of the present disclosure include incubating the solid antigen/carrier protein gel in an embedding medium (e.g., a liquid embedding medium). A variety of embedding media are known in the art and can include, without limitation, Optimum Cutting Temperature (OCT) Compound (e.g., Tissue-Tek® O.C.T. Compound or Tissue-plus® O.C.T Compound), PELCO® Cryo-Embedding Compound, PolarStat™ or PolarStat Plus™ Embedding Medium, and Tissue Freezing Medium or TFM™. These embedding media can contain, e.g., water-soluble glycols and resins; the exemplary embedding media OCT Compound includes 5-15% polyvinyl alcohol and 1-10% polyethylene glycol. In some embodiments, the methods of the present disclosure include freezing the solid antigen/carrier protein gel (e.g., after incubating the solid antigen/carrier protein gel in an embedding medium). In some embodiments, the methods of the present disclosure include freezing a solid antigen/carrier protein gel that has not been fixed (e.g., that does not include a fixative), similar to the preparation of frozen, unfixed fresh tissue samples.

In some embodiments, the methods of the present disclosure include sectioning the solid antigen/carrier protein gel into one or more solid antigen/carrier protein gel sections. In some embodiments, the one or more solid antigen/carrier protein gel sections have a thickness of between about 30 nm and about 50 μm. In some embodiments, the one or more solid antigen/carrier protein gel sections have a thickness of greater than or equal to about 0.03, 0.05, 0.1, 0.2, 0.3, 0.4, 0.5, 0.6, 0.7, 0.8, 0.9, 1, 2, 4, 6, 8, 10, 12, 14, 16, 18, 20, 22, 24, 26, 28, 30, 32, 34, 36, 38, 40, 42, 44, 46, or 48 μm. In some embodiments, the one or more solid antigen/carrier protein gel sections have a thickness of less than or equal to about 50, 48, 46, 44, 42, 40, 38, 36, 34, 32, 30, 28, 26, 24, 22, 20, 18, 16, 14, 12, 10, 8, 6, 4, 2, 1, 0.9, 0.8, 0.7, 0.6, 0.5, 0.4, 0.3, 0.2, or 0.1 μm. That is, the one or more solid antigen/carrier protein gel sections can have a thickness having an upper limit of 50, 48, 46, 44, 42, 40, 38, 36, 34, 32, 30, 28, 26, 24, 22, 20, 18, 16, 14, 12, 10, 8, 6, 4, 2, 1, 0.9, 0.8, 0.7, 0.6, 0.5, 0.4, 0.3, 0.2, or 0.1 μm and an independently selected lower limit of 0.03, 0.05, 0.1, 0.2, 0.3, 0.4, 0.5, 0.6, 0.7, 0.8, 0.9, 1, 2, 4, 6, 8, 10, 12, 14, 16, 18, 20, 22, 24, 26, 28, 30, 32, 34, 36, 38, 40, 42, 44, 46, or 48 μm, wherein the lower limit is less than the upper limit. For example, a solid antigen/carrier protein gel section used for IHC staining may have a thickness, e.g., of between about 2 μm and about 30 μm, whereas a solid antigen/carrier protein gel section used for EM may have a thickness, e.g., of between about 30 nm and about 50 μm or between about 30 nm and about 100 nm. Instruments for sectioning a solid antigen/carrier protein gel of the present disclosure are known in the art and can include, without limitation, a microtome, cryostat (for frozen gels), knife (e.g., diamond, glass, or sapphire), and the like. In some embodiments, the solid antigen/carrier protein gel is dehydrated, embedded, fixed, frozen, or a combination thereof prior to sectioning.

In some embodiments, the methods of the present disclosure include subjecting the solid antigen/carrier protein gel to antigen retrieval. A variety of antigen retrieval methods are known in the art. In some embodiments, subjecting the solid antigen/carrier protein gel to antigen retrieval comprises heating the solid antigen/carrier protein gel in a liquid solution (e.g., heat-induced epitope retrieval), such as by boiling. In some embodiments, the liquid solution comprises a buffer, such as Tris/EDTA or sodium citrate buffer. In some embodiments, subjecting the solid antigen/carrier protein gel to antigen retrieval comprises treatment with one or more proteolytic enzymes (e.g., trypsin, proteinase K, pepsin, ficin, or pronase) or antigen retrieval reagents (e.g., hydrochloric acid, formic acid, sodium dodecyl sulfate (SDS), citrate buffer, EDTA, citrate-EDTA, Tris, Tris-EDTA, Tris-HCl, Tris-buffered saline, or citraconic anhydride). For additional descriptions of antigen retrieval, see, e.g., Shi, S. R. et al. (2011) *J. Histochem. Cytochem.* 59:13-32.

In some embodiments, the methods of the present disclosure include blocking a solid antigen/carrier protein gel. As is known in the art, blocking (e.g., prior to IHC staining) reduces non-specific interactions with antigens by preventing binding to sites not related to specific antigen:antibody interactions. A variety of suitable blocking reagents are known in the art and can include, without limitation, serum or a protein solution (e.g., comprising a serum albumin protein, gelatin, non-fat dry milk, or the like).

In some embodiments, the methods of the present disclosure include fixing a solid antigen/carrier protein gel (e.g., by including a fixative in the antigen/carrier protein liquid solution), dehydrating the solid antigen/carrier protein gel, embedding the dehydrated solid antigen/carrier protein gel, sectioning the paraffin block with the embedded solid antigen/carrier protein gel into one or more sections, subjecting the one or more sections to antigen retrieval, and blocking the one or more sections after antigen retrieval. In other embodiments, the methods of the present disclosure include incubating the solid antigen/carrier protein gel in a liquid embedding medium, freezing the solid antigen/carrier protein gel in the embedding medium, sectioning the frozen antigen/carrier protein gel into one or more sections, and blocking the one or more sections.

Other aspects of the present disclosure relate to tissue microarrays (TMAs) comprising one, two, or more solid antigen/carrier protein gel(s) of the present disclosure. For example, a TMA of the present disclosure may be prepared by preparing a solid antigen/carrier protein gel of the present disclosure (e.g., embedded in a paraffin block as described above), punching a core comprising the solid antigen/carrier protein gel, and transferring the core to a recipient TMA. In some embodiments, the core has a diameter of about 1 mm. An exemplary method for preparing a TMA is described infra, e.g., by transferring core(s) from a donor paraffin block to a recipient TMA block, then heating (e.g., at 37 C overnight, then 70 C for 10 minutes), cooling, and sectioning the recipient TMA block. In some embodiments, the TMAs include two or more solid antigen/carrier protein gels of the present disclosure with different antigens. In some embodiments, the TMAs include two or more solid antigen/carrier protein gels of the present disclosure with the same antigen at different concentrations. In some embodiments, the TMA further comprises one or more orientation reference(s), e.g., comprising a colored pigment for identification. In some embodiments, the TMA is a TMA section on a histology slide. Without wishing to be bound by theory, it is thought that solid antigen/carrier protein gels of the present disclosure are particularly advantageous for use in TMAs, e.g., for providing a range of epitope concentrations and/or types. This range can also be provided adjacent to a tissue section, thereby allowing a convenient reference for quantitative analyses.

III. Uses for Solid Antigen/Carrier Protein Gels

Solid antigen/carrier protein gels (e.g., as described in section II above and/or exemplified in the Examples below) may find use in a variety of applications, including but not limited to controls for IHC or EM analysis.

In some embodiments, a method for control immunohistochemical (IHC) staining of an antigen comprises providing multiple solid antigen/carrier protein gels of the present disclosure (e.g., two or more, three or more, four or more, five or more, etc.) representing different concentrations of an antigen of interest. For example, the methods can include providing two solid antigen/carrier protein gels made with different concentrations of a purified antigen. In some embodiments, the methods include contacting the solid antigen/carrier protein gels with a primary antibody that specifically binds the antigen and is coupled to a detectable moiety. In other embodiments, the methods include contacting the solid antigen/carrier protein gels with a primary antibody that specifically binds the antigen, then contacting the solid antigen/carrier protein gels with a secondary antibody that specifically binds the primary antigen and is coupled to a detectable moiety. In some embodiments, the methods further include detecting signal(s) of the detectable moiety from one or more of the multiple solid antigen/carrier protein gels. Amount of signal detected from the multiple solid antigen/carrier protein gels can then be detected and, optionally, compared against amount or concentration of antigen present in each of the multiple solid antigen/carrier protein gels to provide control IHC staining of the antigen at various levels.

In some embodiments, one of the antigen/carrier protein gels contains no antigen (e.g., 0 nM), and lack of a detectable signal from IHC staining of this gel indicates negative control or background IHC staining of the sample. In some embodiments, the methods further include contacting a sample with the primary antibody that specifically binds the antigen and is coupled to a detectable moiety, or with the primary antibody that specifically binds the antigen and the secondary antibody that specifically binds the primary antigen and is coupled to a detectable moiety, and detecting a signal of the detectable moiety from the sample. The amount of signal detected from the sample can then be compared against the amount of signal(s) detected from the solid antigen/carrier protein gel(s), e.g., to compare the amount of antigen present in the sample with known concentrations or amounts of antigen present in the solid antigen/carrier protein gel(s).

In some embodiments, a method for control immunohistochemical (IHC) staining with a secondary antibody comprises providing multiple solid antigen/carrier protein gels of the present disclosure (e.g., two or more, three or more, four or more, five or more, etc.) representing different antibody isotypes. For example, the methods can include providing two solid antigen/carrier protein gels made with antibodies representing different antibody isotypes. In some embodiments, the methods include contacting the solid antigen/carrier protein gels with a secondary antibody that specifically binds one of the antibody isotypes and is conjugated to a detectable moiety. For control staining of the secondary antibody, signal can be detected from the multiple solid antigen/carrier protein gels. In this example, the secondary antibody specifically binds the cognate antibody isotype, and any signal detected from a gel lacking the cognate antibody isotype indicates background staining. Thus, detection of the signal associated with the solid antigen/carrier protein gel containing the cognate antibody isotype and the lack of the signal associated with the solid antigen/carrier protein gel lacking the cognate antibody isotype indicates control staining with the secondary antibody.

In some embodiments, a method for immunohistochemical (IHC) staining of an antigen comprises providing one or more solid antigen/carrier protein gels containing the antigen and a sample; contacting the solid antigen/carrier protein gel and the sample with a primary antibody that specifically binds the antigen and is coupled to a detectable moiety, or contacting the solid antigen/carrier protein gel and the sample with a primary antibody that specifically binds the antigen and contacting the solid antigen/carrier protein gel and the sample with a secondary antibody that specifically binds the primary antibody and is coupled to a detectable moiety; detecting a signal of the detectable moiety from the solid antigen/carrier protein gel; and detecting a signal of the detectable moiety from the sample. Thus, the one or more solid antigen/carrier protein gels can be used as a positive control for IHC staining of the sample.

An exemplary flow diagram for process 100 for IHC staining of an antigen, such as an antigen in a sample and in a solid antigen/carrier protein gel of the present disclosure (used as a control for staining of the sample for the antigen) is shown in FIG. 1. At block 102, tissue is collected to provide a sample for analysis, and/or a solid antigen/carrier protein gel of the present disclosure is produced (e.g., as described in section II above). In some embodiments, the solid antigen/carrier protein gel contains an antigen (e.g., a purified antigen) of interest, which may or may not also be present in the sample. Optionally, at block 104, the sample and/or solid antigen/carrier protein gel is fixed (e.g., as described in section II above). In some embodiments, the solid antigen/carrier protein gel is incubated with a fixative. In other embodiments, the antigen/carrier protein liquid solution used to make the solid gel comprises a fixative. Optionally, at block 106, the sample and/or solid antigen/carrier protein gel are embedded (e.g., as described in section II above). As an optional alternative to block 104, at block 106, the sample and/or solid antigen/carrier protein gel can be frozen in an embedding medium. Optionally, at block 108, the sample and/or solid antigen/carrier protein gel are sectioned (e.g., as described in section II above). Optionally, at block 110, the sample and/or solid antigen/carrier protein gel are subjected to antigen retrieval and blocking (e.g., as described in section II above).

In some embodiments, as shown at block 112, the sample and the solid antigen/carrier protein gel are contacted with a primary antibody that specifically binds the antigen. In some embodiments, the primary antibody comprises a detectable moiety. In other embodiments, as shown at block 114, the sample and the solid antigen/carrier protein gel are contacted with a secondary antibody that specifically binds the primary antibody. In some embodiments, the secondary antibody comprises a detectable moiety conjugated to the secondary antibody (in this example, biotin).

In some embodiments, a signal of the detectable moiety is detected from the solid antigen/carrier protein gel and/or sample. As described below, a variety of detectable moieties are contemplated. In this example, a chromogenic detection method is used. At block 116, the sample and the solid antigen/carrier protein gel are contacted with an enzyme complex that binds to the secondary antibody (e.g., a streptavidin-conjugated enzyme complex that binds to a biotinylated secondary antibody). At block 118, the sample and the solid antigen/carrier protein gel are contacted with a chromogenic substrate or chromogen solution that, upon incubation with the enzyme complex, leads to formation of a colored precipitate indicating presence of the antigen in the solid antigen/carrier protein gel and, if the antigen is present, the sample.

In some embodiments, presence of an antigen in a solid antigen/carrier protein gel of the present disclosure is detected by direct detection, e.g., by incubation of the gel with an antibody or other antigen-binding moiety that specifically binds the antigen and is coupled to a detectable moiety. In other embodiments, presence of an antigen in a solid antigen/carrier protein gel of the present disclosure is detected by indirect detection, e.g., by incubation of the gel with a primary antibody or other antigen-binding moiety that specifically binds the antigen and a secondary antibody or other antigen-binding moiety that specifically binds the primary antibody or other antigen-binding moiety, where the secondary antibody or other antigen-binding moiety is coupled to a detectable moiety.

A variety of detectable moieties are contemplated for use with a solid antigen/carrier protein gel of the present disclosure. In some embodiments, the detectable moiety comprises an enzyme, e.g., horseradish peroxidase (HRP) or alkaline phosphatase (AP). Signal is then detected by exposing the detectable moiety to a chromogenic substrate of the enzyme and detecting a signal from the chromogenic substrate upon reaction with the enzyme (e.g., as described above for blocks 116 and 118). Examples of chromogenic substrates include, without limitation, 3,3'-diaminobenzidine (DAB), which is converted to a brown product by HRP; and 3-amino-9-ethylcarbazole (AEC), which is converted to a red product by AP. Alternatively, a peroxidase can chemically activate a tyramide moiety conjugated to one of several reporters (for example a fluorescent molecule); the activated tyramide conjugate can then covalently couple to nearby molecules in the sample, creating a detectable signal in the location of the peroxidase. Indirect detection can also be used with chromogenic staining. For example, a biotinylated secondary antibody can be incubated with an avidin- or streptavidin-labeled enzyme complex, a polymer such as a dextran can be coupled with one or more secondary antibodies and one or more enzyme complexes, or an enzyme complex can be polymerized directly onto a secondary antibody. In some embodiments, the detectable moiety comprises a fluorophore, such as Fluorescein (FITC), Rhodamine or its derivatives, TRITC, Cyanine (Cy3), Phycoerythrin (R-PE), and CF™, and so forth. For example, a fluorophore can be conjugated to the primary or secondary antibody, or conjugated to a tyramide moiety that can covalently couple to the sample after being activated by a peroxidase. In some embodiments, the detectable moiety comprises a metal particle, such as gold. For example, a gold particle can be conjugated to the primary or secondary antibody and imaged, e.g., by immuno-EM. In some embodiments, the detectable $125_k$ moiety comprises a radioisotope, such as $^{35}S$, $^{125}I$, or $^{131}I$ and imaged, e.g., by radioimmunodetection. For example, a radioisotope can be conjugated to the primary or secondary antibody. In some embodiments, the detectable moiety comprises a nucleic acid, such as DNA or RNA. For example, a nucleic acid can be conjugated to the primary or secondary antibody. A primary or secondary antibody can be coupled to a metal ion detectable with a mass spectrometer or mass cytometer [a la CYTOF and MIBI; see Giesen et al Nat Methods. 2014 April; 11(4):417-22 and Angelo et al, Nat Med. 2014 April; 20(4):436-42]. A primary or secondary antibody can be coupled to a solid state, semiconductor, or carbon-based nanoparticles (e.g "quantum dots") detectable by fluorescence imaging [see Wu et al, Nat Biotechnol. 2003 January; 21(1):41-6]. A primary or secondary antibody can be coupled to a peroxidase such as horseradish peroxidase which is then detected by incubation with a chemiluminescent substrate. A primary or secondary antibody can be coupled to an electrochemiluminescent reporter (for example, ruthenium; see Valenti et al, J Am Chem Soc. 2017 Nov. 8).

IV. Kits and Articles of Manufacture

Certain aspects of the present disclosure relate to kits or articles of manufacture comprising solid antigen/carrier protein gels.

In some embodiments, a kit of the present disclosure comprises a first solid antigen/carrier protein gel of the present disclosure comprising a purified antigen and a second solid antigen/carrier protein gel of the present disclosure comprising the purified antigen at a different concentration from that of the first solid antigen/carrier protein gel.

In some embodiments, the first and/or second solid antigen/carrier protein gel(s) are sectioned, e.g., as described in section II above. In some embodiments, the first and/or second solid antigen/carrier protein gel(s) are affixed to a solid substrate, e.g., as described in section II above.

In some embodiments, a kit of the present disclosure further comprises a third solid antigen/carrier protein gel of the present disclosure that does not contain the purified antigen (e.g., for use as a negative control). In some embodiments, the third solid antigen/carrier protein gel is sectioned, e.g., as described in section II above. In some embodiments, the third solid antigen/carrier protein gel is affixed to a solid substrate, e.g., as described in section II above.

In some embodiments, the kits may further comprise instructions for using the kits, e.g., according to any of the methods described in section III above.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Validating BSA Gels as a Platform Approach to IHC Controls

FIG. 1 shows exemplary workflow 100 for IHC staining in tissue samples. Importantly, IHC staining demonstrates not only the expression level of a target, but also its subcellular and tissue distributions.

The following Example describes a new platform approach for generating IHC controls that can be adapted to a wide range of targets. This approach was validated using human BCL2, a target for which 3+ positive control tissues can be identified (for example, human chronic lymphocytic leukemia tumor samples often score as 3+ in this assay), but are difficult to procure, or are limited by ethical considerations, for routine use as staining controls. The generality of the approach was also demonstrated using mouse and rat IgG and a human protein of interest.

Methods

Approximately 0-0.5 mg of antigen containing approximately 0 to $10^{-4}$ M of the target epitope was mixed with 0.5 mL 25% BSA in PBS in a 1.5 mL microcentrifuge tube. 0.5 mL 37% formaldehyde was added to the tube. The tube was heated for 10 minutes at 85° C., then left overnight at room temperature to solidify if containing a fixative (e.g., formalin). The resulting gel was removed from the tube and put into 10% neutral buffered formalin (NBF). Subsequently, the gel was dehydrated through graded alcohols to xylene, infiltrated with warm paraffin wax, embedded in a paraffin block, sectioned on a microtome, and stained using the primary mouse monoclonal anti-BCL2 antibody 124 and the horseradish peroxidase (HRP)/3,3'-diaminobenzidine (DAB) chromogenic enzyme/substrate system according to standard IHC methods.

The IF detection assay was developed on the Ventana Discovery Ultra automated staining instrument. Four micron sections containing the target BSA/peptide samples were cut, deparaffinized and pretreated with CC1 cell conditioning solution. The primary mouse monoclonal anti-BCL2 antibody 124 was incubated for 16 minutes at 37° C. and detected with the OmniMAP anti-mouse HRP Detection System for 8 minutes, followed by the Ventana Discovery Red 610 detection system for 16 minutes.

Whole-slide brightfield and immunofluorescent images were acquired at a scanning resolution of 0.46 microns/pixel using the Hamamatsu Nanozoomer-XR digital slide scanner equipped with a 20× 0.75 NA objective lens and fluorescent module. Brightfield imaging was performed and used for focusing. When applicable, immunofluorescence signal was acquired using a TRITC filter at 1× exposure (3.4 ms photon collection) and 1× gain. Autofluorescence was captured using a DAPI (2× exposure, 6.8 ms photon collection, 2× gain) and CFP filter (4× exposure, 13.6 ms photon collection, 2× gain). Illumination power was set at 50% for all immunofluorescence acquisition. Image analysis was performed using Matlab version 9.3. Regions of interest (ROI) were manually marked up (brightfield scan only) or generated using thresholding and morphological filtering on the autofluorescence channels and transferred onto the TRITC channel for intensity measurement. Average grayscale intensity was calculated in 8-bit depth. Average optical absorbance (brightfield DAB-labeled) or emittance (fluorescently labeled) was computed by summing all pixel absorbance or emittance values within a ROI (as calculated by the respective natural log formula below) and normalized to the total ROI pixel count. All zero pixel grayscale intensity values were approximated using a value of 1. Brightfield pixel absorbance=log(255/pixel grayscale intensity). Fluorescent pixel emittance=log(pixel grayscale intensity).

For validation experiments, the BSA gel samples were generated in microcentrifuge tubes as described above, embedded in paraffin blocks, then used to create a tissue microarray of 600 micron-diameter cylinders cut from the paraffin blocks and re-embedded into the array using standard tissue microarray techniques.

For BCL2 experiments, a peptide comprising the sequence Ac-YGSGGAAPAPGIFSSQPGGSGC-amide (SEQ ID NO:1) was used. Underlined amino acids correspond to the wild-type (unmutated) amino acids 41-54 of the human BCL2 sequence as set forth in UniProt Accession No. P10415. The peptide also includes an amino-terminal linker sequence (Ac-YGSG) (SEQ ID NO:6) with acetyl-Y (tyrosine) that allows coupling with an aldehyde (e.g., formaldehyde) and a carboxy-terminal linker sequence (GSGC-amide) (SEQ ID NO:7) with C (cysteine)-amide that is reactive with a variety of cross-linking reagents, e.g. maleimide-, haloacetyl- or pyridyl disulfide-containing compounds.

Results

Figure 2B:
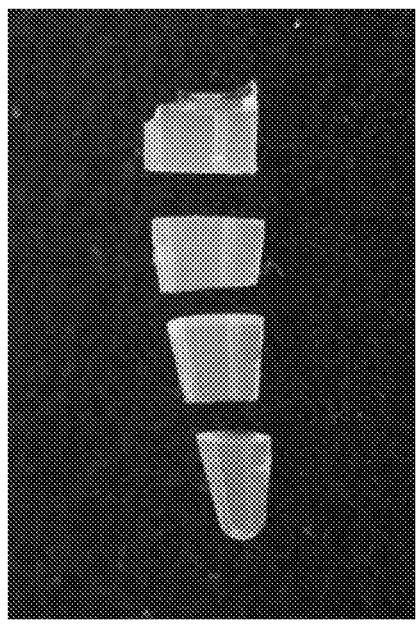
FIGS. 2B & 2C show different views of sections of a BSA gel created in, then removed from, a 1.5 mL microcentrifuge tube.
Figure 2C:
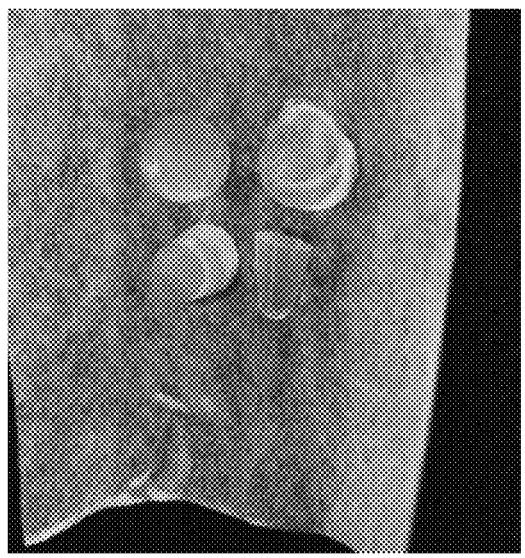
Figure 2A:
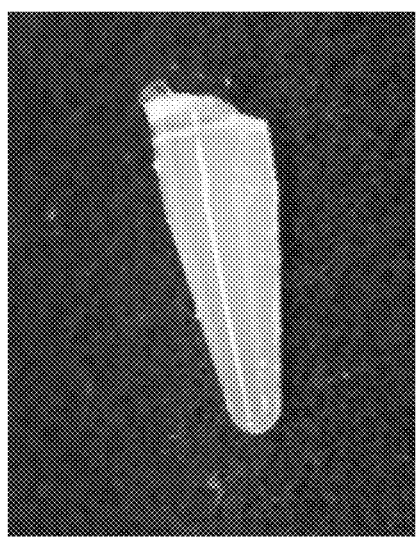
FIG. 2A shows a bovine serum albumin (BSA) gel created in, then removed from, a 1.5 mL microcentrifuge tube.
Figure 2E:
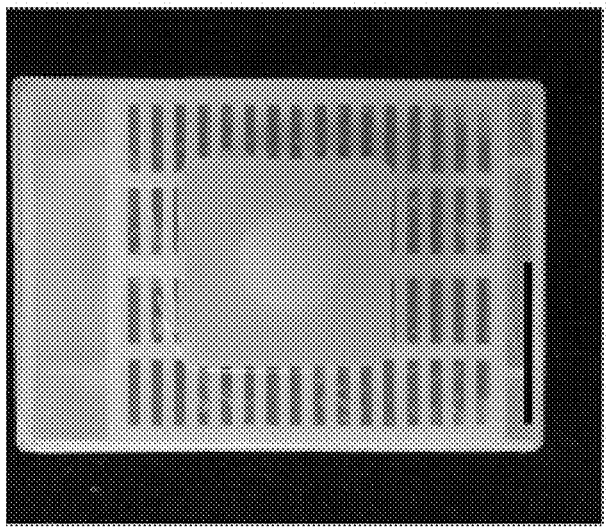
FIG. 2E shows a sliced gel portion embedded in a paraffin "donor block". Scale bar: 1 cm.
Figure 2F:
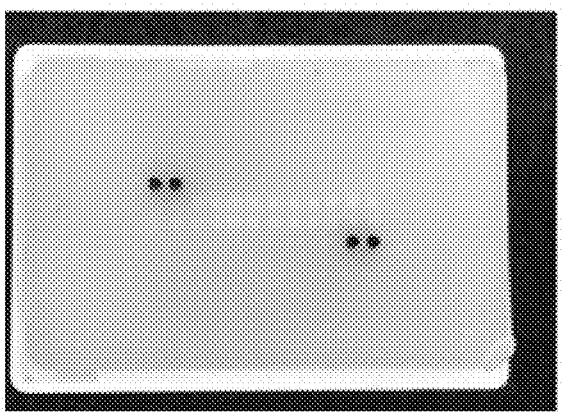
FIG. 2F shows a tissue microarray (TMA) created from various paraffin gel donor blocks. The darkest cores are orientation references containing black and green pigment.
Figure 2D:
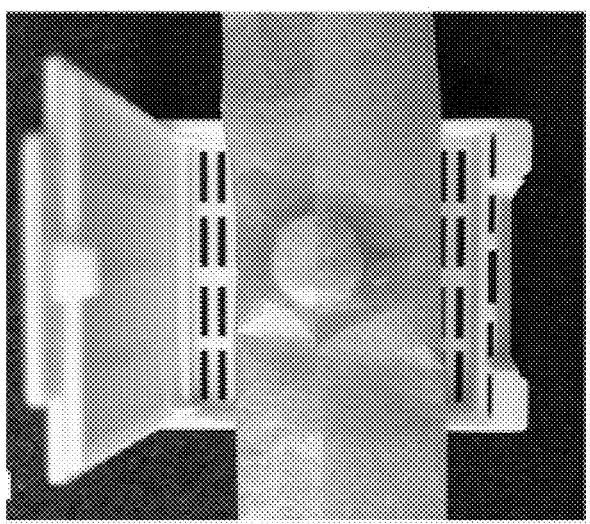
FIG. 2D shows a sliced gel portion prepared for dehydration and paraffin processing.

BSA/peptide gels were prepared as described supra. Mixing the antigen (e.g., a peptide) with BSA in a liquid solution before producing a gel allowed the peptide to be mixed uniformly. The resulting gel (FIG. 2A) can be constructed in any desired shape (in this example, a gel was produced in the shape of a 1.5 mL microcentrifuge tube). The gel can also be sectioned (FIGS. 2B & 2C) and subjected to typical IHC processing steps such as antigen retrieval, blocking, primary/secondary antibody incubation, and detection (e.g., using an enzyme/substrate approach). For example, FIG. 2D shows a sliced gel portion prepared for dehydration and paraffin processing, and FIG. 2E shows a sliced gel portion embedded in a paraffin donor block. FIG. 2F shows a TMA created from various paraffin gel donor blocks, along with cores containing black and green pigment for orientation references. Peptide antigens are able to cross-link to the BSA more efficiently than to lysozyme, thereby retaining the antigen in the BSA gel during IHC processing and detection.

Figure 3A:
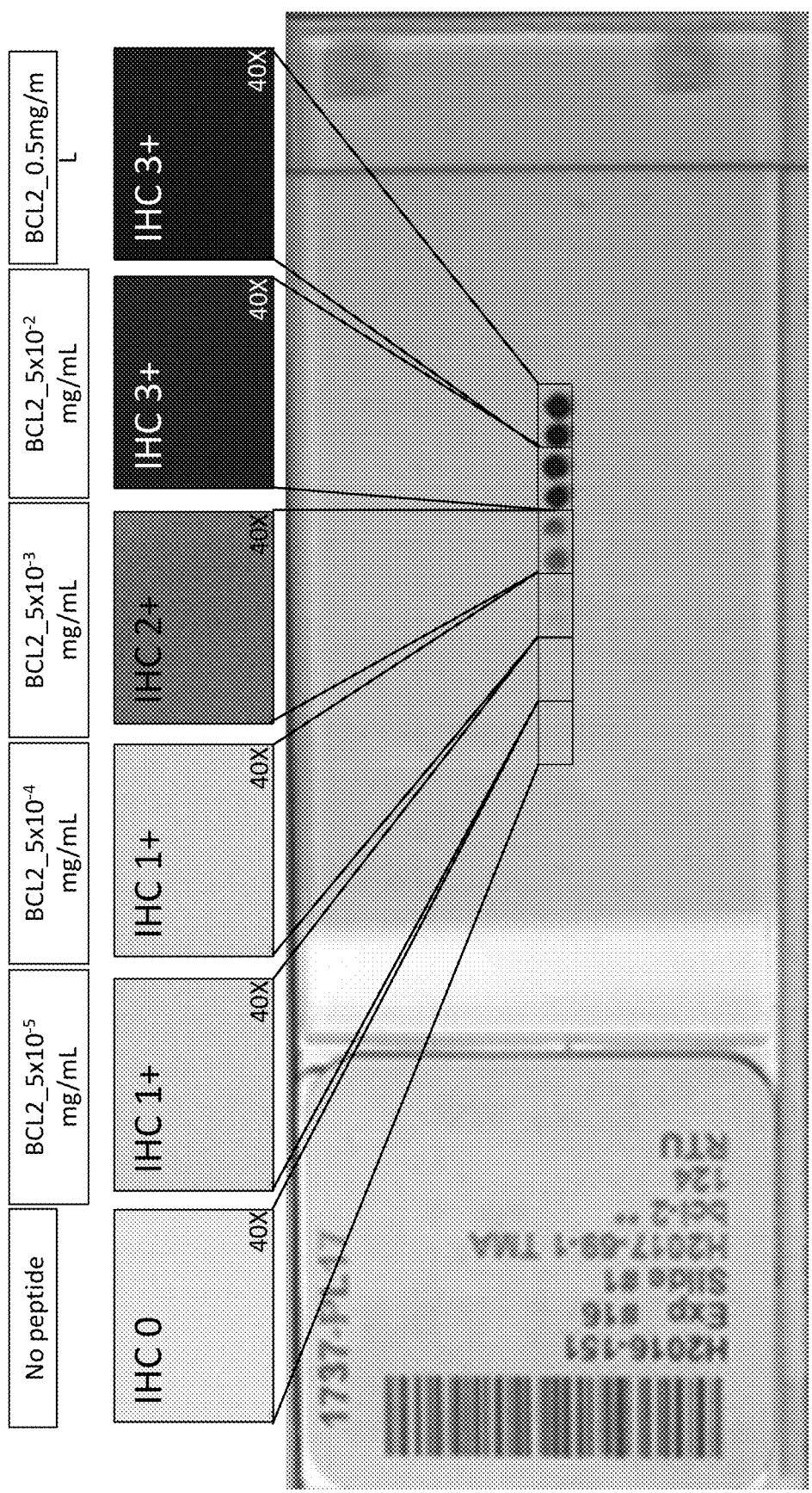
FIG. 3A shows the results of IHC staining of 4 micron-thick section of BCL2 peptide/BSA gel cylinders embedded in a paraffin block. Inserts show 40× magnification of BCL2 IHC staining using sections obtained from BCL2 peptide/BSA gels containing (from left to right) no peptide, $5\times10^{-5}$ mg/mL (2.5E-8 M) BCL2 peptide, $5\times10^{-4}$ mg/mL (2.5E-7 M) BCL2 peptide, $5\times10^{-3}$ mg/mL (2.5E-6 M) BCL2 peptide, $5\times10^{-2}$ mg/mL (2.5E-5 M) BCL2 peptide, or 0.5 mg/mL (2.5E-4 M) BCL2 peptide. Sections corresponding to 0, 1+, 2+, or 3+(on a 0 to 3+ qualitative scale) BCL2 staining are labeled.

To examine the feasibility of peptide/BSA gels as IHC controls, varying concentrations of BCL2 peptide were mixed into BSA gels, then sectioned and prepared according to standard IHC techniques. BCL2 was detected using a BCL2 primary antibody directed against the human BCL2 protein (the "CONFIRM anti-bcl-2 (124) Mouse Monoclonal Primary Antibody" BCL2 from Ventana Medical Systems), a biotinylated secondary antibody, avidin-conjugated HRP as a chromogenic reporter, and DAB as a chromogenic substrate. As shown in FIG. 3A, serially increasing BCL2 levels from 0 to 0.5 mg/mL ($2.5*10^{-4}$ M) led to a graded increase in IHC staining intensity. A negative control lacking peptide caused no staining, whereas BCL2 peptide was resolvable through the entire tested range of $5\times10^{-5}$ mg/mL (corresponding to 25 nM peptide concentration) to 0.5 mg/mL (corresponding to $2.5*10^{-4}$ M peptide concentration). Importantly, 1+, 2+, and 3+ BCL2 staining levels were each achieved at different peptide concentrations. As consistent and uniform 3+ BCL2 staining is typically difficult to find in readily available tissue samples, this alternative approach provides an easier and more standardized way to obtain a gradient of BCL2 expression controls than assaying different types of tissues.

Figure 3B:
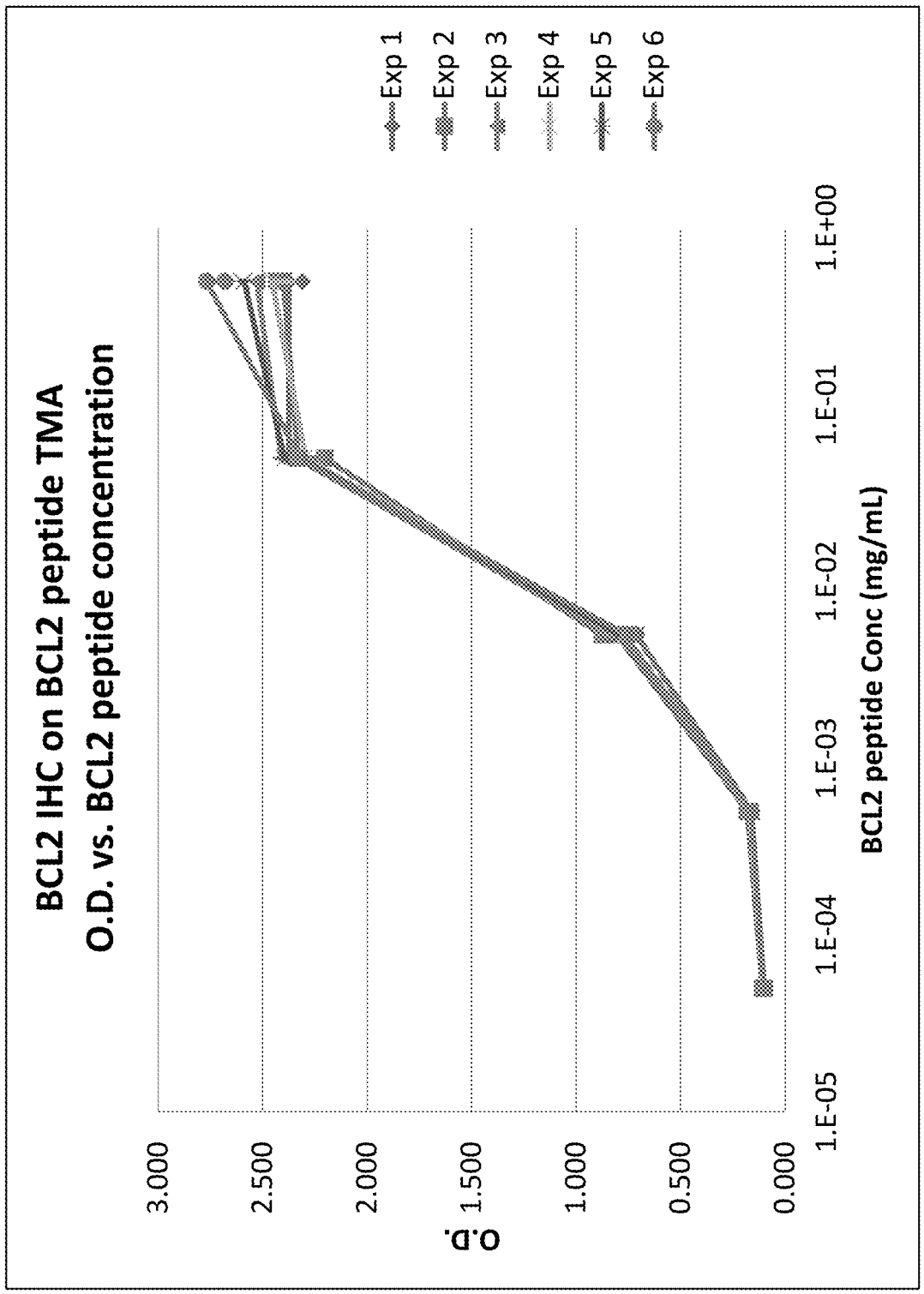
FIG. 3B shows the results of six independent experiments analyzing the sections shown in FIG. 3A for optical density (OD) vs. BCL2 peptide concentration.
Figure 3C:
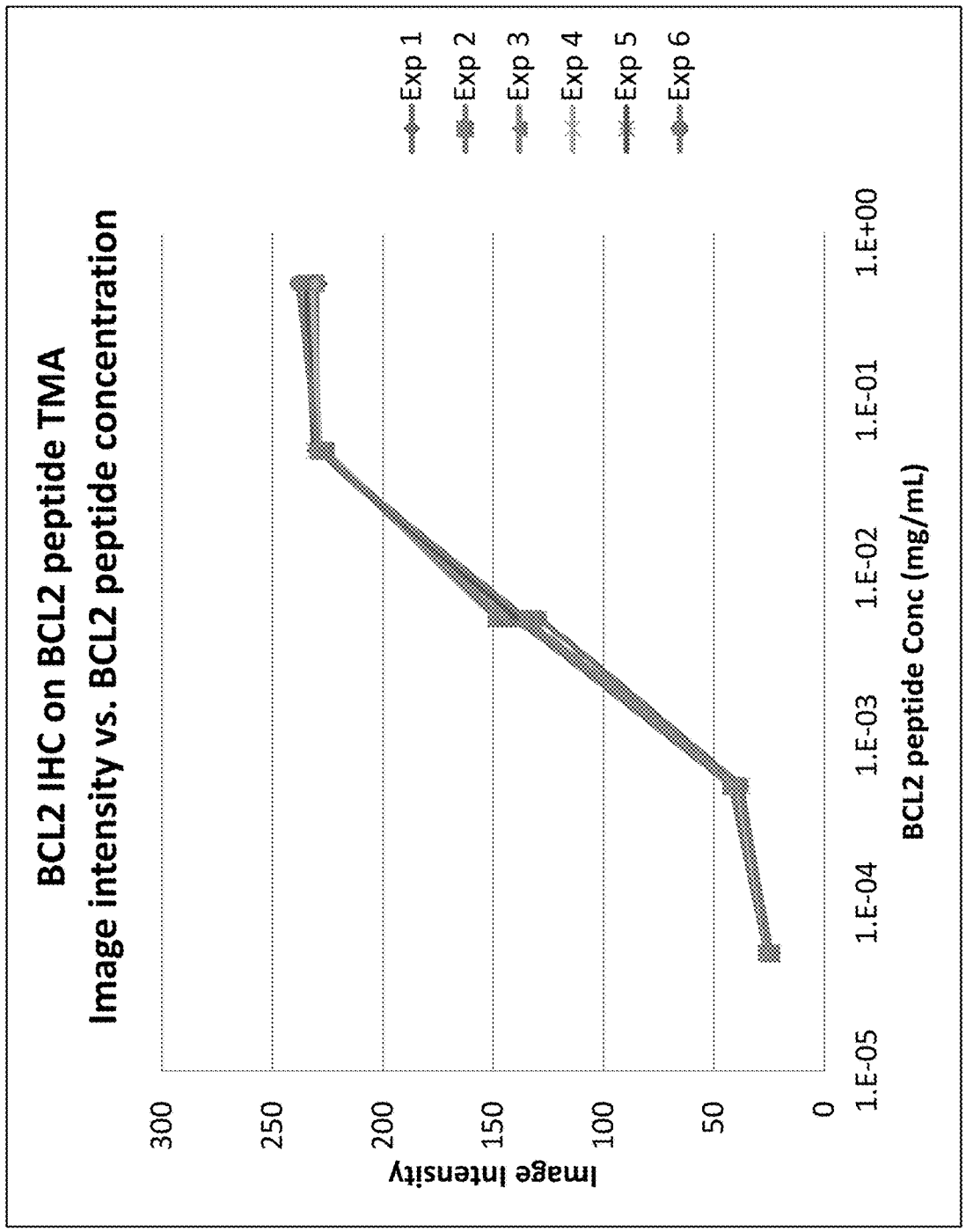
FIG. 3C shows the results of six independent experiments analyzing the sections shown in FIG. 3A for image intensity vs. BCL2 peptide concentration.

To examine the consistency of staining, six independent experiments were conducted by staining the BCL2 peptide/BSA gels as described above and analyzing the resultant images using MATLAB. Analyses of both optical density (OD; FIG. 3B) and image intensity (FIG. 3C) as a function of peptide concentration indicated that staining was consistent between experiments.

Figure 3E:
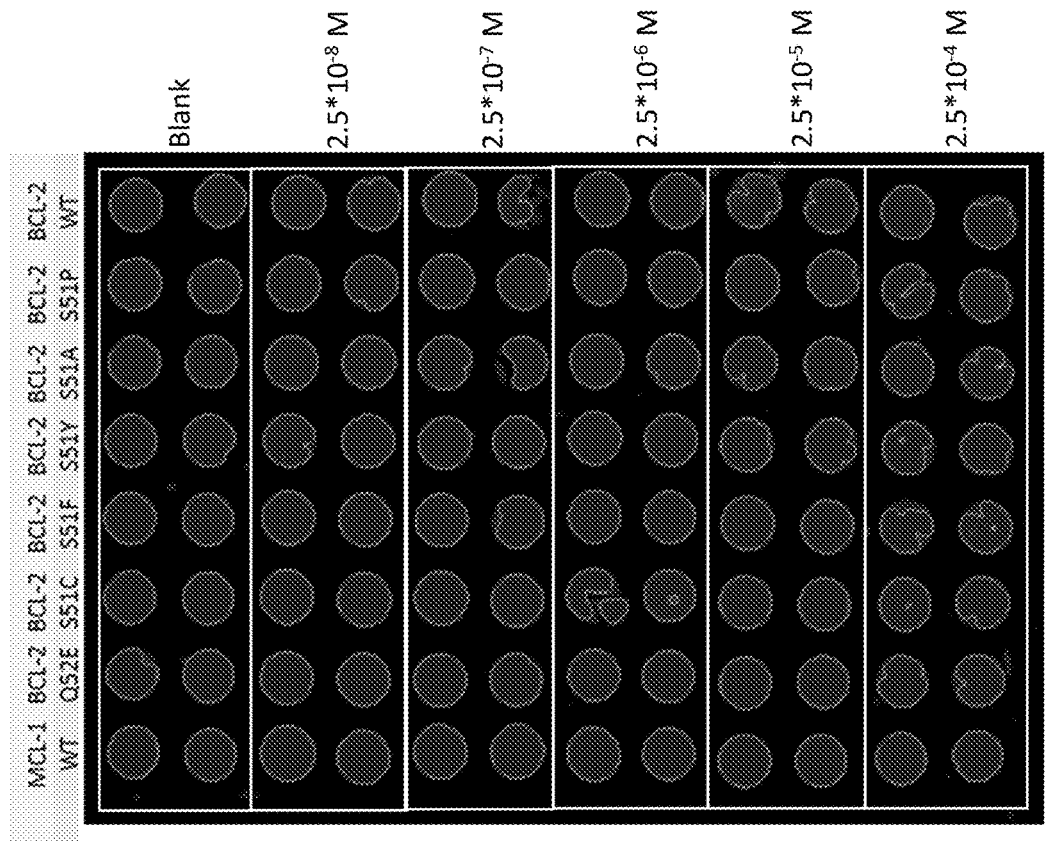
FIGS. 3D & 3E show the results of quantitative immunofluorescence (IF) staining of 4 micron-thick section of BCL2 peptide/BSA gel cylinders embedded in a paraffin block, stained with anti-BCL2 primary antibody, and detected with a fluorescent reporter (using the Ventana Medical Systems OmniMAP anti-mouse HRP Detection System, followed by the Ventana Discovery Red 610 detection system). Test samples include wild-type (unmutated) BCL2 peptide, BCL2 peptides with six different single amino acid substitutions, and a peptide from the MCL1 protein (a negative control sample that is not expected to bind the anti-BCL2 antibody).
Figure 3D:
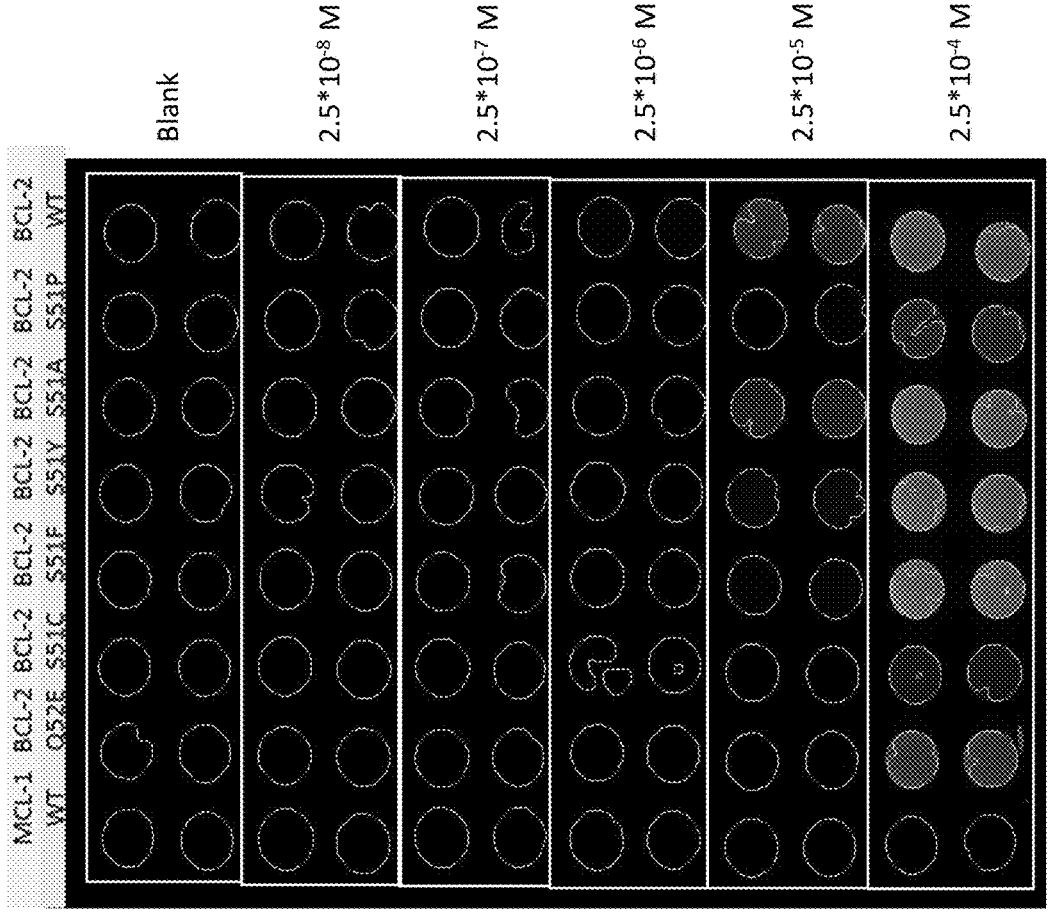
Figure 3G:
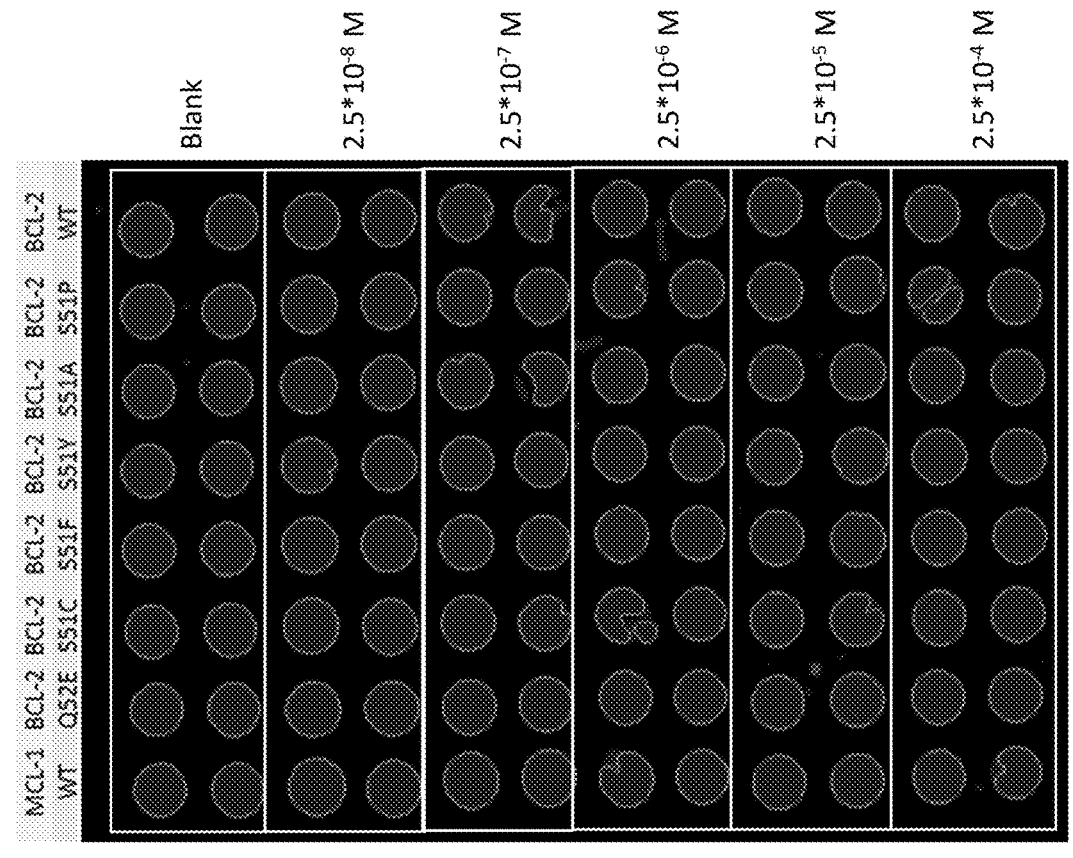
FIGS. 3F & 3G show the results of quantitative immunofluorescence (IF) staining of 4 micron-thick section of BCL2 peptide/BSA gel cylinders embedded in a paraffin block, stained with a naïve control primary antibody.
Figure 3F:
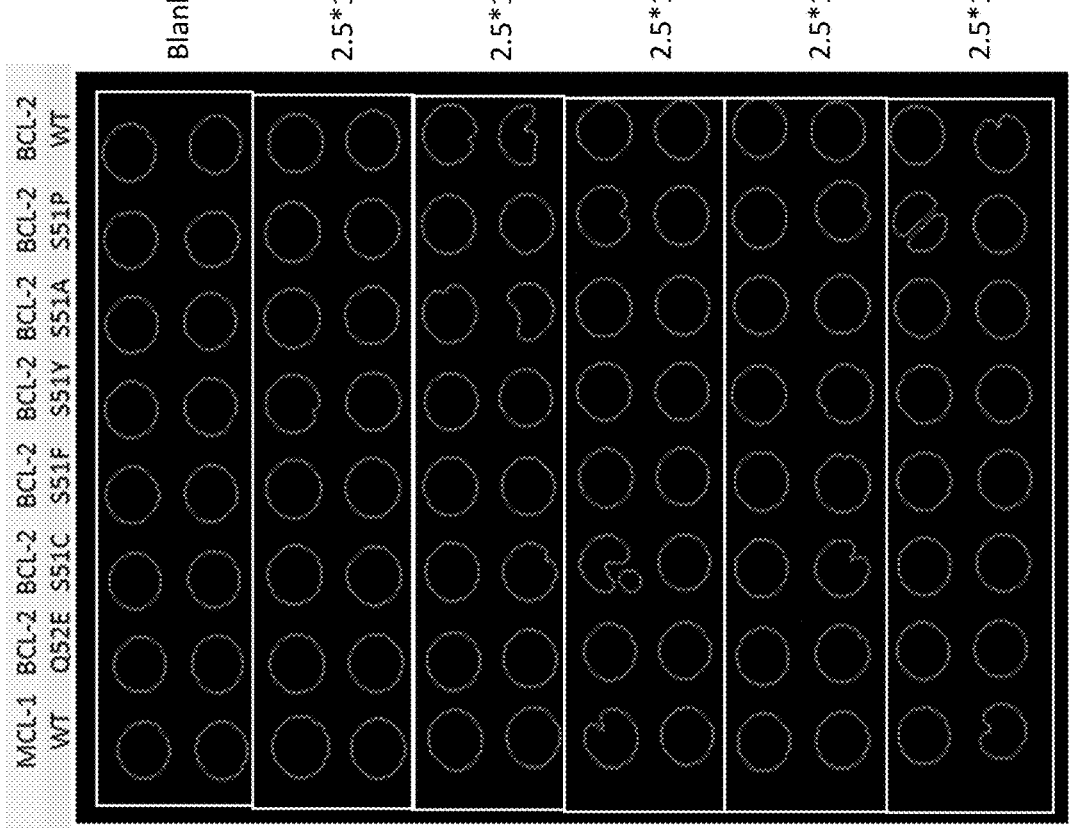
Figure 3H:
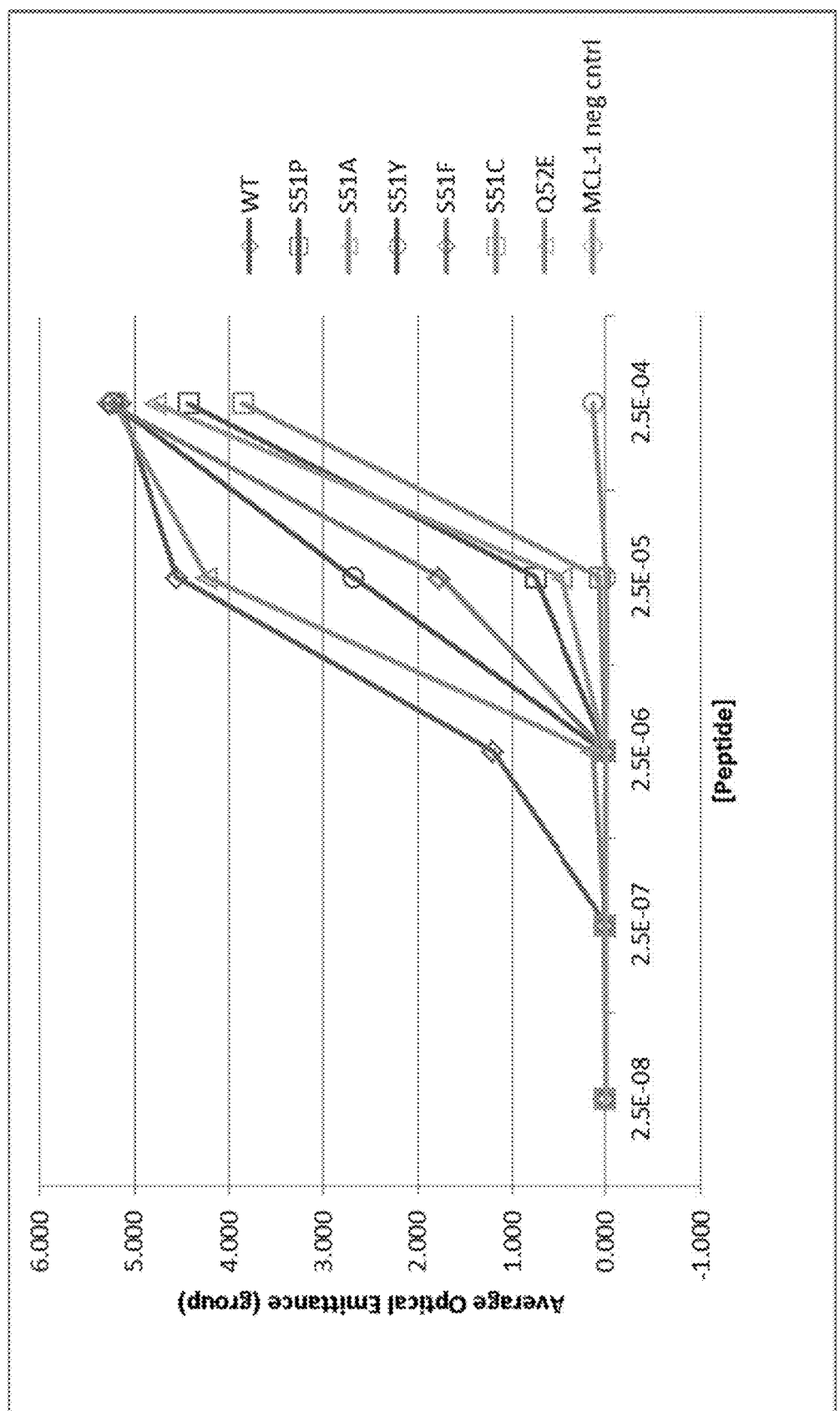
FIG. 3H shows quantification of the results (reported as Average Optical Emittance) illustrated in FIG. 3D. Wild-type BCL2 peptide shows the strongest signal at each concentration; the negative control MCL1 peptide shows minimal signal, as expected. The six BCL2 peptides with single amino acid substitutions show variable signal, generally intermediate between the wild type BCL2 and negative control MCL1 peptides.
Figure 3I:
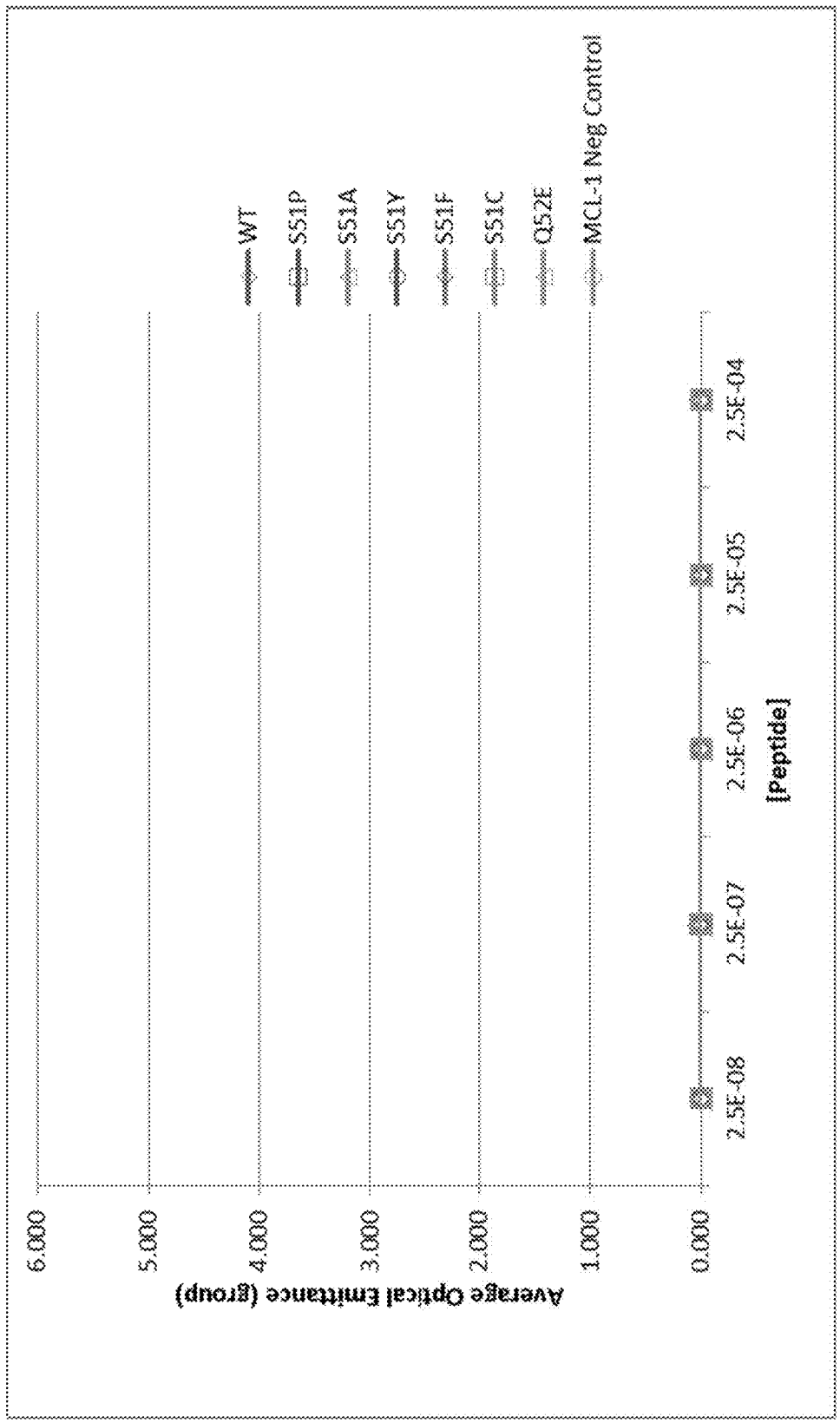
FIG. 3I shows quantification of the results (reported as Average Optical Emittance) illustrated in FIG. 3F. The naïve control antibody shows nearly undetectable signal, as expected.
Figure 3J:
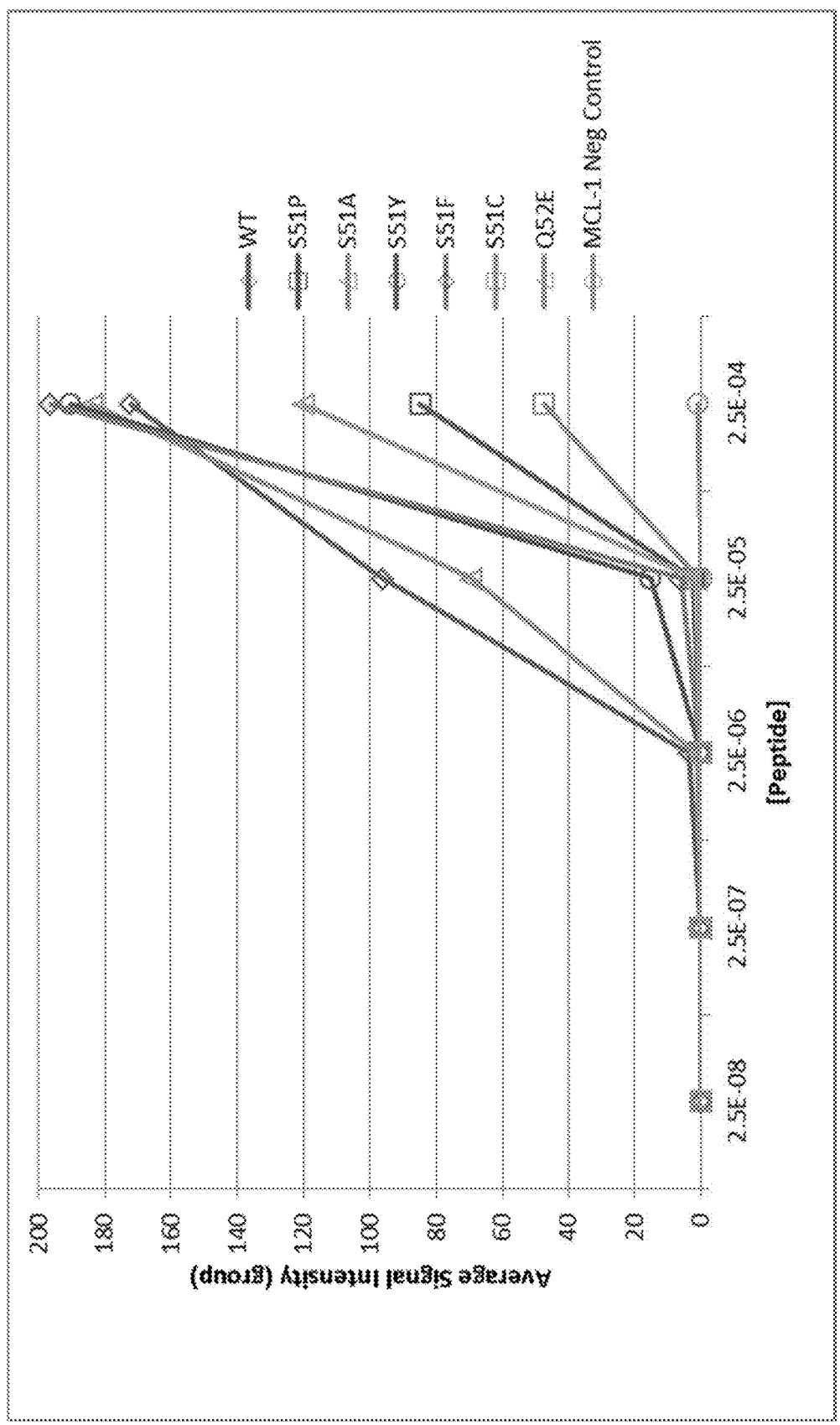
FIG. 3J shows quantification of the results (reported as average signal intensity) illustrated in FIG. 3D. Wild-type BCL2 peptide shows the strongest signal at each concentration; the negative control MCL1 peptide shows minimal signal, as expected. The six BCL2 peptides with single amino acid substitutions show variable signal, generally intermediate between the wild type BCL2 and negative control MCL1 peptides.
Figure 3K:
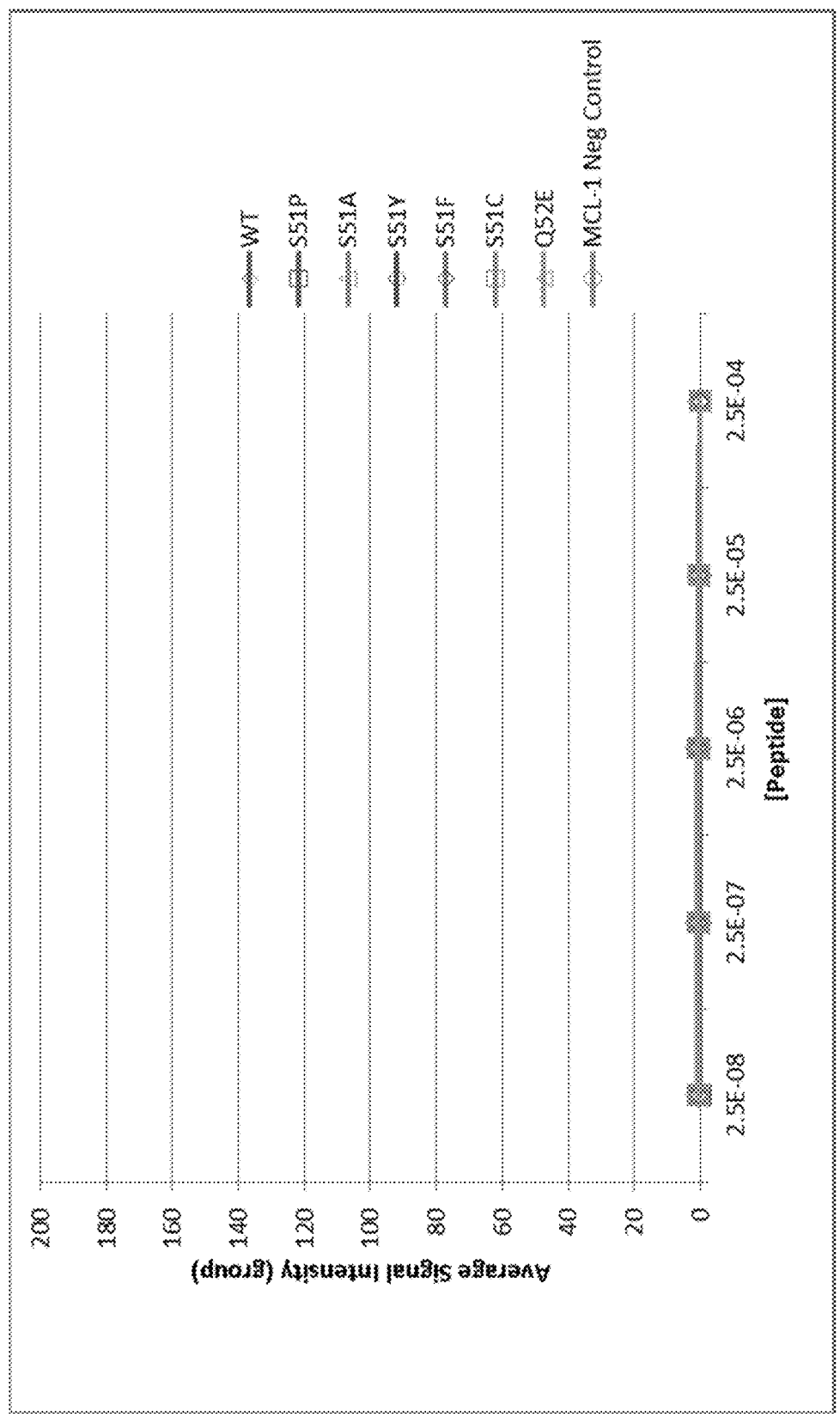
FIG. 3K shows quantification of the results (reported as average signal intensity) illustrated in FIG. 3F. The naïve control antibody shows nearly undetectable signal, as expected.

BCL2 peptide/BSA gels were also subjected to quantitative immunofluorescence staining. Like the results obtained using chromogenic staining, IF analyses showed a graded increase in staining intensity as a function of peptide concentration (FIG. 3D). Analyses of optical emittance (FIG. 3H) and signal intensity (FIG. 3J) again demonstrated consistent, graded increases in staining. Negative control staining with a naïve control primary antibody (FIGS. 3F, 3I, &

3K) or autofluorescence of the gels (FIGS. 3E & 3G) showed no increase in intensity, as expected.

Secondary antibody controls were also examined. Using a donkey anti-mouse secondary antibody, mouse IgG embedded in a BSA gel was readily detected, whereas rat IgG gave no detectable signal, as shown in FIG. 4A. Similarly, using a donkey anti-rat secondary antibody, rat IgG embedded in a BSA gel was readily detected, whereas mouse IgG gave no detectable signal (FIG. 4B). This confirms the specificity of the BSA gel approach, demonstrating that secondary antibody does not non-specifically bind to peptide/BSA gels lacking the target of the antibody.

Figure 4C:
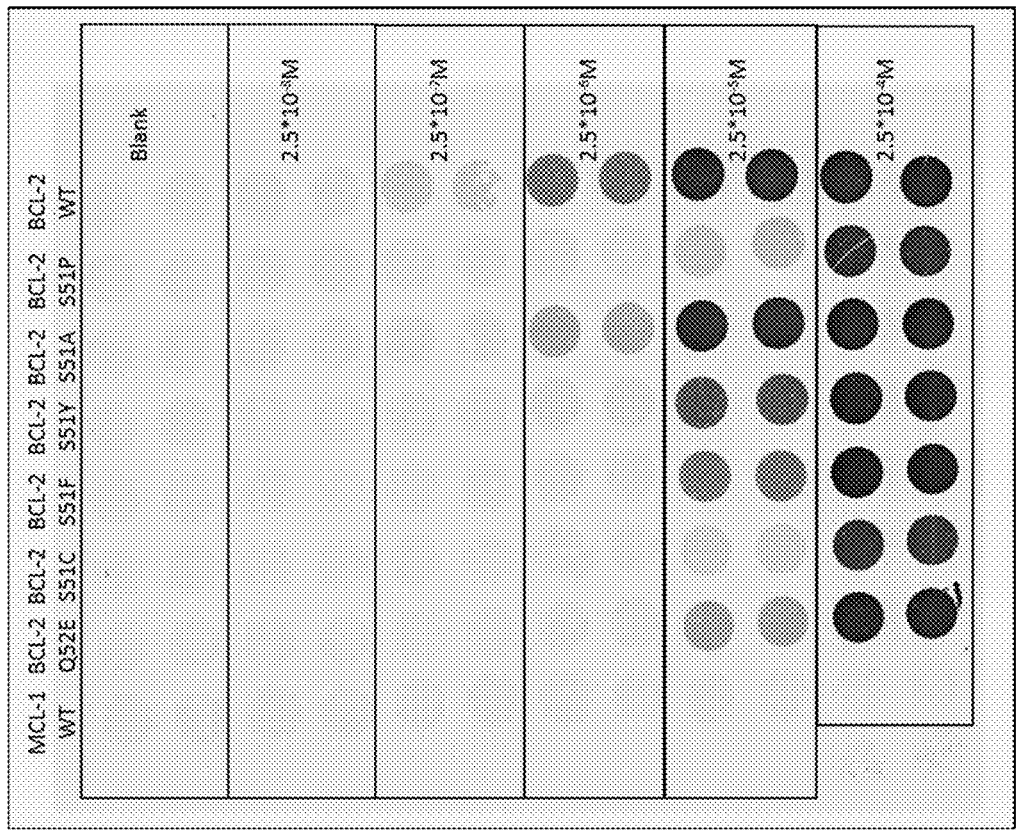
FIG. 4C shows the effect on IHC staining of amino acid substitutions (as indicated) introduced into the anti-BCL2 clone 124 antibody epitope of human BCL2 (amino acids 41-54 of the human BCL2 sequence as set forth in UniProt Accession No. P10415). This image is of a 4 micron-thick section, cut from a paraffin-embedded tissue microarray constructed using BCL2 peptide/BSA gel cylinders (each 1 mm in diameter), stained with the anti-BCL2 antibody clone 124 and detected with chromogenic reagents and methods.
Figure 4D:
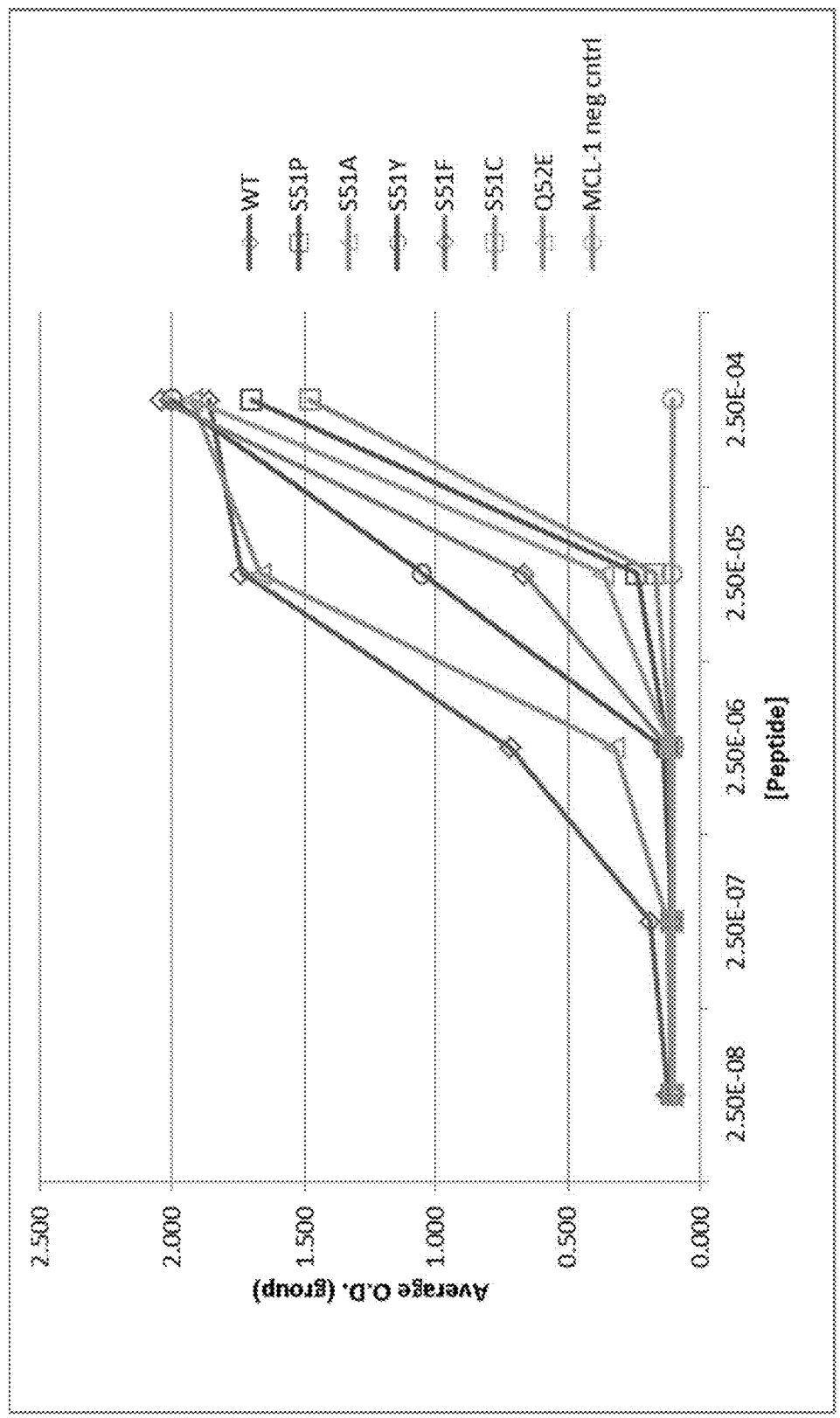
FIG. 4D shows quantification of the results (reported as optical density (O.D.)) illustrated in FIG. 4C.
Figure 5A:
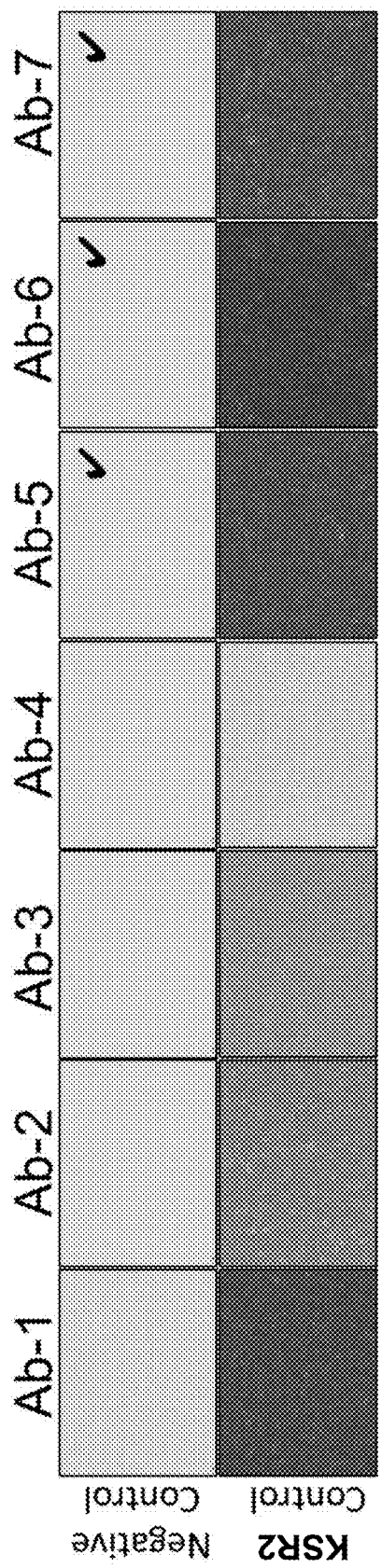
Figure 5B:
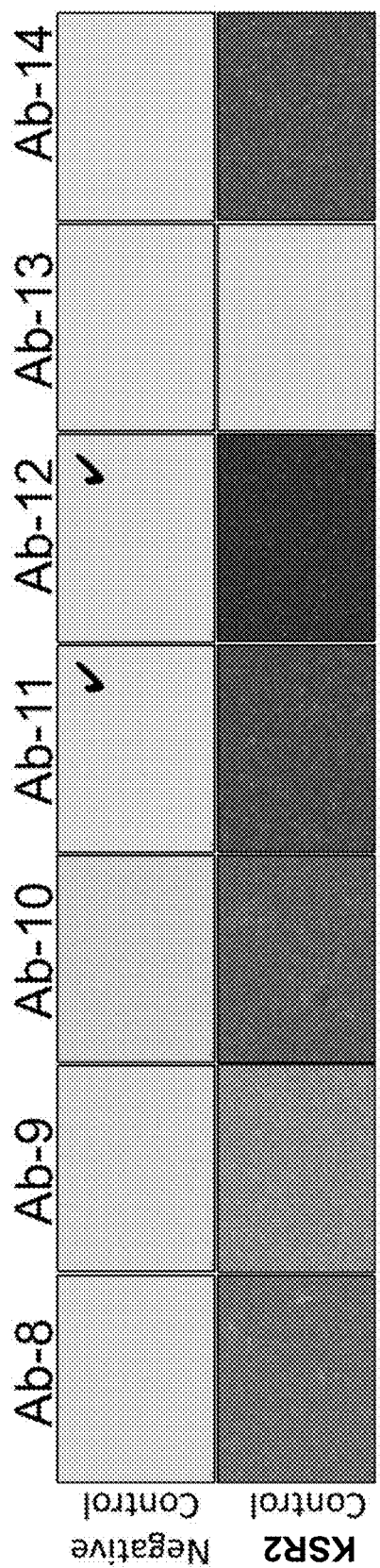
Figure 5D:
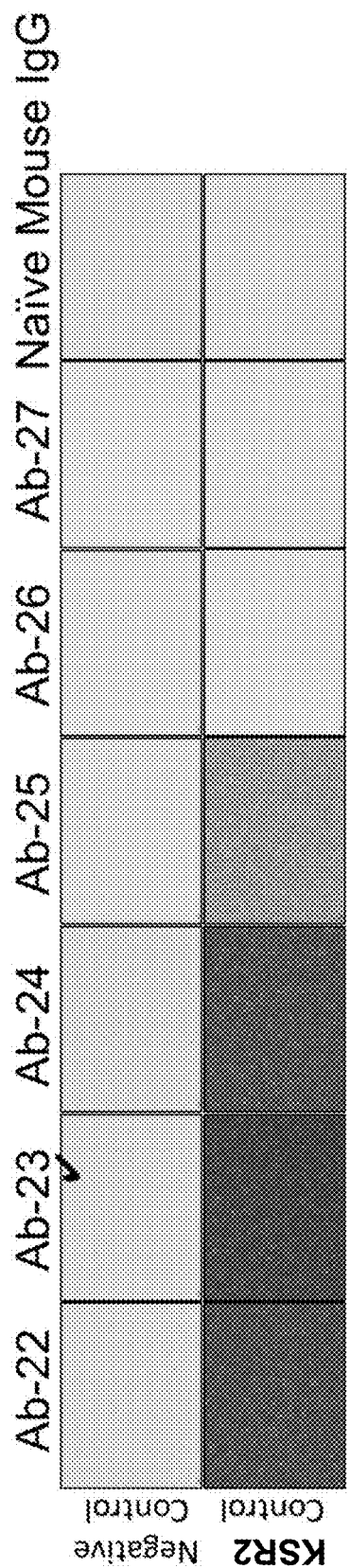

To examine the specificity of staining, six peptides with clinically relevant single amino acid substitutions in the anti-BCL2 clone 124 antibody epitope were synthesized, embedded in BSA as described above, and stained. As shown in FIG. 4C (and seen in FIGS. 3D, 3II, and 3J), these mutations showed a clear effect on IHC staining (i.e., a decrease of varying degree in the intensity of signal, depending on the specific amino acid substitution), demonstrating the practicality of quantifying the effect of specific amino acid substitutions on staining intensity.

Next, the generality of the peptide/BSA gel platform was examined by screening several uncharacterized antibodies for specific detection of a target of interest. Twenty-seven (27) antibody clones isolated from mice immunized with human KSR2 were screened by IHC for detection of positive and negative controls (FIGS. 5A-5D). For the negative control, BSA gel with no other added protein or peptide was used. For the positive control, BSA gels were generated with the human KSR2 protein that had been used to immunize mice. As expected because the candidate antibody clones had been selected in a separate process for binding the unfixed human target protein, most antibody clones were able to detect the human protein in the protein/BSA gels (as evidenced by DAB signal of some intensity above background). However, antibodies most suitable for use in IHC assays should show little to no detectable signal for the negative control, while at the same time showing strong staining for the positive control. Among the antibodies tested, clones 5, 6, 7, 11, 12, 15, and 23 were the most promising, as these gave the highest ratio of specific staining of the target antigen to non-specific staining in the negative control sample. In contrast, clones 4, 13, 26, and 27 showed ineffective staining of the target antigen, while antibodies 10 and 20 showed weak but significant non-specific staining of the negative control sample. These results serve to illustrate the problem that not all antibodies able to bind a target of interest in its unfixed state are suitable to use in IHC staining. The peptide control reagents and processes described here can help to identify the most suitable antibodies for use in IHC applications.

Taken together, these results demonstrate that the antigen/BSA gel approach provides a robust platform for generating IHC controls that is applicable to many target antigens. The approach yields controls representing a gradient of IHC staining that correlates with a range of target concentration, thus demonstrating the quantitative potential of target/BSA gels. Unlike IHC controls from tissues or cell lines, peptide/BSA gels are readily created in the laboratory as need requires, consistent, reproducible, inexpensive, versatile, and antigen-specific. Secondary antibody controls demonstrated the specificity of the approach. Moreover, the approach is ideally suited for identifying antibodies suitable for IHC analysis of a target of interest, a process in which hundreds to thousands of candidate antibodies are typically screened in order to identify a small handful (e.g., 2-5) of leads for further characterization.

Example 2: Examining Conditions for Gel Formation

The following Example describes testing a range of conditions for their effect on gel formation.

Methods

For evaluation of BSA gel formation, 1 mL of a BSA solution in PBS was heated at a range of temperatures from 25-85° C. No formaldehyde was included in the BSA/PBS solution. The solution was heated continuously and observed under heated conditions at various time points for liquid/solid phase. Solutions were tested at the following BSA concentrations: 25%, 20%, 15%, 10%, 5%, and 2%.

For evaluation of other protein sources for making gels, 25% solutions of the following were generated in PBS: casein, lact-albumin, soybean flour, and non-fat dry milk. 500 μL 37% formaldehyde was mixed with 500 μ, of the respective 25% protein/PBS solution and incubated for 10 minutes at 85° C.

For evaluation of fixatives, 500 μL fixative was mixed with 500 μ, 25% BSA solution in PBS and incubated for 10 minutes at 85° C. Fixatives tested included: 10% neutral buffered formalin (NBF), ½ strength Karnovski's (glutaraldehyde/paraformaldehyde), Methacarn, Carnoy's fluid, and Bouin's.

For evaluation of formaldehyde concentration, 500 μ, formaldehyde solution was mixed with 500 μL 25% BSA solution in PBS and incubated for 10 minutes at 85° C. Formaldehyde solutions were tested at the following concentrations (concentration refers to the original concentration prior to diluting with BSA solution): 1%, 2%, 4.5%, 9%, and 18%. Specifically, stock formaldehyde solution at 37% was mixed with distilled water to make a final volume of 500 microliters containing 1%, 2%, 4.5%, 9%, or 18% formaldehyde; these solutions were then mixed (each in separate microfuge tubes) with an equal volume (500 microliters) of 25% BSA solution and heated as described above.

Results

FIG. 6 illustrates the effects of heating temperature and time on 25% BSA gel formation. Heating at 25° C. or 45° C. did not result in any gel formation, even after heating overnight. At 55° C., gel formation was only observed after heating overnight. However, after heating at 65° C. or 85° C., solid gel formation was observed within 6 and 2 minutes, respectively. These results demonstrate the effects of heating temperature and time on BSA gel formation.

Next, the effect of BSA concentration on gel formation was tested. BSA was dissolved in PBS at the following concentrations: 25%, 20%, 15%, 10%, 5%, and 2%. As shown in FIG. 7 (the results for 25% BSA are shown in FIG. 6), gel formation was observed for all concentrations upon heating at 85° C. For BSA concentrations at 5% and above, gel formation was observed within 10 minutes, whereas the 2% BSA solution formed a gel after 20 minutes. No gel formation was observed for any time after heating at 45° C. or 55° C. These results demonstrate that a wide range of BSA concentrations can generate a BSA gel under suitable heating conditions.

Next, casein, lact-albumin, soybean flour, and non-fat dry milk were tested for their ability to form gels. Each was tested at a final concentration of 12.5% in PBS after mixing with formaldehyde (final concentration: 18.5%), as described above. Under these conditions, only soybean flour was observed to form a gel, but the resulting solid was not homogeneous. These data demonstrate the unique properties of serum albumin in promoting gel formation.

Next, various fixatives were tested for their ability to form a BSA gel, including 10% NBF, ½ strength Karnovski's (glutaraldehyde/paraformaldehyde), Methacarn, Carnoy's fluid, and Bouin's. Of these, 10% NBF and Methacarn failed to form a solid. Carnoy's formed a solid before it could be mixed. ½ Karnovski's and Bouin's fixatives formed a clear solid.

The effect of formaldehyde concentration on gel formation was also tested. All concentrations of formaldehyde were able to promote solid gel formation except for 1%. These results show the effect of fixative on gel formation.

Example 3: Evaluating Other Substrates for Gel Formation

The following Example describes evaluating additional proteins for their ability to form a gel suitable for IHC staining.

Methods

BSA (used at 25% final concentration), egg white protein or a mixture of egg white proteins (used at 25% final concentration), gelatin (used at 10% final concentration), lact-albumin (used at 25% final concentration), liver protein powder, soy flour (used at 25% final concentration), casein (used at 10% final concentration), and non-fat dry milk (used at 25% final concentration) were evaluated for the ability to generate solid gels suitable for IHC staining. Protein solutions were mixed with 37% formaldehyde and heated to 85° C. for 10 minutes.

Each type of gel was produced with or without 0.1 mg/mL normal rabbit IgG (DA1E). Sections were stained with donkey anti-rabbit biotinylated secondary antibody at 5 µg/mL, followed by ABC-HRP detection.

For gelatin gels, 10% molten gelatin was mixed with 0.1 mg/mL normal rabbit IgG (DA1E), then cooled for 1 hour at 4° C., transferred to 10% NBF overnight, transferred to 70% ethanol for 2 days, then processed for IHC staining like tissue. For lact-albumin and liver protein powder gels, Histogel™ was added to solidify the gels. For casein gels, 100 mM NaOH was added dropwise to bring the pH to 8.0, with agitation as required to form solution.

For imaging gels, slides were scanned on a Hamamatsu Nanozoomer, and the digital images were captured using image viewing software.

Results

Figure 8:
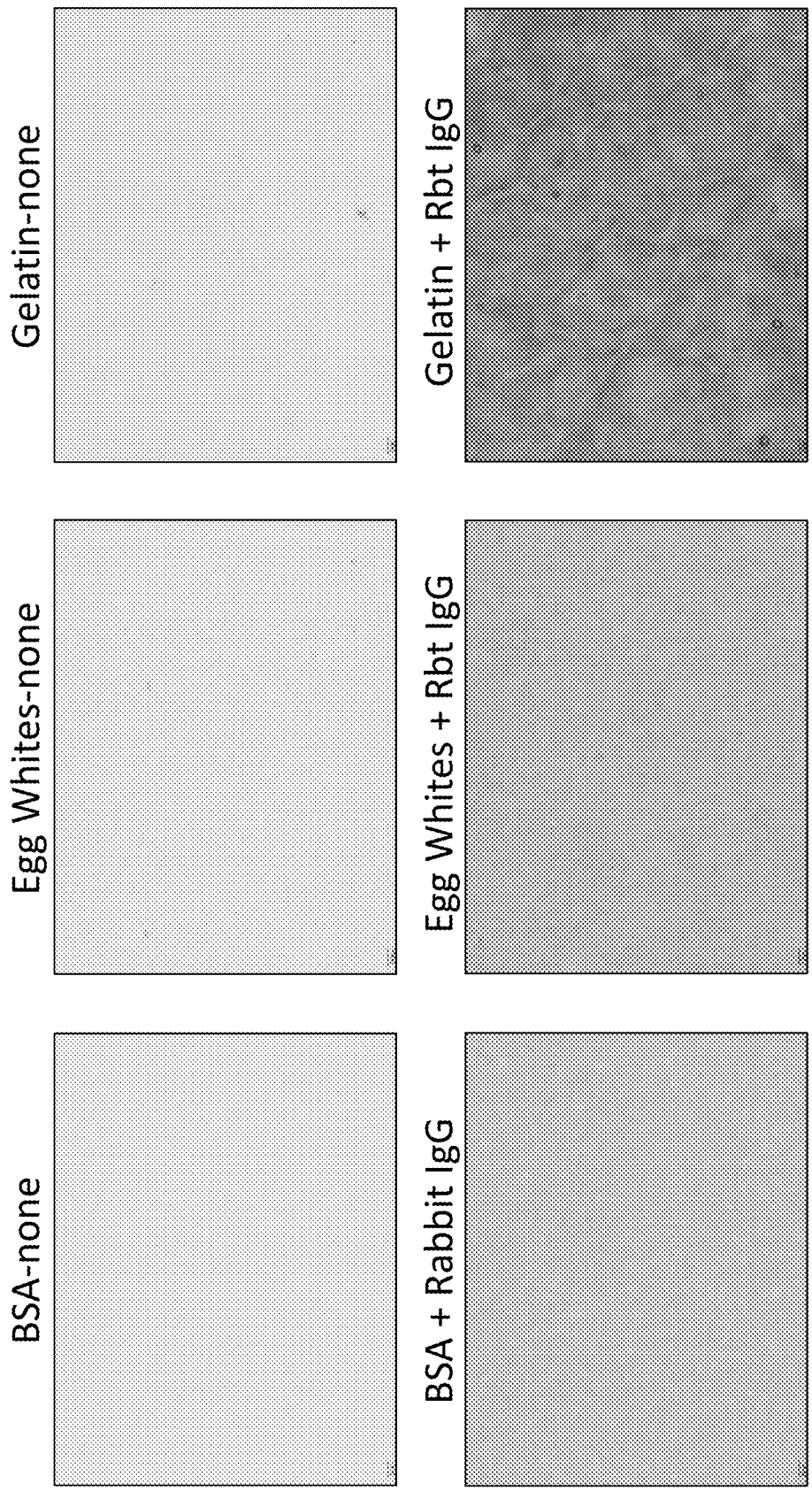
FIG. 8 shows the IHC staining of gels made from BSA, egg white protein, or gelatin with (bottom row) or without (top row) rabbit IgG, detected using an anti-rabbit IgG secondary antibody.
Figure 9:
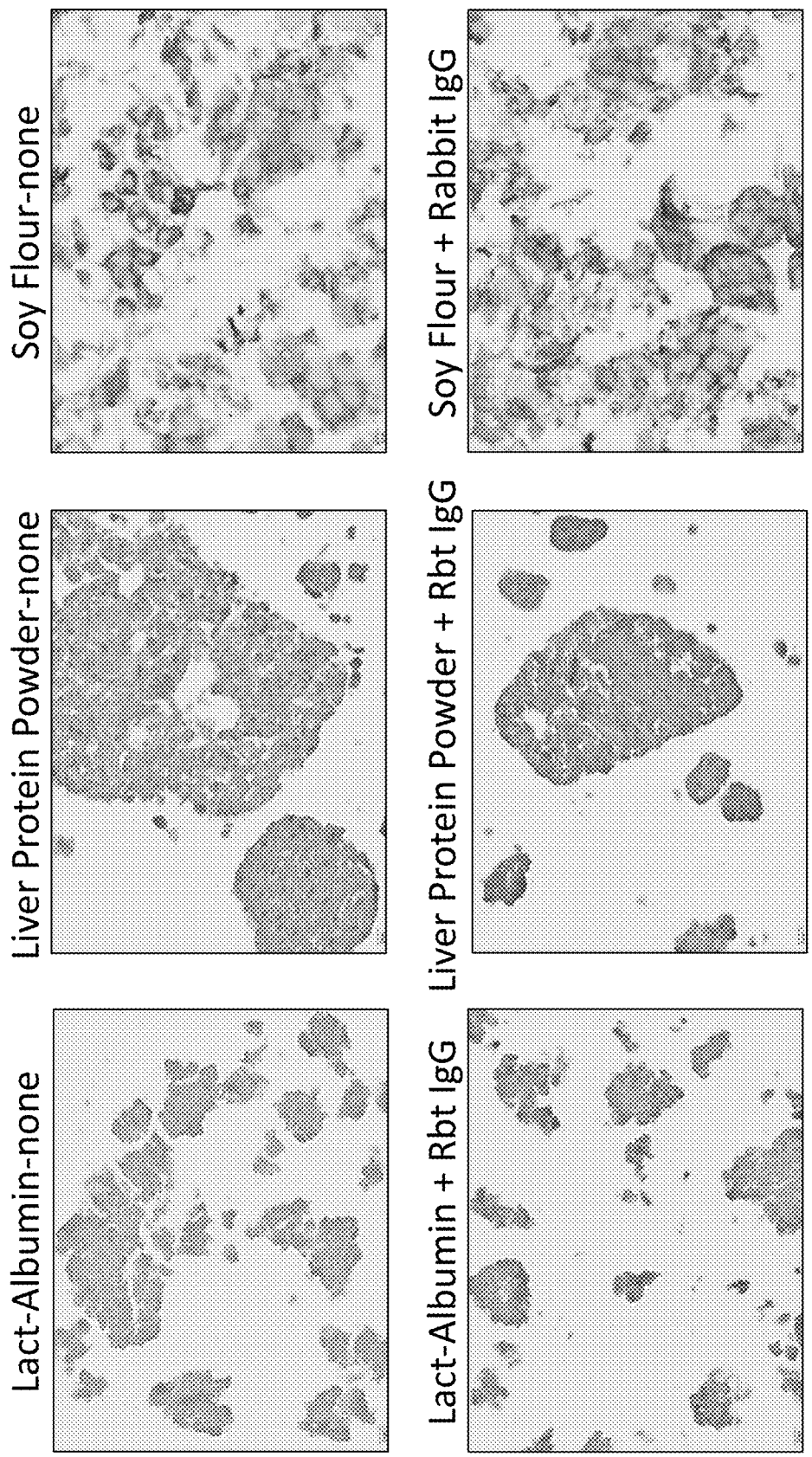
FIG. 9 shows the non-homogeneous gels made from lact-albumin, liver protein powder, or soy flour with (bottom row) or without (top row) rabbit IgG.
Figure 10:
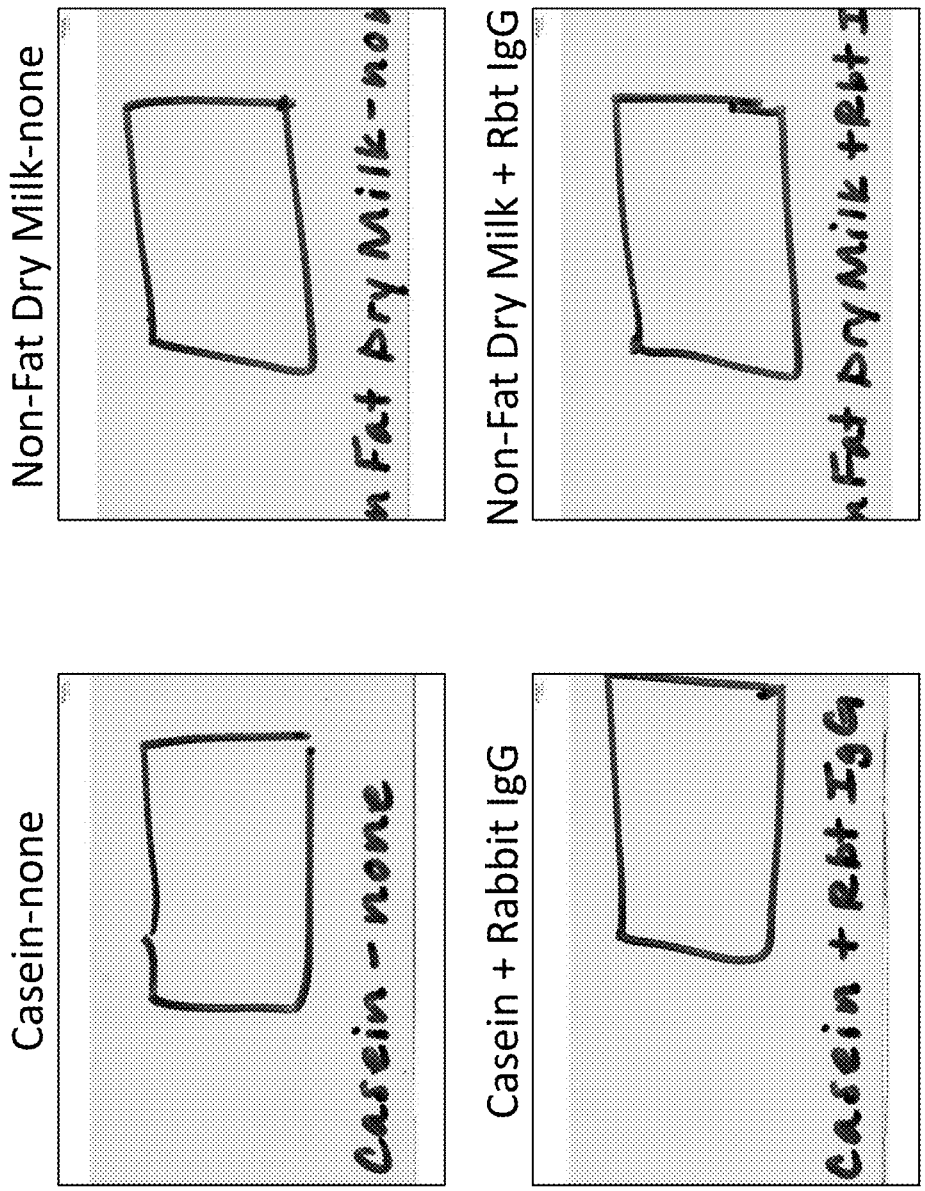
FIG. 10 shows that gels made from casein or non-fat dry milk with (bottom row) or without (top row) rabbit IgG did not adhere to glass slides for IHC staining.

Additional substrate proteins were tested for their ability to form gels suitable for IHC staining, e.g., by forming a homogeneous gel that allows for IHC staining and adheres to a glass IHC slide. As shown in FIG. 8, in addition to BSA, egg white protein or a mixture of egg white proteins and gelatin formed gels that exhibit specific IHC staining (in this case, after the gels containing a rabbit IgG antibody sample were stained with an anti-rabbit secondary antibody) with low non-specific staining (as seen after staining a gel lacking rabbit IgG with an anti-rabbit secondary antibody). In contrast, gels generated from lact-albumin, liver protein powder, or soy flour failed to generate a homogenous gel (FIG. 9). Gels generated from casein or non-fat dry milk failed to adhere to IHC slides (FIG. 10). A description of each gel substrate and the material resulting from attempted gel formation is provided in Table A.

TABLE A

Protein gels made from various substrates.

| Media | |
|---|---|
| BSA 25% | S |
| Casein 10% | White ppt formed after addition of 37% formaldehyde; Histogel ™ aided in pellet formation; 100 mM NaOH was added dropwise to bring the pH to 8.0, with agitation as required to form solution |
| Lact-Albumin 25% | L; Histogel ™ aided in pellet formation |
| Soybean Flour 25% | S |
| Dried Liver Protein Powder | L; Histogel ™ aided in pellet formation |
| Non Fat Dry Milk 25% | L; Histogel ™ aided in pellet formation |
| Lysozyme | S (after 24 h RT clear, semisolid and "sticky"; after an additional 6 hr in 10% NBF at RT, the sample was opaque at the periphery and solid) |
| Gelatine 10% | S (section difficult but stayed on slide through Target antigen retrieval) |
| Egg White protein 25% | S |

S = solid gel
L = liquid

In summary, BSA, egg white protein(s), and gelatin provided gels amenable for specific IHC staining. Other protein substrates either failed to form a homogeneous gel or failed to adhere to slides during IHC processing.

Example 4: Detection of Antigen in Gels

The synthetic IHC control concept described above was further analyzed using proof of concept applications relevant to research and clinical use, including IHC assay calibration and quality control.

Methods
Peptides and Proteins

Peptides were synthesized at >95% purity by New England Peptide (Gardner, Mass.). Amino acids 41-54 of the human BCL2 protein (UniProt P10415) were extended at the N-terminus by four amino acids including acetylated tyrosine to facilitate cross-linking with formaldehyde, and a spacer sequence, GSG. The C-terminus included a GSG spacer sequence followed by cysteine-amide to facilitate cross-linking with formaldehyde (Metz, B. et al. (2004) J. Biol. Chem. 279:6235-6243); Toews, J. et al., (2008) Anal. Chim. Acta 618:168-183) or sulfhydryl-reactive reagents. The entire 22 amino acid peptide sequence is Ac-YGSG-GAAPAPGIFSSQPGGSGC-amide (SEQ ID NO:1). Additional peptides were synthesized containing sequences from the human MYC protein (UniProt P01106): Ac-YGSGNRNYDLDYDSVQPYFYGSGC-amide (amino acids 9-24; SEQ ID NO:2); Ac-YGSGDSVQPYFYCDEEENFYGSGC-amide (amino acids 17-32; SEQ ID NO:3); Ac-YGSGQQQSELQP-PAPSEDIWGSGC-amide (amino acids 35-50; SEQ ID NO:4); Ac-YGSGFELLPTPPLSPSRRSGGSGC-amide (amino acids 53-63: SEQ ID NO:5). A negative control peptide containing 13 amino acids from the first exon of human MCL1 (UniProt Q07820) was synthesized with the same N- and C-terminal sequence extensions described above. For some experiments, arginine, serine or tyrosine replaced the N- and C-terminal amino acids in the peptides described above. Lyophilized peptides were dissolved in a minimal volume of distilled water, DMSO or dimethylformamide. The C-terminal 301 amino acids (amino acids 650 to 950) of the Kinase Suppressor of RAS 2 (KSR2; Uniprot Q6VAB6) protein was expressed as a 701 amino acid N-term

[His]$_6$ tagged, maltose binding protein (amino acids 9-399) fusion construct. The fusion protein was expressed as a baculovirus construct in *Trichoplusia ni* Tni Pro insect cells (Expression Systems; Davis, Calif.), then purified by sequential nickel-nitrilotriacetic acid affinity, amylose affinity and Sepharose 5200 size exclusion chromatography. Purified mouse IgG1 clone MOPC-31 C (BD Pharmingen, San Jose, Calif.), rat IgG1 clone R3-34 (BD Pharmingen, San Jose, Calif.) and rabbit IgG clone DA1E (Cell Signalling Technology, Danvers, Mass.) were obtained commercially. Bovine serum albumin (BSA; Ultra Pure) was purchased from Cell Signaling Technology (Danvers, Mass.). Food-grade gelatin and dried egg whites were from Knox (Oakbrook, Ill.) and Judees Gluten Free (Columbus, Ohio), respectively.

Protein Matrix Gels

Unless otherwise noted, 0.5 mL of solution containing the desired antigen in 25% (w/v) BSA/phosphate-buffered saline (PBS) was mixed in a 1.5 ml microfuge tube with an equal volume of 37% formaldehyde (Electron Microscopy Sciences; Hatfield, Pa.), heated for 10 minutes at 85 C to coagulate the solution, then fixed overnight at room temperature. The final reagent concentrations were 12.5% (1.8 mM) BSA and 18.5% (6.2 M) formaldehyde. Peptide antigens had final concentrations of $2.5 \times 10^{-8}$M to $2.5 \times 10^{-4}$ M in the fixed gels. Gels containing naïve mouse, rat and rabbit IgG had a final concentration of 0.1 mg/ml ($6.7 \times 10^{-7}$M) IgG. The human [His]$_6$-MBP-KSR2 fusion protein had a final gel concentration of 0.5 mg/ml ($6.3 \times 10^{-6}$M).

In tests of alternative fixation protocols, formalin-free zinc fixative (Cat. number 552658, BD Pharmingen; San Jose, Calif.) was used in place of 37% formaldehyde and NBF in the protocols above. In other experiments, antigen in 25% BSA in PBS was solidified by heating for 10 minutes at 85 C in the absence of formaldehyde. The solidified gel was then transferred to 10% neutral buffered formalin (NBF; VWR International, LLC, Radnor, Pa.), 4% paraformaldehyde (PFA; VWR International, LLC, Radnor, Pa.), or zinc fixative for overnight fixation at room temperature.

Tissue Microarray (TMA) Construction

Tissue microarrays (TMA) were constructed using a TMA Grand Master tissue microarrayer (3DHISTECH, Budapest, Hungary). Duplicate 1 mm diameter cores were punched from donor paraffin blocks containing the desired protein gels, then transferred to recipient paraffin blocks. Completed recipient TMA blocks were heated at 37 C overnight, then at 70 C for 10 minutes, before being cooled and sectioned.

IHC Staining

Primary antibodies used were mouse anti-human BCL2 clone 124 (Ventana Medical Systems; Tucson, Ariz.), rabbit anti-human BCL2 clone EPR17509 (Abcam; Cambridge, Mass.), rabbit anti-human BCL2 clone SP66 (Ventana Medical Systems, Tucson, Ariz.), rabbit anti-human BCL2 clone E17 (Abcam, Cambridge, Mass.), rabbit anti-human MYC clone Y69 (Ventana Medical Systems, Tucson, Ariz.) and rabbit anti-human MCL1 clone SP143 (Ventana Medical Systems, Tucson, Ariz.). The Fluidigm EPR17509-$^{146}$Nd antibody was purchased from Fluidigm (South San Francisco, Calif.). A panel of 27 mouse hybridoma antibodies to the [His]$_6$-MBP-human fusion protein was generated at Chempartner (Shanghai, China). Biotinylated donkey anti-rabbit, rat and mouse secondary antibodies were purchased from Jackson Laboratories. Staining protocol details are summarized in Table 1.

TABLE B

IHC protocols.

| Target Antibody | Antibody | Antibody Concentration (microg/ml) | Machine | Conditioning time, temp | Antibody incubation (time, temp) | Detection |
|---|---|---|---|---|---|---|
| BCL2 (DAB) | 124 | RTU[1] | Ventana Benchmark XT | CC1 standard (16 min, 37° C.) | 16 min 37° C. | UltraView DAB |
| BCL2 (IF) | 124 | RTU | Ventana Discovery ULTRA | CC1 standard (64 min, 37° C.) | 16 min 37° C. | Discovery RED610 Kit |
| BCL2 (Dual IF) | 124 | RTU | Ventana Discovery ULTRA | CC1 standard (64 min, 37° C.) | 16 min 37° C. | Discovery FAM Kit |
| BCL2 (DAB) | EPR17509 | 0.25 | Ventana Discovery XT | CC1 standard (64 min, 37° C.) | 60 min 37° C. | OmniMap DAB 16 min |
| BCL2 (DAB) | E17 | 2.12 | Ventana Discovery XT | CC1 mild | 32 min 37° C. | OptiView DAB |
| BCL2 (DAB) | SP66 | RUT | Ventana Discovery XT | CC1 standard | 16 min 37° C. | OptiView DAB |
| BCL2 (MS) | EPR17509-$^{146}$Nd | 1, 5, 10 | Manual | Taget pH 6 20 min | Overnight 4° C. | Mass spectrometry |
| MYC (DAB) | Y69 | RTU | Ventana Benchmark XT | CC1 64 min | 16 min 37° C. | OptiView DAB |
| MYC (Dual IF) | Y69 | RTU | Ventana Discovery ULTRA | CC1 64 min | 16 min 37° C. | Discovery Cy5 Kit |
| MCL1 (DAB) | SP143 | 5 | Ventana Benchmark XT | CC1 standard | 32 min 37° C. | OptiView DAB 8 min |
| KSR2 (DAB) | Several hybridoma antibodies | 5 | Dako Universal Autostainer | Taget pH 6 20 min | 1 hour RT | ABC-HRP and DAB |
| Rabbit IgG (DAB) | Polyclonal | 10 | Dako Universal Autostainer | Taget pH 6 20 min | 1 hour RT | ABC-HRP and DAB |
| Rat IgG1 (DAB) | Polyclonal | 10 | Dako Universal Autostainer | Taget pH 6 20 min | 1 hour RT | ABC-HRP and DAB |
| Mouse IgG1 (DAB) | Polyclonal | 10 | Dako Universal Autostainer | Taget pH 6 20 min | 1 hour RT | ABC-HRP and DAB |

RTU = ready to use (antibody concentration not disclosed by vendor).

Four micron paraffin sections were deparaffinized and rehydrated in xylene and graded alcohols. Staining was performed on the Ventana Benchmark XT, Ventana Discovery XT, Ventana Benchmark Ultra XT instruments (Ventana Medical Systems, Tucson, Ariz.) or the Dako Universal Autostainer (Agilent, Santa Clara, Calif.). Sections were pretreated with Cell Conditioning Solution 1 (CC1) (Ventana Medical Systems, Tucson, Ariz.) or Target Retrieval Solution, pH6 (Ready-To-Use) (Dako-Agilent Technologies, Santa Clara, Calif.) depending on the optimized antibody protocol. Slides stained on the Ventana instruments were counterstained with Ventana hematoxylin and bluing reagents (Ventana Medical Systems, Tucson, Ariz.) for 4 minutes each. Slides stained on the Dako Universal autostainer were counterstained in Mayer's hematoxylin (Rowley Biochemical, Danvers, Mass.) and Richard-Allen Scientific Bluing Reagent (Thermo Fisher Scientific, Waltham, Mass.) for 1 minute each. Stained sections were dehydrated in graded alcohols to xylene before coverslipping. Immunofluorescent slides were coverslipped with Prolong Gold mounting media (Life Technologies, Carlsbad, Calif.).

Fluidigm Staining Procedure

Sections were baked at 70 C for 30 min, deparaffinized, rehydrated in descending EtOH series and pretreated with Target Retrieval Solution, pH6 (Dako-Agilent Technologies, Santa Clara, Calif.), blocked for 30 minutes in 10% donkey serum, 3% BSA in PBS, then incubated with $^{146}$Nd-EPR17509 in blocking buffer. Slides were incubated without coverslip at 4° C. overnight in a humidified closed container, then rinsed 3 times in PBS, post-fixed in 2% Glutaraldehyde/PBS for 5 min at 20 C slides, rinsed in ddH$_2$O, dehydrated in increasing EtOH series, air dried and stored at 20 C until imaging.

Imaging Mass Spectrometry Analysis

TMA cores stained with $^{146}$Nd-labeled EPR17509 were analyzed in the Fluidigm Hyperion imaging mass spectrometer (South San Francisco, Calif.) by defining ablation regions of interest (ROIs) of 150 microns square in each TMA core. The integrated ion counts for each ROI were converted to antibody mass using antibody standard data as described below.

Control aliquots of 1, 5 and 10 micrograms/ml $^{146}$Nd-labeled EPR17509 were prepared in 10% donkey serum in 3% BSA in PBS. One microliter of each antibody sample was spotted on a glass slide and air dried before being ablated in the Hyperion machine (UV laser intensity=3). The integrated ion count for each antibody spot was used to calibrate the ion counts measured in ROIs from stained TMA cores.

Digital Image Acquisition and Analysis

Whole-slide brightfield images were acquired at a scanning resolution of 0.46 microns/pixel using the Hamamatsu (Bridgewater, N.J.) Nanozoomer-XR digital slide scanner equipped with a 20× 0.75 NA objective lens. Brightfield imaging was performed in semi-automatic batch mode. The scan area and focus points were manually created for each slide prior to automated high resolution whole-slide imaging. Immunofluorescence whole-slide images were acquired using the Nanozoomer-XR or 3D Histech Pannoramic 250 scanner (using a 20× 0.8 NA objective lens with a resolution of 0.33 microns/pixel). On the Nanozoomer-XR system, illumination power of the fluorescent module was set at 50% and immunofluorescence signal was captured using a TRITC (antibody signal at 1× exposure, 3.4 ms photon collection, 1× gain), DAPI (autofluorescence at 2× exposure, 6.8 ms photon collection, 2× gain) and CFP filter (autofluorescence at 4× exposure, 13.6 ms photon collection, 2× gain). Acquisition on the Pannoramic 250 system was performed using a CY5 (antibody signal at 10 ms exposure), FITC (antibody signal at 2 ms exposure), DAPI (autofluorescence at 40 ms exposure) and CFP filter (autofluorescence at 200 ms exposure). Image analysis was performed using Matlab version 9.3. Regions of interest (ROI) on brightfield images were manually created and edited to exclude areas of the gel that had artifacts or were torn. Small holes or tears within the ROI were excluded using manual color thresholds. ROI for immunofluorescent images were either manually created or automatically generated when sufficient signal above background of the gel is available from the autofluorescence image by thresholding (on either the DAPI or CFP channel) and morphological filtering. ROIs were transferred onto images acquired in the antibody-fluorochrome channel for intensity measurement. Average grayscale intensity was calculated in 8-bit depth for both brightfield and fluorescent images. Plotted Y-axis values for average brightfield pixel intensity represent 255 minus average pixel grayscale intensity. Digital slide scan images are presented without alteration of the original intensity or contrast. Staining intensity profile quantification on lines drawn across donor block sections were assessed using the Analyze/Plot Profile function in ImageJ (version 1.52a; Wayne Rasband, imagej.nih.gov/ij).

Statistical Analysis

Graphing was done with Prism GraphPad (version 7). Signal intensity data, corrected for glass slide background, were plotted vs. the $\log_{10}$ of the formulated antigen concentration. Curve fitting used the variable slope 4-parameter model constrained so that the bottom of the fitted curve was equal to the mean intensity of the no-antigen cores for each assay, reported in the tables associated with each graph as "Bottom". The other parameters reported in the tables [signal maximum, span, antigen concentration at half-maximum signal (ACHM), and Hill slope], were calculated by the software.

Results

As demonstrated in Examples 1-3, when incorporated into protein gels, synthetic peptides encoding an antibody target epitope can be detected using routine immunohistochemical and immunofluorescent procedures. Donor blocks containing target peptides had relatively homogenous antigen distribution when assessed by chromogenic assays (FIGS. 11A-11D). A tissue microarray (TMA) can be constructed containing the desired antigens in a range of antigen concentrations. FIGS. 12A-12E show a TMA composed of duplicate cores containing either no added peptide, serial dilutions of a negative control peptide from the human MCL1 protein, or dilutions of peptide encoding amino acids 41-54 of the BCL2 protein. Parallel sections of this TMA were stained with four anti-BCL2 antibodies: clone 124, raised against the same peptide sequence used in the target peptide; SP66 and E17, both raised against peptide antigens C-terminal to the sequence in the reagent (Adam, P. et al. (2013) *Human Pathology* 44:1817-1826; www.abcam.com/bc12-alpha-antibody-sp66-n-terminal-ab93884.html); and EPR17509, raised against an undisclosed BCL2 peptide antigen (www.abcam.com/BCL2-antibody-epr17509-hrp-ab209039.html). Separate slides were stained using chromogenic (all antibodies) and immunofluorescent (for clone 124 only) methods.

Figure 13A:
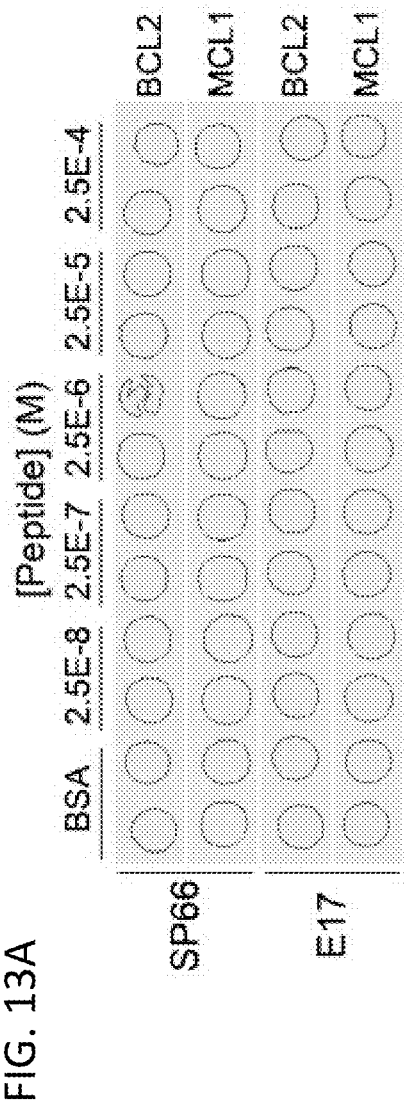
FIG. 13A shows sequential sections of a single tissue microarray contain BSA gel cores having no added peptide (BSA), peptide encoding amino acids 41-54 of the BCL2 protein, or a negative control peptide from the human MCL1 protein. Two slides were stained chromogenically for BCL2 antigen using anti-BCL2 clone SP66 or clone E17.
Figure 13B:
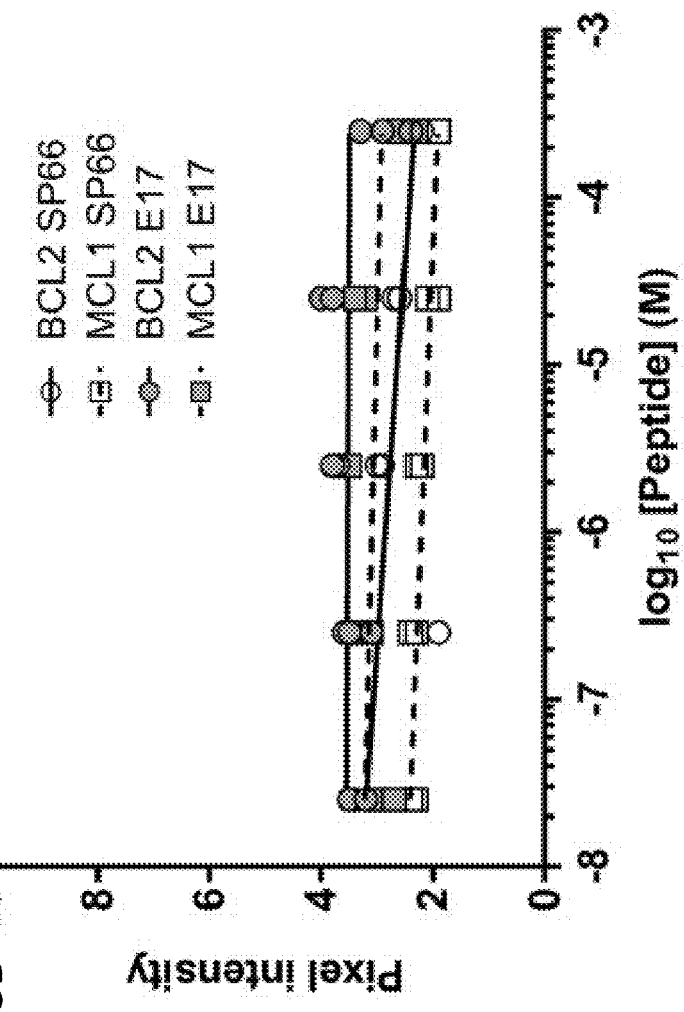
FIG. 13B shows quantification of the images illustrated in (FIG. 13A).

As expected, SP66 and E17 did not react detectably with any core in the sections from this TMA (FIGS. 13A & B). With both clone 124 and EPR17509, the signal in the TMA cores increased with increasing concentration of BCL2 peptide (FIGS. 12A-12C), consistent with a specific interaction between the antibody and antigen in the cores.

Digital image quantification allowed a more precise evaluation of the data (FIG. 12D). The fitted curves and the associated parameters reported in FIG. 12E quantify the minimum and maximum signal intensity, the dynamic range, the antigen concentration at which the signal is half-maximal (ACHM), and the steepness of the antigen concentration vs. signal intensity curve in this range (Hill Slope). With the conditions tested here, non-specific signal in cores containing no added peptide was 2.7% of the maximum detectable signal in the clone 124 chromogenic assay, 1000-fold lower than this in the fluorescent clone 124 assay, and 23% in the EPR17509 assay. On the other hand, for EPR17509, the ACHM value, which reflects the relative sensitivity of the assay, was approximately 8-fold lower (i.e., more sensitive) than the ACHM for the chromogenic clone 124 assay, and more than 50-fold lower than the fluorescent clone 124 assay. The immunofluorescent clone 124 assay had a slope 50-75% steeper than either chromogenic assay, reflecting the narrower range of antigen concentration between the threshold of detection and maximum signal.

To assess the reproducibility of the peptide controls in repeated assays, a second BCL2 peptide TMA was constructed using new donor paraffin blocks formulated to have the same target BCL2 peptide concentrations as those used to build the TMA in FIGS. 12A-12E. Replicate sections of this second TMA were stained by two operators, on six separate days in a 6 month interval using the same anti-BCL2 clone 124 chromogenic IHC protocol used in FIGS. 12A-12E. Quantitative digital image analysis of the stained sections showed the signal intensity for each core was highly reproducible (FIGS. 14A-14C; see also FIGS. 3B & 3C).

In parallel experiments, clone 124 was used to stain TMAs containing BCL2 peptide with or without prior antigen retrieval. The results showed that antigen retrieval improved signal strength approximately 6-fold, but was not required for staining (FIGS. 15A-15C).

Example 5: Stability of Peptide Cross-Linking in Gel Matrix

Without wishing to be bound to theory, it is thought that the concentration of peptide that is available to bind antibody is reduced from the formulated value by three parameters: the efficiency of crosslinking the peptide to the protein matrix, the biochemical integrity of the peptide and accessibility of the cross-linked peptide to antibody. Formaldehyde was intended to cross-link BSA sidechains to the target peptides by reaction with the N-terminal tyrosine and C-terminal cysteine included in the peptide sequence. Of the amino acids internal to the BCL2 peptide (A, F, G, I, P, Q, S), only glutamine has been reported to react with formaldehyde (Metz, B. et al. (2004) *J. Biol. Chem.* 279:6235-6243).

To assess the effect of alternative N- and C-terminal amino acids on signal intensity, four variants of the BCL2 peptide were tested. The N-terminal tyrosine was replaced with serine, expected to be minimally reactive with formalin, or with arginine, reported to be 50% more reactive than tyrosine (Metz, B. et al. (2004) *J. Biol. Chem.* 279:6235-6243). Other variants included tyrosine or arginine at both the N- and C-termini. TMA cores containing serial dilutions of each peptide were prepared and stained as described above.

The results showed a significantly higher signal for the peptide with N-terminal arginine ("R-C", FIGS. 16A-16C).

The ACHM for this variant was $4.43 \times 10^{-7}$ M peptide, 6-fold lower than the corresponding value for the original Y-C variant. The other variants showed a range of intensities similar to (S-C) or weaker than (R—R, Y—Y) the original Y-C variant. Notably, variants containing arginine or tyrosine at the N-terminus with cysteine at the C-terminus reacted more strongly than peptides with arginine or tyrosine at both ends.

Example 6: Generalizability for Synthetic IHC Controls

Next, experiments were undertaken to establish whether peptides containing epitopes for proteins other than BCL2 would react in a similar fashion. The anti-MYC antibody Y69 is reported to bind an epitope in the N-terminal 100 amino acids of the human MYC protein (www.abcam.com/c-MYC-antibody-y69-ab32072.html). Candidate epitopes from this region were incorporated into BSA gels as described above and tested for Y69 binding.

A peptide containing MYC amino acids 9-24 reacted strongly with the antibody, whereas other peptides reacted only weakly (aa 17-32) or not at all (aa 35-50 and aa 53-68) (FIG. 17A). A TMA was constructed containing duplicate cores, in the range of concentrations described earlier, of both the MYC aa 9-24 peptide and the BCL2 peptide. Chromogenic detection using anti-BCL2 clone 124 and anti-MYC clone Y69 showed a range of signal intensity, with no cross-reactivity to the non-target peptide (FIGS. 17B & 17C). Quantification of the resulting data (FIG. 17D) showed the MYC protocol had a 4-fold lower ACHM than does the BCL2 protocol, with similar dynamic range and HillSlope parameters (FIG. 17E).

Dual immunofluorescent detection on the same TMA used in FIGS. 17A-17E was done using serial incubation with both anti-BCL2 and anti-MYC primary antibodies appropriate detection reagents (FIGS. 18A-18C). Qualitative results (FIGS. 18A & 18B) showed the expected specificity with no cross-reactivity between either antibody and the non-target peptide. Isotype controls used in place of antigen-specific primary antibodies resulted in no signal. Quantification of the resulting fluorescent data shows increased HillSlope parameters and increased replicate variability under the conditions tested, relative to the chromogenic protocol.

These results confirm the broadly applicable utility of peptide antigens as IHC controls using diverse epitopes and detection protocols.

Example 7: Limit of Detection (LOD) and Reproducibility

The quantitative data obtained allowed a determination of the limit of detection (LOD) and reproducibility of the clone 124 BCL2 IHC assay.

The experiments illustrated in FIGS. 12A, 14A-14C, 15A, & 17B represent 10 independent analyses, each with duplicate TMA cores containing no target peptide (blank) and 6 concentrations of BCL2 peptide. FIGS. 19A & 19B and Table C summarize the data. For each experiment, the means of duplicate TMA cores at each peptide concentration were used in the calculation. Values are pixel intensities of the TMA cores corrected for the background intensity of the glass slide (19.2+/−0.5 units).

TABLE C

BCL2 clone 124 IHC assay aggregate data

| | BCL2 peptide concentration (as formulated; M) | | | | | |
|---|---|---|---|---|---|---|
| | BSA only | 2.5E-08 | 2.5E-07 | 2.5E-06 | 2.5E-05 | 2.5E-04 |
| n = | 10 | 10 | 10 | 10 | 10 | 10 |
| Intensity Mean[1] | 4.8 | 6.1 | 18.0 | 104.8 | 202.3 | 211.6 |
| St. Dev. | 1.9 | 2.8 | 4.6 | 20.0 | 11.7 | 5.2 |
| CV | 40% | 46% | 26% | 19% | 5.8% | 2.5% |
| t-test vs. next lowest peptide conc. | NA | 2.8E-1 | 4.6E-6 | 1.1E-7 | 1.5E-9 | 4.0E-2 |

According to an accepted clinical laboratory convention (Armbruster and Pry, 2008), the limit of blank (LOB; = $mean_{blank}+1.645 \times SD_{blank}$) for these data is 8.0 units, and the limit of detection ((LOD; =LOB+1.645×$SD_{low-positive\ sample}$) is 16 units, corresponding to $2.3 \times 10^{-7}$ M peptide. This concentration equates to a formulated antigen density of approximately 140 molecules per cubic micron of gel.

Consistent with these calculations, results of two-tailed t-test comparisons of data for cores with increasing BCL2 peptide concentrations (Table C) showed that cores with $2.5 \times 10^{-8}$ M peptide (below the calculated LOD) are not significantly different from cores lacking peptide, whereas cores with $2.5 \times 10^{-7}$ M peptide and higher (above the calculated LOD) are statistically different adjacent cores. Notably, signal in cores containing the two highest peptide concentrations are statistically different, despite the fact that the subjective intensity of these cores is similar.

Example 8: Use of Synthetic IHC Controls for Antibody Validation

As described in Example 1 above (see FIGS. 5A-5D), another protein was incorporated into a BSA gel and used to evaluate antibodies generated from hybridoma clones. In this case, a peptide including the C-terminal 301 amino acids (i.e., amino acids 650-950) of human KSR2 was used. The results described above demonstrate that the synthetic IHC controls approach provides a useful method of identifying antibodies suitable for IHC analysis of a target of interest, a process in which hundreds to thousands of candidate antibodies are typically screened in order to identify a small handful (e.g., 2-5) of leads for further characterization.

Figure 20A:
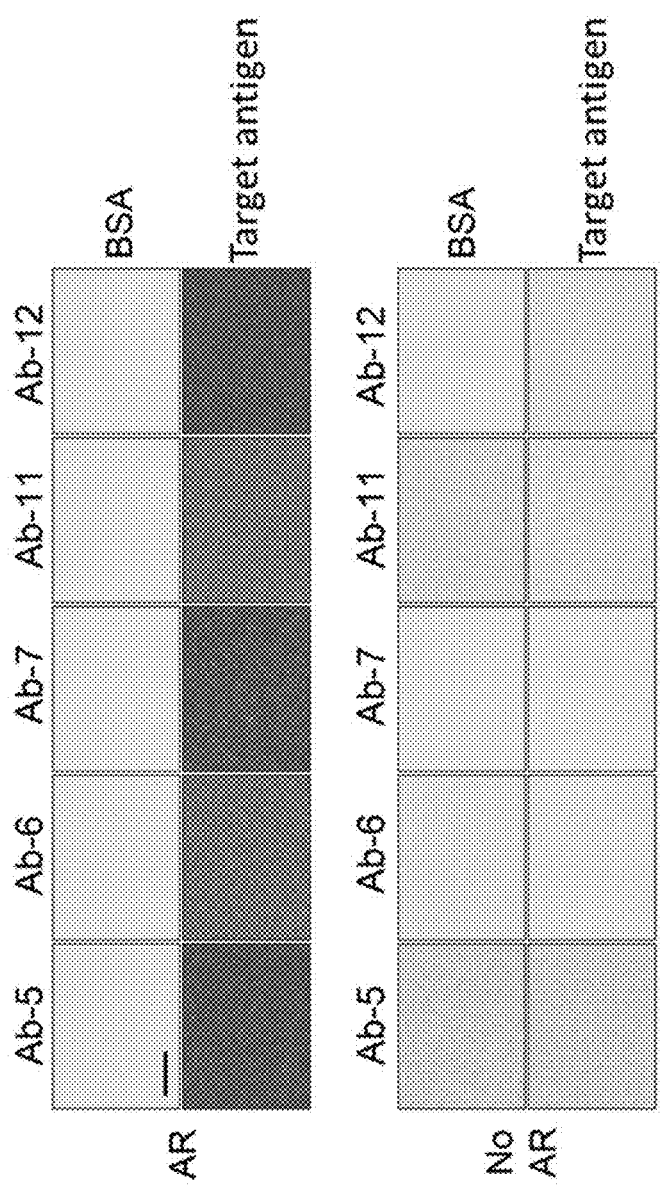
FIGS. 20A & 20B test the antibodies screened in FIGS. 5A-5D against human KSR2 for staining with and without antigen retrieval. Images in FIG. 20A show sections of BSA gel containing no protein (BSA) or $6.3 \times 10^{-6}$ M protein of interest stained with a selection of mouse antibodies with (AR) or without (No AR) prior antigen retrieval.
Figure 20B:
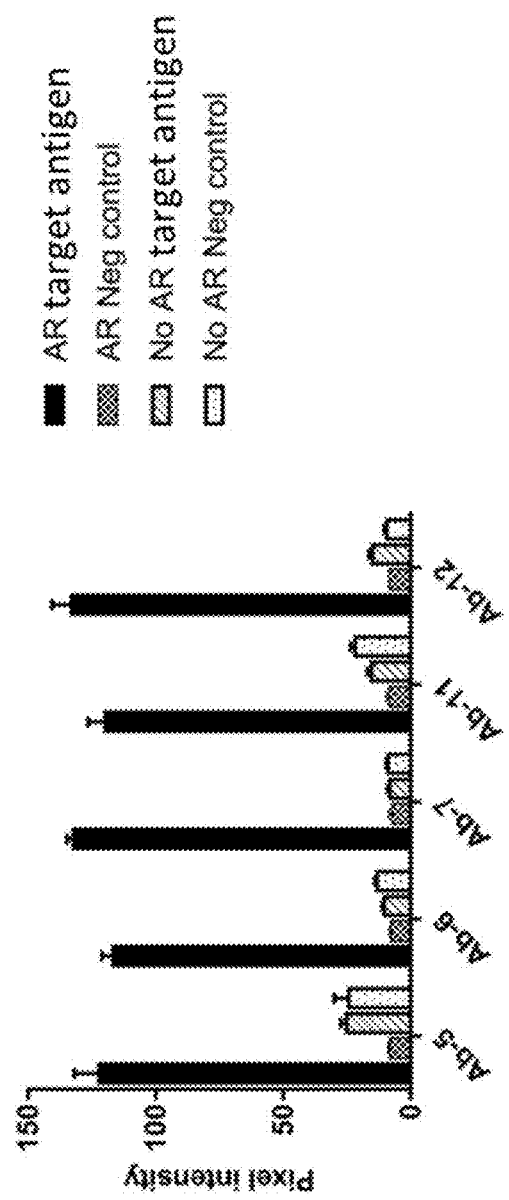

Candidate antibodies were further tested for reactivity against the antigen without prior antigen retrieval. For each antibody, antigen retrieval was required for detectable reactivity (FIGS. 20A & 20B). This contrasts with the results with BCL2 peptides described in Example 4, for which antigen retrieval improved signal strength approximately 6-fold, but was not required for detectable reactivity (FIGS. 15A-15C).

Figure 21A:
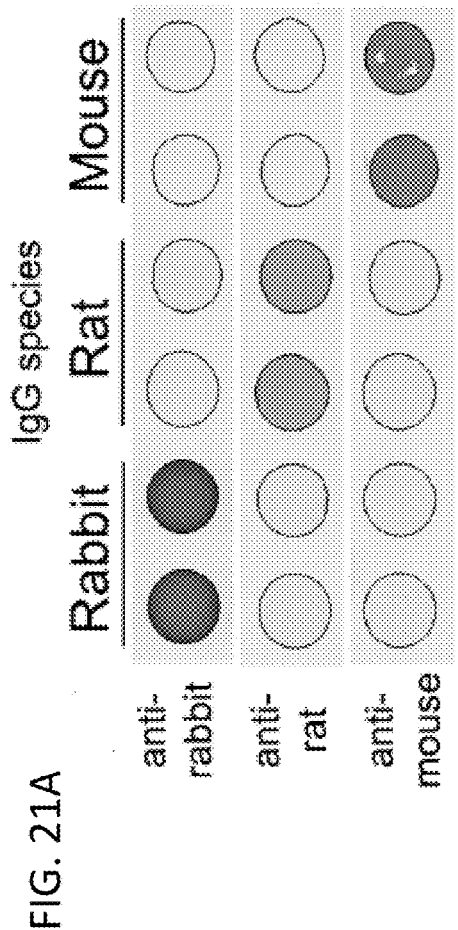
FIGS. 21A & 21B show BSA gels with mouse, rat and rabbit IgG.
Figure 21B:
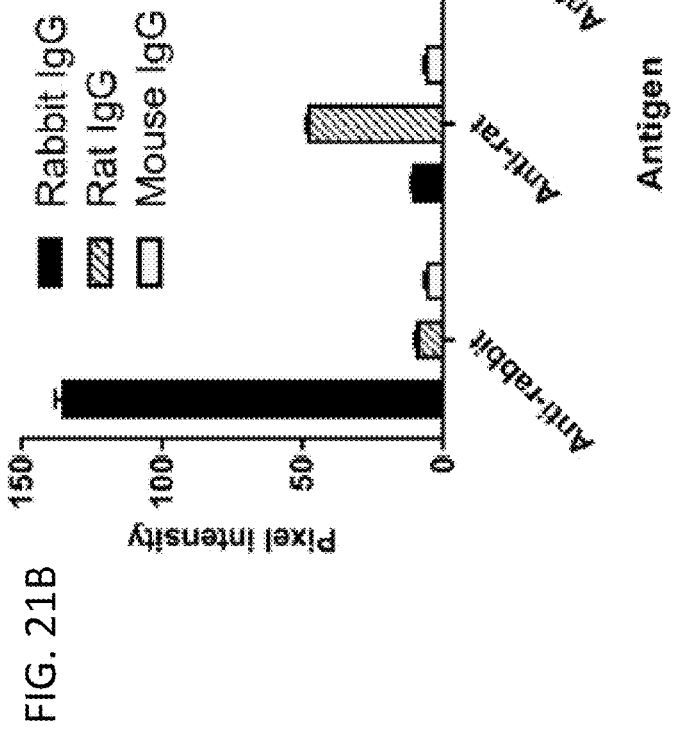

As a test of full length proteins, rabbit, rat and mouse full-length immunoglobulins (IgG; (0.1 mg/ml; $6.7 \times 10^{-7}$ M) incorporated into BSA gels were prepared and used as technical controls for IHC assays employing biotinylated donkey anti-rabbit, anti-rat and anti-mouse secondary antibodies in detection steps. The results show the expected signal and specificity of the anti-rabbit, anti-mouse and anti-rat secondary antibodies (FIGS. 21A & 21B). As shown in FIGS. 21A & 21B, incorporated rabbit IgG detected with donkey anti-rabbit IgG secondary antibody shows 136 units of pixel intensity. Assuming quantitative retention of the added rabbit IgG, 1 cubic micron ($10^{15}$ L) of this sample contains $6.7 \times 10^{-22}$ moles, or about 400 detectable molecules of rabbit IgG.

Example 9: Testing Alternative Fixatives for Making Gels

Because some epitopes are rendered non-reactive by formalin-containing fixatives, a commercially available formalin-free zinc fixative was tested as an alternative to the 37% formaldehyde used in previous experiments.

Donor blocks containing BCL2 and MYC peptides in BSA gels were fixed with either formalin or zinc-based fixatives with heating to 85 C (FIGS. 22A-22C). For both BCL2 and MYC peptides, the signal was approximately 10-fold stronger with formaldehyde fixation than with zinc fixation during heating. The loss of signal strength correlated with heating in the presence of zinc.

Figure 23A:
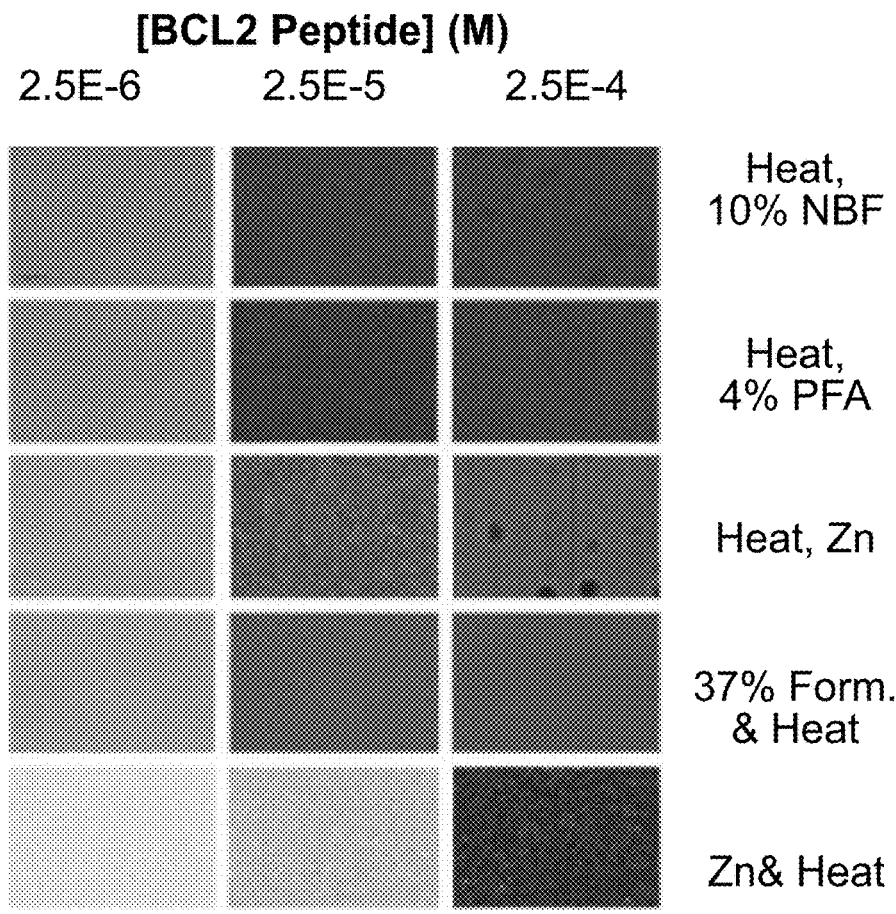
FIGS. 23A & 23B show the results of testing alternative fixatives.
Figure 23B:
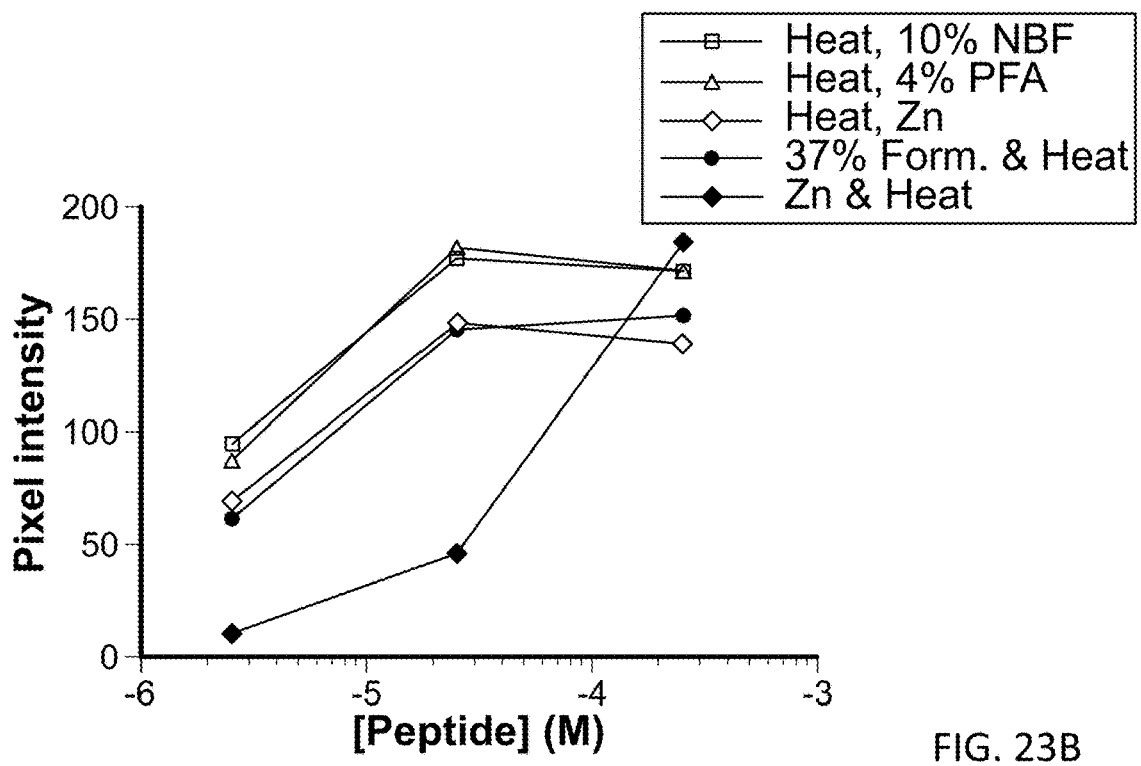

Alternative procedures in which BSA-antigen mixtures were heated to 85 C in the absence of fixative, followed by fixation at room temperature in a variety of fixatives (4% paraformaldehyde, neutral-buffered formalin, zinc-containing formalin-free fixative) resulted in comparable signal to the standard protocol described above (FIGS. 23A & 23B). This demonstrates that the technique can accommodate a variety of fixatives, potentially broadening the range of epitopes and antibodies that could be used.

Example 10: Imaging Mass Cytometry Analysis

In the experiments reported above, the number of chromogen or fluorochrome molecules deposited for each molecule of antibody bound is unknown, so the absolute concentration of epitope detected cannot be calculated. To avoid this limitation, a more quantitative direct detection procedure using the Hyperion mass spectrometry-based imager was tested.

Sections of the BCL2 peptide TMA were stained with [146]Nd-labeled anti-BCL2 antibody EPR 17509, then analyzed by ultraviolet laser ablation and quantitative mass spectrometry. The TMA sample quantified was typically an area 150 microns square by 4 microns thick, containing $9 \times 10^4$ cubic microns. The results showed a graded signal that increases as the BCL2 peptide concentration in the target increases (FIGS. 24A-24C). The EPR17509 antibody signal in cores containing no peptide or in cores containing the negative control MCL1 peptide was less than 3% of the maximum signal.

The correlation between measured ion counts and antibody concentration was determined by analyzing known amounts of [146]Nd-labeled antibody spotted directly onto glass slides. The resulting calibration data (Table D) showed a ratio of approximately 340 antibody molecules per $^{146}$Nd ion detected.

TABLE D

Antibody ion quantification

| $^{146}$Nd Ab mass | $^{146}$Nd Ab molecule number | $^{146}$Nd Ion counts from control spot | Ab molecule per $^{146}$Nd ion count | Ion count fold change vs. 1 ng |
|---|---|---|---|---|
| 1 ng | 4E9 | 1.57E7 | 254 | NA |
| 5 ng | 2E10 | 8.09E7 | 247 | 5.17 |
| 10 ng | 4E10 | 7.91E7 | 506 | 5.03 |

By comparing the amount of BCL2 peptide formulated in each TMA core sample with the amount of $^{146}$Nd-labeled anti-BCL2 antibody measured, the fraction of BCL2 peptide that was detectable in the TMA cores was determined. Results (Table E1 and Table E2) showed that the amount of detectable BCL2 peptide increased with increasing peptide concentration, as expected.

TABLE E1

Antibody bound by BCL2 peptide-containing cores.

| BCL2 peptide concentration | Integrated ion counts (per 150 micron square ROI) | | | Average ion count (st. dev.) |
|---|---|---|---|---|
| | 10 ug/ml Ab | 5 ug/ml Ab | 1 ug/ml Ab | |
| 2.50E−04 | 87362 | 35264 | 59146 | 58174 |
| | 87954 | 37184 | 42132 | (26532) |
| 2.50E−05 | 39355 | 16554 | 32175 | 32635 |
| | 48711 | 15118 | 43899 | (14854) |
| 2.50E−06 | 7834 | 4291 | 7747 | 6399 |
| | 6911 | 3906 | 7703 | (2000) |
| 2.50E−07 | 1549 | 1374 | 1981 | 1739 |
| | 1757 | 1395 | 2377 | (404) |
| 2.50E−08 | 1233 | 976 | 1452 | 1310 |
| | 1723 | 1067 | 1412 | (251) |
| None | 979 | 1080 | 1354 | 1177 |
| | 1155 | 1180 | 1311 | (139) |

TABLE E2

Antibody bound by BCL2 peptide-containing cores.

| BCL2 peptide concentration | Ion count above background | Moles $^{146}$[Nd] Ab detected per ROI | Moles peptide formulated in ROI | $^{146}$[Nd] Ab/ peptide | ttest group vs background |
|---|---|---|---|---|---|
| 2.50E−04 | 56997 | 3.20E−17 | 2.25E−14 | 0.14% | 2.26E−03 |
| 2.50E−05 | 31459 | 1.76E−17 | 2.25E−15 | 0.78% | 2.80E−03 |
| 2.50E−06 | 5222 | 2.93E−18 | 2.25E−16 | 1.30% | 8.61E−04 |
| 2.50E−07 | 562 | 3.15E−19 | 2.25E−17 | 1.40% | 1.46E−02 |
| 2.50E−08 | 134 | 7.50E−20 | 2.25E−18 | 3.33% | 3.22E−01 |

The results also showed that the proportion of added BCL2 peptide that is detectable decreased as the antigen concentration increased; 1.4% of the added peptide was detectable at $2.5\times10^{-7}$ M, whereas ~0.14% of added peptide was detected at $2.5\times10^{-4}$ M.

CONCLUSIONS

Taken together, the results of Examples 1-10 demonstrate that antigen-containing gels can be created using materials and methods available in any histology laboratory, and can be embedded and sectioned to produce uniformly stained samples. These examples demonstrate that the method is compatible with a variety of fixatives and with detection using chromogenic, immunofluorescent and mass spectrometry-based methods. The choice of possible antigens is limited only by the availability of the target protein or knowledge of the linear epitope sequence. The ability to create synthetic controls of known composition offers the opportunity to more precisely characterize and control routinely used immunohistochemistry protocols, independent of complicating factors inherent in heterogeneous tissue samples and subjective human interpretations.

These results provide proof of concept detection of linear peptide epitopes from BCL2, MYC and MCL1 using antibodies specific to each protein, and further demonstrate detection of full-length IgG and a 301-amino acid human protein. The target epitope concentrations formulated and tested here span four orders of magnitude, from $2.5\times10^{-8}$M to $2.5\times10^{-4}$ M, extending to the upper end of the range of protein concentrations found in tissue. At the high end of this range, average intermolecular distance is less than 20 nM, approaching the distance between the two arms of a full-length IgG molecule (~14 nM). Only very abundant proteins reach this density. The protein concentration used in this procedure is in the range (7-25%) found in many tissues (Cole, J. (2017) *Scientific Reports* 7:44707), and so reproduces some mechanical and biochemical tissue properties.

These results further demonstrate that quantitative parameters relevant to IHC assay performance in tissues—non-specific background, limit of detection, dynamic range, antigen concentration at half-maximum signal and Hill Slope—can be assessed with objectively definable precision in any laboratory with access to a digital slide scanner and basic image analysis capabilities. The results demonstrate that these parameters can vary with different experimental conditions when using one antigen-antibody pair, with different antibodies detecting the same antigen and with different antibody/antigen pairs. For instance, measured ACHM values differed by more than 50-fold in the three assays shown in FIGS. 12A-12E. In a series of 10 replicate experiments with the clone 124 BCL2 assay, the calculated data parameters for maximum signal, dynamic range, log (ACHM) and HillSlope have coefficients of variation of less than 10%, but higher precision may be possible. These experiments used serial 10-fold dilutions of antigens across a physiologic range ($2.5\times10^{-8}$ to $2.5\times10^{-4}$ M), but the precision of ACHM and slope quantification could potentially be improved by including more samples between 10% and 90% of the dynamic range of the assay. Because assay performance can be assessed more objectively and precisely than is possible by subjective human evaluation of tissues or cell pellets, the performance of assays can be tailored more precisely to the clinical need, and more rigorously controlled.

Synthetic controls with a range of antigen concentrations allow IHC staining protocols to be optimized, quantified and controlled over time using a reproducible standard. The concept described here allows quality control of an IHC assay at a level intermediate between the two extremes of assessing the interaction between purified antibodies and antigens under controlled in vitro conditions and assessing antibody reactivity in tissue samples by empirical optimization.

Application of this method to ongoing quantitative immunohistochemical analyses is contemplated. A synthetic antigen gel sample is homogeneous, has a uniform thickness, and contains a known number of epitope molecules, allowing correlation of signal intensity to antigen concentration. An on-slide TMA section including a useful range of epitope concentrations can easily fit adjacent to a diagnostic tissue section, permitting assay technical adequacy, or quantitative image analysis to be assessed on any slide. Because the components and procedures used in this method are completely defined, reagents created in different laboratories should, in principle, be functionally similar. This approach can allow investigators to compare and calibrate protocols used in different laboratories, to communicate more clearly when describing qualitative staining endpoints, and ultimately, to more precisely control of IHC assays used both in research and patient-care decision-making.

Example 11: Synthetic Antigen Gels Made with Poly-Lysine

The above Examples (see, e.g., Example 3) describe substrate proteins tested for their ability to form gels suitable for IHC staining, e.g., by forming a homogeneous gel that allows for IHC staining and adheres to a glass IHC slide. This Example describes testing poly-lysine for antigen/gel matrix formation.

Poly-lysine provides multiple formaldehyde-reactive side chains and is commercially available in a variety of molecular weights ranging from 1-4 kDa up to greater than 300 kDa. A poly-lysine monomer has a formula weight of 128 Da (assuming no salt counterion), so the commercially available poly-lysine molecules include polymers in a range of 8-30 lysine monomers to greater than 2,300 lysine monomers.

As demonstrated above, BSA at 12.5% (final concentration), upon heat denaturation and reaction with formaldehyde, produces a useful matrix in which target antigens can be embedded and cross-linked. BSA at 12.5% is at a concentration of 1.8 mM, assuming a formula weight of 69,293 Da. Each BSA molecule contains 60 lysine side chains. In addition to lysines, each molecule of BSA also contains 26 arginine and 21 tyrosine side chains, each of which can react with some efficiency with formaldehyde. Thus, in a 12.5% BSA gel, there are 60×1.8 mM, or 108 mM, lysine side chains.

A sample of poly-lysine gel matrix based on similar calculations therefore contains approximately 108 mM lysine side chains in the final gel. Assuming a formula weight for a single lysine side chain in a poly-lysine polymer of 128 Da, the final concentration of poly-lysine in a gel is approximately 14 mg/mL. A higher weight per volume is used if the commercial poly-lysine contains a counterion salt. For example, poly-lysine*HBr salt has a formula weight of 209 g/mol. The desired final concentration of poly-lysine is achieved by mixing equal volumes of 216 mM poly-lysine solution (approximately 28 mg/mL pure, 45 mg/mL as HBr salt) with concentrated formaldehyde stock (37%). Without wishing to be bound to theory, it is thought that lysine side chains in the sample cross-link with each other, within and/or between poly-lysine strands, to form a gel.

Poly-lysine solution at the concentration(s) described above are mixed with 37% formaldehyde (and optionally an antigen of interest) and heated to 85° C. for 10 minutes, then tested for gel formation and antigen binding as described above. Different polymer lengths of poly-lysine are tested for gel formation upon formaldehyde treatment. In some embodiments, the poly-lysine comprises the L-enantiomer, the R-enantiomer, or a mixture of both L- and R-enantiomers. Poly-lysine gels containing various concentrations of an antigen are compared against negative controls such as a poly-lysine gel without antigen, or a poly-lysine gel with a non-specific protein or other antigen, and/or positive controls such as a gel described in Examples 1-10 (e.g., a 12.5% BSA gel containing the same antigen). These gels are assayed for antigen binding, e.g., on an IHC slide or TMA assayed by chromogenic or immunofluorescent binding assays as described in Examples 1-10.

Although the foregoing disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

What is claimed is:

1. A method for generating a solid antigen/carrier protein gel for immunohistochemical (IHC) staining, the method comprising:
   (a) mixing a purified antigen with a liquid solution comprising a carrier protein to produce an antigen/carrier protein liquid solution;
   (b) cross-linking the antigen with the carrier protein using a cysteine-reactive reagent; and
   (c) heating the antigen/carrier protein liquid solution to form the solid antigen/carrier protein gel,
   wherein the antigen is a polypeptide antigen comprising a C-terminal cysteine,
   wherein the carrier protein consists of a serum albumin protein, and
   wherein the antigen/carrier protein liquid solution further comprises formaldehyde.

2. The method of claim 1, further comprising, after (b): dehydrating the solid antigen/carrier protein gel and embedding the dehydrated solid antigen/carrier protein gel in a paraffin block.

3. The method of claim 1, further comprising, after (b): incubating the solid antigen/carrier protein gel in a liquid embedding medium and freezing the solid antigen/carrier protein gel in the embedding medium.

4. The method of claim 1, further comprising, after (b): embedding the solid antigen/carrier protein gel in a plastic resin.

5. The method of claim 1, wherein the antigen/carrier protein liquid solution comprises formaldehyde at a final concentration of at least about 1%.

6. The method of claim 1, further comprising:
   after (b), dehydrating the solid antigen/carrier protein gel;
   embedding the dehydrated solid antigen/carrier protein gel in a paraffin block;
   sectioning the paraffin block with the embedded antigen/carrier protein gel into one or more sections having a thickness of between about 30 nm and about 50 μm;
   subjecting the one or more sections of the embedded solid antigen/carrier protein gel to antigen retrieval; and
   after antigen retrieval, blocking the one or more sections of the embedded solid antigen/carrier protein gel.

7. The method of claim 1, further comprising:
   after (b), incubating the solid antigen/carrier protein gel in a liquid embedding medium;
   freezing the solid antigen/carrier protein gel in the embedding medium;
   sectioning the frozen antigen/carrier protein gel into one or more sections having a thickness of between about 30 nm and about 50 μm; and
   blocking the one or more sections of the frozen antigen/carrier protein gel.

8. The method of claim 1, wherein the antigen further comprises an N-terminal tyrosine.

9. The method of claim 1, wherein the serum albumin protein is bovine serum albumin.

10. The method of claim 1, wherein the antigen/carrier protein liquid solution produced in (a) comprises the carrier protein at a concentration of greater than or equal to 2% (w/v) and less than or equal to 25% (w/v).

* * * * *

UNITED STATES PATENT AND TRADEMARK OFFICE
CERTIFICATE OF CORRECTION

| | | |
|---|---|---|
| PATENT NO. | : 12,019,069 B2 | Page 1 of 1 |
| APPLICATION NO. | : 16/888252 | |
| DATED | : June 25, 2024 | |
| INVENTOR(S) | : Hötzel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 945 days.

Signed and Sealed this
Twenty-first Day of January, 2025

Coke Morgan Stewart
*Acting Director of the United States Patent and Trademark Office*